US012778921B2

(12) United States Patent
Gobbi et al.

(10) Patent No.: US 12,778,921 B2
(45) Date of Patent: Nov. 3, 2026

(54) MODULATORS OF THE MELATONIN RECEPTORS AS WELL AS METHOD OF MANUFACTURE AND USES THEREOF

(71) Applicant: COSMAS THERAPEUTICS DEVELOPMENT INC., Montreal (CA)

(72) Inventors: Gabriella Gobbi, Montreal (CA); Robert Zamboni, Beaconsfield (CA); Shiguang Li, Auburndale, MA (US)

(73) Assignee: COSMAS THERAPEUTICS DEVELOPMENT INC., Montréal (CA)

( * ) Notice: Subject to any disclaimer, the term of this patent is extended or adjusted under 35 U.S.C. 154(b) by 431 days.

(21) Appl. No.: 18/554,353

(22) PCT Filed: Apr. 6, 2022

(86) PCT No.: PCT/CA2022/050525

§ 371 (c)(1),
(2) Date: Oct. 6, 2023

(87) PCT Pub. No.: WO2022/213195

PCT Pub. Date: Oct. 13, 2022

(65) Prior Publication Data

US 2025/0339396 A1 Nov. 6, 2025

Related U.S. Application Data

(60) Provisional application No. 63/200,980, filed on Apr. 7, 2021.

(51) Int. Cl.

| | |
|---|---|
| ***C07C 233/36*** | (2006.01) |
| ***A61K 31/222*** | (2006.01) |
| ***A61K 31/265*** | (2006.01) |
| ***A61K 31/27*** | (2006.01) |
| ***A61K 31/40*** | (2006.01) |
| ***A61P 25/00*** | (2006.01) |
| ***A61P 25/02*** | (2006.01) |
| ***A61P 25/22*** | (2006.01) |
| ***A61P 29/00*** | (2006.01) |
| ***C07C 269/04*** | (2006.01) |
| ***C07C 271/64*** | (2006.01) |
| ***C07D 207/16*** | (2006.01) |

(52) U.S. Cl.

CPC .............. *A61K 31/27* (2013.01); *A61P 25/02* (2018.01); *A61P 25/22* (2018.01); *C07C 269/04* (2013.01); *C07C 271/64* (2013.01)

(58) Field of Classification Search

CPC ... C07C 233/36; C07C 271/64; C07D 207/16; A61K 31/27; A61K 31/40; A61K 31/222; A61K 31/265; A61P 25/00; A61P 29/00

See application file for complete search history.

(56) References Cited

FOREIGN PATENT DOCUMENTS

| | | |
|---|---|---|
| WO | 2007079593 A1 | 7/2007 |
| WO | 2015021535 A1 | 2/2015 |

OTHER PUBLICATIONS

American Psychiatric Association, Diagnostic and statistical manual of mental disorders (5th ed.) Washington, DC: (2013).

Bambico, F. R., Cassano, T., Dominguez-Lopez, S., Katz, N., Walker, C. D., Piomelli, D., & Gobbi, G., Genetic deletion of fatty acid amide hydrolase alters emotional behavior and serotonergic transmission in the dorsal raphe, prefrontal cortex, and hippocampus, Neuropsychopharmacology, (2010) 35(10), 2083-2100.

Bubenik, G. A., Gastrointestinal melatonin: localization, function, and clinical relevance, Dig Dis Sci, (2002) 47(10): 2336-2348.

Carrillo-Vico, A., J. R. Calvo, P. Abreu, P. J. Lardone, S. Garcia-Maurino, R. J. Reiter and J. M. Guerrero, Evidence of melatonin synthesis by human lymphocytes and its physiological significance: possible role as intracrine, autocrine, and/or paracrine substance, Faseb Journal, (2004)18(3): 537-539.

Chaplan, S. R., Bach, F. W., Pogrel, J. W., Chung, J. M., &Yaksh, T. L., Quantitative assessment of tactile allodynia in the rat paw, Journal of neuroscience methods, (1994) 53(1), 55-63.

Claustrat, B., J. Brun and G. Chazot, The basic physiology and pathophysiology of melatonin, Sleep Med Rev, (2005) 9(1): 11-24.

Comai, S. and G. Gobbi, Unveiling the role of melatonin MT2 receptors in sleep, anxiety and other neuropsychiatric diseases: a novel target in psychopharmacology, J Psychiatry Neurosci, (2014) 39(1): 6-21.

Comai, S., R. Ochoa-Sanchez and G. Gobbi, Sleep-wake characterization of double MT1/MT2 receptor knockout mice and comparison with MT1 and MT2 receptor knockout mice, Behavioural Brain Research, (2013) 243(1): 231-238.

Comai, S., R. Ochoa-Sanchez, S. Dominguez-Lopez, F. R. Bambico and G. Gobbi, Melancholic-Like behaviors and circadian neurobiological abnormalities in melatonin MT1 receptor knockout mice, Int J Neuropsychopharmacol, (2015) 18(3).

Decosterd, I., and Woolf, C. J., Spared nerve injury: an animal model of persistent peripheral neuropathic pain, Pain, (2000) 87(2), 149-158.

(Continued)

*Primary Examiner* — Brenda L Coleman

(74) *Attorney, Agent, or Firm* — Alain Dumont; Lavery, de Billy, L.L.P.

(57) ABSTRACT

There is provided compounds of formula (I) or a pharmaceutically acceptable salt thereof, which are melatonin MT2 agonists, as well as pharmaceutical compositions comprising such compounds. The invention also provides the use of the compounds and pharmaceutically acceptable salts thereof described herein (or pharmaceutical compositions comprising same) for managing or treating a disease, disorder or condition associated with melatonin receptor activity such as pain, neuropsychiatric disorders, sleep, chronobiological and circadian rhythm disorders, hyperthermia, and metabolic disorders. (I).

28 Claims, 10 Drawing Sheets

(56) References Cited

OTHER PUBLICATIONS

Dhillon, S. and M. Clarke, Tasimelteon: First global approval, Drugs, (2014) 74(4): 505-511.
Doolen, S., D. N. Krause, M. L. Dubocovich and S. P. Duckles, Melatonin mediates two distinct responses in vascular smooth muscle. European Journal of Pharmacology, (1998) 345(1): 67-69.
Dubocovich, M. L., P. Delagrange, D. N. Krause, D. Sugden, D. P. Cardinali and J. Olcese, International Union of Basic and Clinical Pharmacology. LXXV. Nomenclature, Classification, and Pharmacology of G Protein-Coupled Melatonin Receptors, Pharmacological Reviews, (2010) 62(3): 343-380.
Dubocovich, M. L., R. L. Hudson, I. C. Sumaya, M. I. Masana and E. Manna, Effect of MT1 melatonin receptor deletion on melatonin-mediated phase shift of circadian rhythms in the C57BL/6 mouse, Journal of Pineal Research, (2005) 39 (2): 113-120.
Electronic Medicine Compendium (EMC), entry on Valdoxan 25 mg film-coated tablets, https://www.medicines.org.uk/EMC/medicine/21830/SPC/Valdoxan/, last updated on Jul. 13, 2020.
FDA Final Labeling 21782/Supp 001, Rozerem (ramelteon) tablets, FDA document accessed via the Drugs@FDA database, document labelled Labelling in the database, dated Nov. 9, 2010, available at https://www.accessdata.fda.gov/drugsatfda_docs/label/2010/021782s011lbl.pdf.
Gobbi, G. and S. Comai, Differential Function of Melatonin MT1 and MT2 Receptors in REM and NREM Sleep. Front Endocrinol, (2019) 10(87).
Jockers, R., P. Delagrange, M. L. Dubocovich, R. P. Markus, N. Renault, G. Tosini, E. Cecon and D. P. Zlotos, Update on melatonin receptors: IUPHAR Review 20. Br J Pharmacol, (2016) 173(18): 2702-2725.
Johansson, L. C., B. Stauch, J. D. McCorvy, G. W. Han, N. Patel, X. P. Huang, A. Batyuk, C. Gati, S. T. Slocum, C. Li, J. M. Grandner, S. Hao, R. H. J. Olsen, A. R. Tribo, S. Zaare, L. Zhu, N. A. Zatsepin, U. Weierstall, S. Yous, R. C. Stevens, W. Liu, B. L. Roth, V. Katritch and V. Cherezov, XFEL structures of the human MT2 melatonin receptor reveal the basis of subtype selectivity. Nature, (2019) 569(7755): 289-292.
Jornada, D. H., G. F. dos Santos Fernandes, D. E. Chiba, T. R. de Melo, J. L. dos Santos and M. C. Chung, The Prodrug Approach: A Successful Tool for Improving Drug Solubility Molecule, (2015) s21(1): 42.
Karasek, M., Does melatonin play a role in aging processes? J Physiol Pharmacol, (2007) 58 Suppl 6: 105-113.
Kuriyama, A., M. Honda and Y. Hayashino, Ramelteon for the treatment of insomnia in adults: a systematic review and meta-analysis, Sleep Med, (2014) 15(4): 385-392.
Lacoste, B., D. Angeloni, S. Dominguez-Lopez, S. Calderoni, A. Mauro, F. Fraschini, L. Descarries and G. Gobbi (2015). Anatomical and cellular localization of melatonin MT1 and MT2 receptors in the adult rat brain, J Pineal Res, 58(4): 397-417.
Lemoine, P. and N. Zisapel, Prolonged-release formulation of melatonin (Circadin) for the treatment of insomnia. Expert Opin Pharmacother, (2012) 13(6): 895-905.
Lemoine, P., D. Garfinkel, M. Laudon, T. Nir and N. Zisapel, Prolonged-release melatonin for insomnia—an open-label long-term study of efficacy, safety, and withdrawal, Ther Clin Risk Manag, (2011) 7: 301-311.
Liu, J. and L. N. Wang, Ramelteon in the treatment of chronic insomnia: systematic review and meta-analysis, Int J Clin Pract, (2012) 66(9): 867-873.
Longatti, P., A. Perin, V. Rizzo, S. Comai, P. Giusti and C. V. Costa, Ventricular cerebrospinal fluid melatonin concentrations investigated with an endoscopic technique. J Pineal Res, (2007) 42(2): 113-118.
Lopez-Canul, M., E. Palazzo, S. Dominguez-Lopez, L. Luongo, B. Lacoste, S. Comai, D. Angeloni, F. Fraschini, S. Boccella, G. Spadoni, A. Bedini, G. Tarzia, S. Maione, V. Granados-Soto and G. Gobbi, Selective melatonin MT2 receptor ligands relieve neuropathic pain through modulation of brainstem descending antinociceptive pathways, Pain, (2015) 156(2): 305-317.
Lopez-Canul, M., S. Comai, S. Dominguez-Lopez, V. Granados-Soto and G. Gobbi Antinociceptive properties of selective MT2 melatonin receptor partial agonists, Eur J Pharmacol, (2015) 764: 424-432.
Lopez-Canul, M., S. H. Min, L. Posa, D. De Gregorio, A. Bedini, G. Spadoni, G. Gobbi and S. Comai, Melatonin MT1 and MT2 Receptors Exhibit Distinct Effects in the Modulation of Body Temperature across the Light/Dark Cycle. Int J Mol Sci, (2019) 20(10).
NDA 21-782, Rozerem (ramelteon) tablets, FDA document accessed via the Drugs@FDA database, document labelled Approval in the database, dated Jul. 17, 2005, pp. 4-21 followed by packaging, available at www.accessdata.fda.gov/drugsatfda_docs/label/2005/021782lbl.pdf.
Ochoa-Sanchez, R., Q. Rainer, S. Comai, G. Spadoni, A. Bedini, S. Rivara, F. Fraschini, M. Mor, G. Tarzia and G. Gobbi, Anxiolytic effects of the melatonin MT(2) receptor partial agonist UCM765: Comparison with melatonin and diazepam. Prog Neuropsychopharmacol Biol Psychiatry, (2012) 39(2): 318-325.
Ochoa-Sanchez, R., S. Comai, B. Lacoste, F. R. Bambico, S. Dominguez-Lopez, G. Spadoni, S. Rivara, A. Bedini, D. Angeloni, F. Fraschini, M. Mor, G. Tarzia, L. Descarries and G. Gobbi, Promotion of Non-Rapid Eye Movement Sleep and Activation of Reticular Thalamic Neurons by a Novel MT2 Melatonin Receptor Ligand, J.Neurosci., (2011) 31(50): 18439-18452.
Ohlsen, R. I. and L. S. Pilowsky, The place of partial agonism in psychiatry: recent developments, J Psychopharmacol, (2005) 19(4): 408-413.
Perreau-Lenz, S., A. Kalsbeek, M. L. Garidou, J. Wortel, J. van der Vliet, C. van Heijningen, V. Simonneaux, P. Pevet and R. M. Buijs Suprachiasmatic control of melatonin synthesis in rats: inhibitory and stimulatory mechanisms, Eur J Neurosci, (2003) 17(2): 221-228.
Reiter, R. J., Pineal melatonin: cell biology of its synthesis and of its physiological interactions, Endocr Rev, (1991) 12 (2): 151-180.
Reiter, R. J., D. X. Tan, R. M. Sainz, J. C. Mayo and S. Lopez-Burillo, Melatonin: reducing the toxicity and increasing the efficacy of drugs. J Pharm Pharmacol, (2002) 54(10): 1299-1321.
Righi, M., Bedini, A., Piersanti, G., Romagnoli, F. and Spadoni, G., Direct, One-Pot Reductive Alkylation of Anilines with Functionalized Acetals Mediated by Triethylsilane and TFA. Straightforward route for Unsymmetrically substituted Ethylenediamine, J. Org. Chem., 2011, 76(2), 704-707.
Rivara, S., A. Lodola, M. Mor, A. Bedini, G. Spadoni, V. Lucini, M. Pannacci, F. Fraschini, F. Scaglione, R. Ochoa-Sanchez, G. Gobbi and G. Tarzia, N-(substituted-anilinoethyl)amides: design, synthesis, and pharmacological characterization of a new class of melatonin receptor ligands, J.Med. Chem., (2007) 50(26): 6618-6626.
Rivara, S., F. Vacondio, A. Fioni, C. Silva, C. Carmi, M. Mor, V. Lucini, M. Pannacci, A. Caronno, F. Scaglione, G. Gobbi, G. Spadoni, A. Bedini, P. Orlando, S. Lucarini and G. Tarzia, N-(Anilinoethyl)amides: Design Metabolically Stable, Selective and Synthesis of Melatonin Receptor Ligands. ChemMedChem, (2009) 4(10): 1746-1755.
Spadoni, G., C. Balsamini, G. Diamantini, A. Tontini, G. Tarzia, M. Mor, S. Rivara, P. V. Plazzi, R. Nonno, V. Lucini, M. Pannacci, F. Fraschini and B. M. Stankov (2001). 2-N-acylaminoalkylindoles: design and quantitative structure-activity relationship studies leading to MT2-selective melatonin antagonists. J Med Chem, 44(18): 2900-2912.
Srinivasan, V., S. R. Pandi-Perumal, I. Trakht, D. W. Spence, R. Hardeland, B. Poeggeler and D. P. Cardinali, Pathophysiology of depression: role of sleep and the melatonergic system. Psychiatry Res, (2009) 165(3): 201-214.
Stauch, B., L. C. Johansson, J. D. McCorvy, N. Patel, G. W. Han, X. P. Huang, C. Gati, A. Batyuk, S. T. Slocum, A. Ishchenko, W. Brehm, T. A. White, N. Michaelian, C. Madsen, L. Zhu, T. D. Grant, J. M. Grandner, A. Shiriaeva, R. H. J. Olsen, A. R. Tribo, S. Yous, R. C. Stevens, U. Weierstall, V. Katritch, B. L. Roth, W. Liu and V. Cherezov, Structural basis of ligand recognition at the human MT1 melatonin receptor. Nature, (2019) 569(7755): 284-288.
Suckow M, Hankenson C, Wilson R, Foley P. (editors), The laboratory rat Academic Press; 3rd edition, (2019).

(56) References Cited

OTHER PUBLICATIONS

Taylor, J. B. and Triggle, D. J., Comprehensive Medicinal Chemistry II—vol. 6: Therapeutic Areas 1: Central Nervous System, Pain, Metabolic Syndrome, Urology, Gastrointestinal and Cardio Vascular, Oxford, Elsevier (2006) 771-826.
Tosini, G. and M. Menaker, The clock in the mouse retina: melatonin synthesis and photoreceptor degeneration. Brain Res, (1998) 789(2): 221-228.
Valdoxan 25mg film-coated tablet, Package Leaflet: Information for the patient, Europe, Les Laboratoires Servier, pp. 1-4, last revised May 2020.
Valdoxan: EPAR—Product Information made up to Annexes I to IIIB, document from the European Medicines Agency (EMA) database, last updated on Sep. 18, 2017, available at https://www.ema.europa.eu/en/medicines/human/EPAR/valdoxan#product-information-section (datebase entry on Valdoxan) and https://www.ema.europa.eu/en/documents/product-information/valdoxan-epar-product-information_en.pdf (specific documents including Annexes I to IIIB).
Martha López-Canul, Stefano Comai, Sergio Domínguez-López, Vinicio Granados-Soto, Gabriella Gobbi. Antinociceptive properties of selective MT2 melatonin receptor partial agonists. Eur J Pharmacol. Oct. 5, 2015:764:424-432. doi: 10.1016/j.ejphar.2015.07.010. Epub Jul. 7, 2015.
Dmytro I. Boiko, Anastasiia D. Shkodina, Mohammad Mehedi Hasan, Mainak Bardhan, Syeda Kanza Kazmi, Hitesh Chopra, Prerna Bhutra, Atif Amin Baig, Andrii M. Skrypnikov. Melatonergic Receptors (Mt1/Mt2) as a Potential Additional Target of Novel Drugs for Depression. Neurochemical Research (2022) 47:2909-2924. https://doi.org/10.1007/s11064-022-03646-5.
J. Liu, S. J. Clough and M. L. Dubocovich. Role of the MT1 and MT2 melatonin receptors in mediating depressive- and anxiety-like behaviors in C3H/HeN mice. Genes, Brain and Behavior (2017) 16: 546-553. doi: 10.1111/gbb.12369.
Angeliki Karamitri and Ralf Jockers. Melatonin in type 2 diabetes mellitus and obesity. Nat Rev Endocrinol. Feb. 2019; 15(2):105-125. doi: 10.1038/s41574-018-0130-1.

Table 6

| Entry | $R_1$ | $R_2$/eq | $R_3$ | Base/eq | NaI/eq | solvent | T/°C | Time /h | Isolated Yield% and Note | Scale |
|---|---|---|---|---|---|---|---|---|---|---|
| 1 | Me | $-(CH_2)_3-$ /2 | H | $Cs_2CO_3$/2 | - | $CH_3CN$ | rt | 96 | 47 | 0.1 |
| 2 | Me | $-(CH_2)_3-$ /2 | H | $Cs_2CO_3$/2 | - | THF | rt | 96 | ND | 0.1 |
| 3 | Me | $-(CH_2)_3-$ /2 | Ag | - | - | $CH_3CN$ | rt | 96 | ND | 0.1 |
| 4 | H | $-(CH_2)_3-$ /4 | H | $Cs_2CO_3$/4 | - | $CH_3CN$ | rt | 22 | 45 | 0.1 |
| 5 | H | $-(CH_2)_3-$ /4 | H | $Cs_2CO_3$/4 | - | $CH_3CN$ | rt | 18 | 65 | 0.2 |
| 6 | H | $-(CH_2)_3-$ /4 | H | $Cs_2CO_3$/4 | - | $CH_3CN$ DMF | rt | 48 | 84 | 0.5 |
| 7 | H | H/4 | H | $Cs_2CO_3$/4 | - | $CH_3CN$ | rt | 96 | Combine yield 21 | 0.2 |
| 8 | H | H/2 | Ag | - | - | $CH_3CN$ | rt | 96 | | 0.2 |
| 8 | Me | H/4 | H | $Cs_2CO_3$/4 | - | $CH_3CN$ | 50 | 20 | 40 | 0.1 |
| 9 | Me | H/4 | H | $Cs_2CO_3$/4 | - | $CH_3CN$ | 50 | 20 | 58 | 1.0 |
| 10 | H | H/4 | H | $Cs_2CO_3$/4 | - | $CH_3CN$ | 50 | 20 | Trace, decomposed | 0.1 |
| 11 | H | H/4 | H | $Cs_2CO_3$/4 | - | $CH_3CN$ | rt | 96 | 57 | 1.0 |
| 12 | H |  /4 | H | $Cs_2CO_3$/4 | - | $CH_3CN$ | rt | 96 | 37%, 40% of SM was recovered | 0.7 |

FIG. 8A

| Entry | $R_1$ | $R_2$/eq | $R_3$ | Base/eq | NaI/eq | solvent | T/°C | Time /h | Isolated Yield% and Note | Scale |
|---|---|---|---|---|---|---|---|---|---|---|
| 13 | H |  /4 | H | $Cs_2CO_3$/4 | 4 | $CH_3CN$ | rt | 5 | 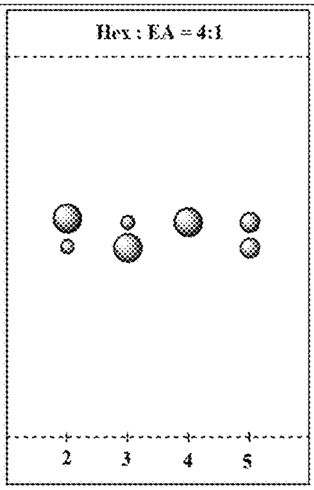 | 0.05 |
| 14 | H |  /4 | H | $Cs_2CO_3$/4 | 4 | DMF | rt | 5 | | 0.05 |
| 15 | H |  /4 | H | TEA/4 | 4 | $CH_3CN$ | rt | 5 | | 0.05 |
| 16 | H |  /4 | H | TEA/4 | 4 | DMF | rt | 5 | No isolated yield, TLC was used to determine the best conditions | 0.05 |
| 17 | H |  /4 | H | $Cs_2CO_3$/4 | 4 | DMF | rt | 17 | 87 | 0.8 |
| 18 | H | H/4 | H | $Cs_2CO_3$/4 | - | DMF | rt | 19 | 28, decomposed | 1.0 |
| 19 | H | H/4 | H | $Cs_2CO_3$/4 | - | DMF | rt | 4.5 | Combined yield 80 No obvious difference | 0.1 |
| 20 | H | H/3 | H | $Cs_2CO_3$/3 | - | DMF | rt | 4.5 | | 0.1 |
| 21 | H | H/2 | H | $Cs_2CO_3$/2 | - | DMF | rt | 4.5 | | 0.1 |
| 22 | H | H/2 | H | $Cs_2CO_3$/2 | - | DMF | rt | 4.5 | 80.3 | 5.0 |
| 23 | H | H/2 | H | $Cs_2CO_3$/2 | - | DMF | rt | 6 | 87.7 | 36 |

THF = tetrahydrofuran; DMF = dimethylformamide; TEA = triethylamine, rt = room temperature; SM = starting material; ND = not determined

FIG. 8B

MODULATORS OF THE MELATONIN RECEPTORS AS WELL AS METHOD OF MANUFACTURE AND USES THEREOF

CROSS REFERENCE TO RELATED APPLICATIONS

This application a National Entry Application of PCT application no PCT/CA2022/050525 filed on Apr. 6, 2022 and published in English under PCT Article 21(2), which itself claims benefit, under 35 U.S.C. § 119 (e), of U.S. provisional application Ser. No. 63/200,980, filed on Apr. 7, 2021. All documents above are incorporated herein in their entirety by reference.

FIELD OF THE INVENTION

The present disclosure relates to the modulation of the melatonin receptors through oral bioavailable drugs, and more particularly of the melatonin receptor subtype $MT_2$, and to the treatment of diseases and disorders associated with $MT_2$ activity such as pain, anxiety, and sleep disorders.

BACKGROUND OF THE INVENTION

Melatonin (MLT) is a neurohormone synthesized in the pineal gland during the dark period and released into the systemic circulation following a circadian rhythm (Dubocovich, Delagrange et al. 2010, Jockers, Delagrange et al. 2016). In addition to synthesis in the pineal gland, MLT can be synthesized by other tissues and cells, including the retina (Tosini and Menaker 1998), skin, bone marrow, lymphocytes (Carrillo-Vico, Calvo et al. 2004), and gastrointestinal tract (Bubenik 2002, Claustrat, Brun et al. 2005). MLT is synthesized from L-tryptophan in a series of biocatalyzed processes that are modulated by glutamatergic and peptidergic mechanisms (Reiter 1991). The pineal gland receives light signals from the retinohypothalamic system which leads to the release of epinephrine from the postganglionic sympathetic fibers. The released epinephrine binds to the post-synaptic B1-adrenoreceptors and induces an increase in cyclic adenosine-3',5'-monophosphate (cAMP), and activates N-acetyltransferase (Perreau-Lenz, Kalsbeek et al. 2003). The MLT is then released into circulation, crossing the blood brain barrier, and entering the CNS and peripheral tissues. Therefore, the fluctuating plasma concentration of MLT accurately reflects pineal gland activity (Reiter 1991, Longatti, Perin et al. 2007).

In humans, at the onset of MLT's secretion (around 21:00-22:00 h), circulating levels of MLT begin to rise to a peak level of 80-120 µg/mL (between 24:00 and 3:00 h); the offset of MLT secretion is at 7:00-9:00 h, when its serum levels begin falling to a low of 10-20 µg/mL in the light phase (Karasek 2007). MLT is involved in numerous physiological processes including circadian rhythms, mood regulation, anxiety, sleep, appetite, immune responses, cardiac functions and pain (Comai and Gobbi 2014). Most of the physiological effects of MLT result from the activation of two high-affinity (Ki=0.1 nM) G-protein coupled receptors (GPCRs) named MT1 and MT2. (Dubocovich, Delagrange et al. 2010). Interestingly, recent market analyses indicate that 40%-50% of modern drugs and almost 25% of the top 200 best-selling drugs target GPCRs (Thomsen and Behan 2007).

Unfortunately, the therapeutic use of MLT is limited by its i) short half-life (<30 min); ii) high first-pass metabolism; iii) binding of multiple receptors; iv) $MT_1$ and $MT_2$ receptors have opposing effects in physiological functions (Comai et al, 2014). Therefore, drug discovery efforts in the MLT area are being directed towards the development of subtype-selective MLT ligands.

A few melatonin analogs have been synthetized and all of them are non-selective $MT_1$/$MT_2$ receptors agonists. Similarly, a prolonged release formulation of MLT have been developed and commercialized for clinical use. Agomelatine is an antidepressant acting as an agonist of both $MT_1$ and $MT_2$ receptors and as an antagonist for 5-$HT_{2c}$ receptors (Srinivasan, Pandi-Perumal et al. 2009). Ramelteon is a non-selective agonist for both $MT_1$ and $MT_2$ receptors approved in the US for insomnia characterized by difficulty in falling asleep (Liu and Wang 2012, Kuriyama, Honda et al. 2014). A 2 mg prolonged release formulation of MLT has been approved in many countries as monotherapy for the short-term treatment of primary insomnia characterized by poor quality of sleep in patients who are aged 55 years or over (Lemoine and Zisapel 2012). Another non-selective $MT_1$/$MT_2$ receptors agonist, tasimelteon, has been approved for the treatment of non-24 hour sleep-wake disorder in blind individuals (Dhillon and Clarke 2014).

Unfortunately, all these compounds are not selective, thus targeting both theMT1 and $MT_2$ receptors, which receptors have opposing effects. The pharmacological efficacy of these compounds is also limited by their limited bioavailability; for example, the absolute oral bioavailability of Ramelteon is only 1.8% due to extensive first-pass metabolism (FDA, NDA21-782, https://www.accessdata.fda.gov/drugsatfda_docs/label/2010/021782s0111b1.pdf.; accessed online on 16 Nov. 2020). The bioavailability of Agomelatine is also low (<5% at the therapeutic oral dose) and the interindividual variability is substantial. The bioavailability is increased in women compared to men (EMA, https://www.ema.europa.eu/en/documents/product-information/valdoxan-epar-product-information_en.pdf.; accessed online on 16-10-020).

Although the overall clinical efficacy of these melatonergic compounds does not seem superior to that of other drugs not targeting MLT receptors, their effects reinforce the hypothesis that the MLT system is a useful target in neuropsychopharmacology. In particular, the MLT system seems to be a safe pharmacological target in terms of drug-induced toxicity (Reiter, Tan et al. 2002, Lemoine, Garfinkel et al. 2011).

More recently, the pharmacological characterization of the MT1 and MT2 receptors has been investigated, found that these receptors have a specific localization (Lacoste, Angeloni et al. 2015) and specific physiological functions, sometime also opposite (Gobbi and Comai 2019) thus incentivizing the development of selective receptor compounds, who target specific physiological functions and/or specific pathological disorders.

Specifically the agonism of MT1 receptors produces vasoconstriction (Doolen, Krause et al. 1998), increase in REM sleep, decrease in NREM sleep (Comai, Ochoa-Sanchez et al. 2013), has anti-depressant-like effects (Comai, Ochoa-Sanchez et al. 2015), increases temperature (Lopez-Canul, Min et al. 2019); while the MT2 agonism produces vasodilation (Doolen, Krause et al. 1998), promotes NREM, decreases the latency to sleep (Ochoa-Sanchez, Comai et al. 2011), has anxiolytic-like effects (Ochoa-Sanchez, Rainer et al. 2012) and analgesic effects in acute model of pain (Lopez-Canul, Comai et al. 2015) as well as in chronic neuropathic pain (Lopez-Canul, Palazzo et al. 2015) and has antidepressant-like effects (Dubocovich, Hudson et al. 2005).

During the last decade various modifications of the MLT structure were examined (Spadoni, Balsamini et al. 2001, Rivara, Lodola et al. 2007) using QSAR and molecular modelling studies and a 3D-QSAR COMFA approach (a) in order to determine what structural features are required for receptor affinity, intrinsic activity and/or subtype selectivity, and (b) in an attempt to identify compounds that might have therapeutic applications. More recently, the crystallographic structure of the $MT_1$ (Stauch, Johansson et al. 2019) and $MT_2$ receptor (Johansson, Stauch et al. 2019) has also been characterized.

A class of drugs, (N,N-di-substituted aminoethyl)-amides, that includes $MT_1$ and $MT_2$ receptors selective ligands was identified (WO/2007/079593, Rivara et al., (2007, 2009). Among those, compound UCM765 (N-{2-[(3-methoxyphenyl)-phenylamino]ethyl}acetamide) showed higher affinity for $MT_2$ (pKi=10.18) than for $MT_1$ (pKi=8.38) receptors, behaved as a $MT_2$ partial agonist (pKi=0.6), and displayed considerable hypnotic and antianxiety properties {Ochoa-Sanchez, 2011; Ochoa-Sanchez, 2012}. Compound UCM765 at the dose of 40 mg/kg facilitated restorative sleep (known as NREM sleep) through the activation of reticular thalamic neurons. (Ochoa-Sanchez, Comai et al. 2011) and possesses anti-anxiety properties (Ochoa-Sanchez, Rainer et al. 2012).

Importantly, it was demonstrated that the $MT_1$ and $MT_2$ receptors have distinct and opposing effects in sleep and anxiety, thus the importance to target one single receptor to enhance the pharmacological effects. (Ochoa-Sanchez, Comai et al. 2011, Comai, Ochoa-Sanchez et al. 2013).

Furthermore, it became clear that partial agonists were "intelligent drugs" since they produce a submaximal response of GPCR receptors without causing their desensitization and deactivation. For this reasons, today in psychopharmacology, they are preferred to agonists (Ohlsen and Pilowsky 2005).

Then, $MT_2$ receptor partial agonist UCM924 (N-{2-[(-[(3-bromophenyl)-(4-fluorophenyl)amino]ethyl}acetamide) was synthetized (WO2014/117253A1, WO2015021535A1, Rivara, Vacondio et al. 2009). Several tests for chronic neuropathic pain demonstrated that UCM924, like gabapentin (Neurontin®), has potent antinociceptive properties and unlike gabapentin did not produce any motor impairments in the RotaRod test (Lopez-Canul, Palazzo et al. 2015).

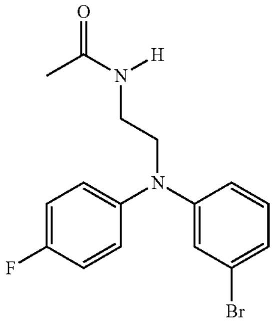

UCM 924

SUMMARY OF THE INVENTION

In accordance with the present invention, there is provided:

1. A compound of formula (I):

(I)

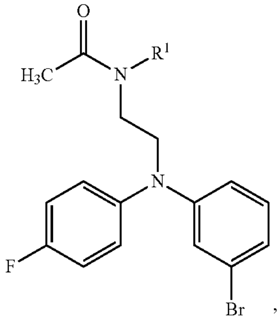

, wherein:

$R^1$ is:

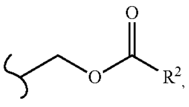

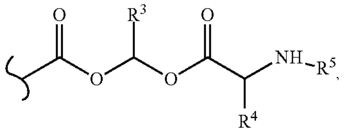

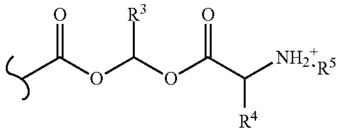

$A^-$, or

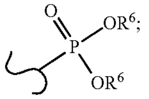

$R^2$ is an alkyl group or an —O-alkyl group;

$R^3$ is H or $CH_3$;

$R^4$ is H or a side chain of an amino acid and $R^5$ is H, or $R^4$ and $R^5$ together with the carbon atom and the nitrogen atom to which they are attached form a cyclopentyl group;

$OR^6$ represents OH, $O^-$ $Na^+$, or $O^-$ $K^+$; and

A is a pharmaceutically acceptable anion.

or a pharmaceutically acceptable salt thereof.

2. The compound of embodiment 1, wherein the alkyl group and/or the —O-alkyl group in $R^2$ contains between 1 and 18 carbon atoms, preferably between 1 and 12 carbon atoms, more preferably between 1 and 6 carbon atoms, and most preferably between 1 and 4 carbon atoms.

3. The compound of embodiment 1 or 2, wherein the alkyl group is a $C_{1-6}$ alkyl, preferably a $C_{1-4}$ alkyl, more preferably a $C_4$ alkyl, and most preferably tert-butyl.

4. The compound of any one of embodiments 1 to 3, wherein the alkyl in the —O-alkyl group is a $C_{1-6}$ alkyl, preferably a $C_{1-4}$ alkyl, and most preferably ethyl.

5. The compound of any one of embodiments 1 to 4, wherein $R^1$ is

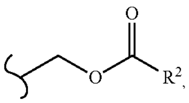

or

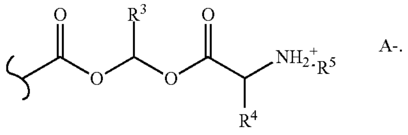

6. The compound of any one of embodiments 1 to 5, wherein $R^1$ is

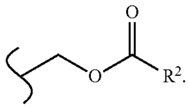

7. The compound of any one of embodiments 1 to 5, wherein $R^1$ is

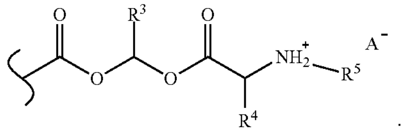

8. The compound of any one of embodiments 1 to 7, wherein $R^2$ is the alkyl group.

9. The compound of any one of embodiments 1 to 7, wherein $R^2$ is the —O-alkyl group.

10. The compound of any one of embodiments 1 to 9, wherein $R^4$ and $R^5$ are:

| $R^4$ | $R^5$ |
|---|---|
| $—CH_3$ | —H |
| $—CH(CH_3)_2$ | —H |
| $—CH(CH_3)—CH_2—CH_3$ | —H |
| $—CH_2—CH(CH_3)_2$ | —H |
| $—(CH_2)_2—S—CH_3$ | —H |
| 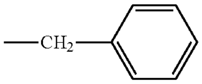 | —H |
| 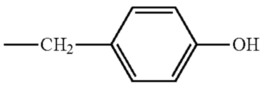 | —H |
| 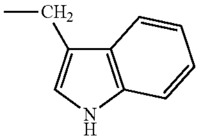 | —H |
| $—CH_2—OH$ | —H |
| $—CH(OH)—CH_3$ | —H |
| $—CH_2—C(=O)—NH_2$ | —H |
| $—(CH_2)_2—C(=O)—NH_2$ | —H |
| $—CH_2—SH$ | —H |

-continued

| $R^4$ | $R^5$ |
|---|---|
| $—CH_2—SeH$ | —H |
| —H | —H |
| $R^4$ and $R^5$ together with the carbon atom and the nitrogen atom to which they are attached form a cyclopentyl group | |
| $—(CH_2)_3—NH—C(=NH_2^+)—NH_2$ | —H |
| 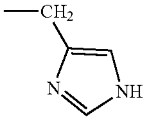 | —H |
| $—(CH_2)_4—NH_3^+$ | —H |
| $—CH_2—COO—$ | —H |
| $—(CH_2)_2—COO—$ | —H |

11. The compound of any one of embodiments 1 to 10, wherein $R^4$ and $R^5$ are:

| $R^4$ | $R^5$ |
|---|---|
| $—CH_2—CH(CH_3)_2$ | —H |
| —H | —H |

$R^4$ and $R^5$ together with the carbon atom and the nitrogen atom to which they are attached form a cyclopentyl group 12. The compound of any one of embodiments 1 to 11, wherein both $R^4$ and $R^5$ are H.

13. The compound of any one of embodiments 1 to 12, wherein $R^3$ is H.

14. The compound of any one of embodiments 1 to 13, whereinR3, $R^4$ and $R^5$ are H.

15. The compound of any one of embodiments 1 to 12, wherein $R^3$ is $CH_3$.

16. The compound of any one of embodiments 1 to 15, wherein the pharmaceutically acceptable anion is: aceglutamate, acephyllinate, acetamidobenzoate, acetate, acetylasparaginate, acetylaspartate, adipate, aminosalicylate, anhydromethylenecitrate, ascorbate, aspartate, benzoate, benzylate, besylate, bicarbonate, bisulphate, bitartrate, borate, bromide, butylbromide, camphorate, camsylate, carbonate, chloride, chlorophemoxyacetate, citrate, closylate, cromesilate, cyclamate, dehydrochloate, dihydrochloride, dimalonate, edetate, edisylate, estolate, esylate, ethylbromide, ethylsulfate, fendizoate, fluoride, formate, fosfatex, fumarate, gluceptate, gluconate, glucoronate, glutamate, glycerophosphate, glycinate, glycollylarsinilate, glycyrrhizate, hippurate, hemisulphate, hexylresorcinate, hybenzate, hydrobromide, hydrochloride, hydroiodide, hydroxybenzenesulfonate, hydroxybenzoate, iodide, isethionate, lactate, lactobionate, lysine, malate, maleate, mandalate, mesylate, methylbromide, methyliodide, methylnitrate, methylsulphate, monophosadenine, mucate, napadisylate, napsylate, nicotinate, nitrate, oleate, orotate, oxalate, oxoglurate, pamoate, pantothenate, pectinate, phenylethylbarbiturate, phosphate, picrate, policrilix, polistirex, pyridoxylphosphate, polygalacturonate, propionate, saccharinate, salicylate, stearate, stearylsulphate, subacetate, succinate, sulfate, sulfosalicylate, tannate, tartrate, teprosilate, terephthalate, teoclate, thiocyanate, timonaciate, tosylate, triethiodide, undecanoate, or xinafoate;

preferably acetate, besylate, bisulphate, bromide, carbonate, chloride, citrate, fluoride, formate, iodide, maleate, mesylate, methylsulphate, nitrate, nitrite, pamoate, phosphate, stearate, sulfate, or tartrate, more preferably, bromide, chloride, fluoride, iodide, or mesylate, preferably chloride or mesylate; and most preferably chloride.

17. The compound of embodiment 1 being:

(N-(2-((3-bromophenyl)(4-fluorophenyl)amino)ethyl)acetamido) methyl pivalate, (N-(2-((3-bromophenyl)(4-fluorophenyl)amino)ethyl)acetamido) methyl ethyl carbonate, 1-(acetyl(2-((3-bromophenyl)(4-fluorophenyl)amino)ethyl) carbamoyl)oxy)ethyl 2-aminoacetate hydrochloride, ((acetyl(2-((3-bromophenyl)(4-fluorophenyl)amino)ethyl) carbamoyl)oxy)methyl 2-aminoacetate hydrochloride, ((acetyl(2-((3-bromophenyl)(4-fluorophenyl)amino)ethyl) carbamoyl)oxy)methyl 2-aminoacetate methanesulfonate, (acetyl(2-((3-bromophenyl)(4-fluorophenyl)amino)ethyl) carbamoyl)oxy)methyl pyrrolidine-2-carboxylate hydrochloride, (2S)-1-((acetyl(2-((3-bromophenyl)(4-fluorophenyl)amino) ethyl)carbamoyl)oxy)ethyl pyrrolidine-2-carboxylate hydrochloride, or ((S)-((acetyl(2-((3-bromophenyl)(4-fluorophenyl)amino) ethyl)carbamoyl)oxy)methyl 2-amino-4-methylpentanoate hydrochloride.

or a pharmaceutically acceptable salt thereof.

18. The compound of embodiment 17, being ((acetyl(2-((3-bromophenyl)(4-fluorophenyl)amino)ethyl)carbamoyl)oxy)methyl 2-aminoacetate hydrochloride or a pharmaceutically acceptable salt thereof.

19. A pharmaceutical composition comprising the compound of any one of embodiments 1 to 18 or a pharmaceutically acceptable salt thereof and a pharmaceutically acceptable carrier or excipient.

20. Use of the compound or pharmaceutically acceptable salt thereof according to any one of embodiments 1 to 18, or the pharmaceutical composition of embodiment 19, for managing or treating a disease or disorder associated with melatonin $MT_2$ receptor activity.

21. Use of the compound or pharmaceutically acceptable salt thereof according to any one of embodiments 1 to 18, or the pharmaceutical composition of embodiment 19, for the manufacture of a medicament for managing or treating a disease, disorder or condition associated with melatonin $MT_2$ receptor activity.

22. A method for managing or treating a disease, disorder or condition associated with melatonin $MT_2$ receptor activity in a subject in need thereof comprising administering to the subject an effective amount of the compound or pharmaceutically acceptable salt thereof according to any one of embodiments 1 to 18, or the pharmaceutical composition of embodiment 19.

23. The compound or pharmaceutically acceptable salt thereof according to any one of embodiments 1 to 18, or the pharmaceutical composition of embodiment 19, for use in managing or treating a disease, disorder or condition associated with melatonin $MT_2$ receptor activity in a subject.

24. The use according to embodiment 20, the method according to embodiment 22, or the compound, pharmaceutically acceptable salt thereof or pharmaceutical composition for use according to embodiment 23, wherein said disease, disorder or condition is pain, a neuropsychiatric disorder, a sleep, chronobiological or circadian rhythm disorder, an eating disorder, hyperthermia, or a metabolic disorder.

25. The use, method, compound, pharmaceutically acceptable salt thereof or pharmaceutical composition for use according to embodiment 24, wherein said disease, disorder or condition is pain.

26. The use, method, compound, pharmaceutically acceptable salt thereof or pharmaceutical composition for use according to embodiment 24 or 25, wherein the pain is chronic pain or acute pain.

27. The use, method, compound, pharmaceutically acceptable salt thereof or pharmaceutical composition for use according to any one embodiments 24 to 26, wherein the pain is chronic pain.

28. The use, method, compound, pharmaceutically acceptable salt thereof or pharmaceutical composition for use according to any one of embodiments 24 to 26, wherein the pain is acute pain.

29. The use, method, compound, pharmaceutically acceptable salt thereof or pharmaceutical composition for use according to any one of embodiments 24 to 28, wherein the pain is:

chronic pain, acute tonic pain;

pain relating to surgery (e.g., post-surgical pain, surgical pain);

pain relating to trauma (including post-traumatic pain);

hyperalgesia pain;

allodynic pain;

myalgic pain;

inflammatory pain (e.g., pain associated with an inflammatory disease or condition), including chronic inflammatory pain;

neuropathic pain;

headache including tension headache;

visceral pain;

pelvic pain;

nociceptive pain; and/or pain associated with a disorder or condition.

30. The use, method, compound, pharmaceutically acceptable salt thereof or pharmaceutical composition for use according to embodiment 29, wherein the pain is nociceptive pain.

31. The use, method, compound, pharmaceutically acceptable salt thereof or pharmaceutical composition for use according to embodiment 29 or 30, wherein the nociceptive pain is visceral pain or somatic pain, for example musculo-skeletal pain or post-traumatic pain.

32. The use, method, compound, pharmaceutically acceptable salt thereof or pharmaceutical composition for use according to embodiment 29, wherein the pain is neuropathic pain.

33. The use, method, compound, pharmaceutically acceptable salt thereof or pharmaceutical composition for use according to embodiment 29 or 32, wherein the neuropathic pain is peripheral neuropathic pain; central neuropathic pain; back pain, such as low-back pain; joint pain; post-herpetic neuralgia, cancer-related pain, pain related to spinal cord injury, pain caused by reflex sympathetic dystrophy, HIV-associated pain, phantom pain, post-stroke pain, pain caused by trigeminal neuralgia; and/or head pain (e.g., headache).

34. The use, method, compound, pharmaceutically acceptable salt thereof or pharmaceutical composition for use according to embodiment 29, wherein the pain is inflammatory pain, e.g., pain associated with a disorder or condition.

35. The use, method, compound, pharmaceutically acceptable salt thereof or pharmaceutical composition for use according to embodiment 29 or 34, wherein the disorder or condition is fibromyalgia, irritable bowel syndrome, arthritis, ulcer (including gastric ulcer), diabetic neuropathy (including diabetic Type 1 and Type 2 peripheral neuropathy), sciatica, migraine, and/or pain associated to vulvodynia.

36. The use, method, compound, pharmaceutically acceptable salt thereof or pharmaceutical composition for use according to embodiment 24, wherein said disease, disorder or condition is a neuropsychiatric disorder.

37. The use, method, compound, pharmaceutically acceptable salt thereof or pharmaceutical composition for use according to embodiment 24 or 36, wherein the neuropsychiatric disorder is an attention deficit disorder, a cognitive deficit disorder, autism spectrum disorder, migraine headaches, an addiction, an eating disorder, a mood disorder (such as depression) or an anxiety disorder.

38. The use, method, compound, pharmaceutically acceptable salt thereof or pharmaceutical composition for use according to any one of embodiments 24, 36 and 37, wherein the neuropsychiatric disorder is a mood disorder.

39. The use, method, compound, pharmaceutically acceptable salt thereof or pharmaceutical composition for use according to embodiment 37 or 38, wherein the mood disorder is depression (for example major depressive disorder) or seasonal affective disorder (SAD).

40. The use, method, compound, pharmaceutically acceptable salt thereof or pharmaceutical composition for use according to any one of embodiments 24, 36 and 37, wherein the neuropsychiatric disorder is an anxiety disorder (such as generalized anxiety).

41. The use, method, compound, pharmaceutically acceptable salt thereof or pharmaceutical composition for use according to embodiment 24, wherein said disease, disorder or condition is a sleep, chronobiological and/or circadian rhythm disorder, preferably a sleep disorder.

42. The use, method, compound, pharmaceutically acceptable salt thereof or pharmaceutical composition for use according to embodiment 24 or 41, wherein the sleep, chronobiological and/or circadian rhythm disorder is a sleep disorder (such as insomnia, apnea insomnia associated to pain, narcolepsy, restless leg syndrome, parasomnias, REM sleep behavior disorder, non-24 hour sleep wake disorders, and sleep disorders associated to mental disorders), a sleep-wake disorder, or a sleep disorder associated to mental disorders (including autism spectrum disorder).

43. The use, method, compound, pharmaceutically acceptable salt thereof or pharmaceutical composition for use according to embodiment 24, wherein said disease, disorder or condition is a metabolic disorder.

44. The use, method, compound, pharmaceutically acceptable salt thereof or pharmaceutical composition for use according to embodiment 24 or 43, wherein the metabolic disorder is impaired glucose tolerance, insulin resistance and/or diabetes.

45. The use, method, compound, pharmaceutically acceptable salt thereof or pharmaceutical composition for use according to embodiment 24, 43, or 44, wherein the metabolic disorder is diabetes, such as type 2 or type 1 diabetes.

46. A method of manufacturing N-{2-[(-[(3-bromophenyl)-(4-fluorophenyl)amino]ethyl}acetamide (UCM924):

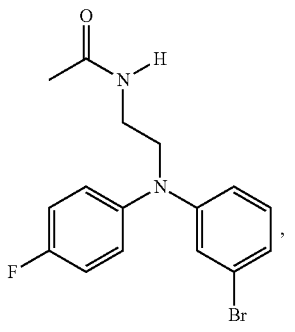

UCM 924 the method comprising the steps of:

i) reacting 3-bromoaniline

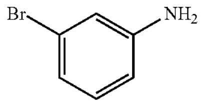

with 1-fluoro-4-iodobenzene

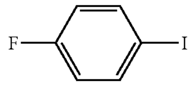

to produce 3-bromo-N-(4-fluorophenyl)aniline:

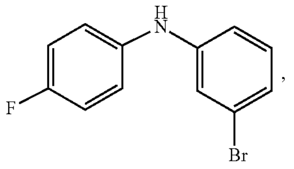 [SMILES: Fc1ccc(Nc2cccc(Br)c2)cc1]

ii) salifying the 3-bromo-N-(4-fluorophenyl)aniline to produce a 3-bromo-N-(4-fluorophenyl)aniline salt, and isolating said salt as a solid, and iii) reacting the 3-bromo-N-(4-fluorophenyl)aniline salt with N-(2,2-dimethoxyethyl)acetamide

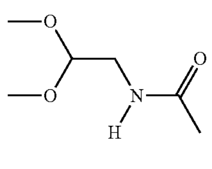

to produce UCM924.

47. The method of embodiment 46, wherein the 3-bromoaniline and the 1-fluoro-4-iodobenzene are reacted at step i) in one or more, preferably all of, the following conditions:
   in the presence of an excess of 1-fluoro-4-iodobenzene, preferably in an amount of about 1 to about 5 times, preferably about 1 to about 2 times the stoichiometric amount, and more preferably in an amount of about 1.05 times the stoichiometric amount,
   in the presence of a palladium catalyst; such as palladium pivalate, palladium(ii) bromide, palladium(ii) acetylacetonate, palladium(ii) iodide, palladium(ii) trifluoroacetate, palladium(ii) propionate, palladium (ii) chloride, dichiorobis(triethylphosphine) palladium(ii), palladium(ii) hexafluoroacetylacetonate, tetrakis(triphenylphosphine) palladium(0), bis(triphenylphosphine) palladium(ii) dichloride, bis(dibenzylideneacetone)palladium(0), dichlorobis(tricyclohexylphosphine) palladium(ii), dichloro(1,5-cyclooctadiene) palladium(ii), bis (dibenzylideneacetone)palladium(0), or palladium (II) acetate ($Pd(OAc)_2$), preferably $Pd(OAc)_2$; preferably in an amount of at least 0.04 times the stoichiometric amount, for example, the catalyst can be at a concentration of about 0.1 mol % to about 10 mol %, preferably of about 1 mmol % to about 5 mmol %.
   in the presence of a ligand, preferably a phosphine ligand, more preferably triphenylphosphine, XPhos (dicyclohexyl [2',4',6'-tris(propan-2-yl) [1,1'-biphenyl]-2-yl]phosphane), Xantphos (4,5-bis(diphenylphosphino)-9,9-dimethylxanthene), 1,1'-bis(diphenylphosphino) ferrocene (DPPF), RuPhos (2-dicyclohexylphosphino-2',6'-diisopropoxybiphenyl), SPhos (dicyclohexyl(2',6'-dimethoxy [1,1'-biphenyl]-2-yl)phosphane), tricyclohexylphosphine, BrettPhos (2-(dicyclohexylphosphino) 3,6-dimethoxy-2',4',6'-triisopropyl-1,1'-biphenyl), JohnPhos ((2-biphenylyl)di-tert-butylphosphine, 2-(di-tert-butylphosphino) biphenyl, (2-biphenyl)di-tert-butylphosphine), tBuXPhos (2-di-tert-butylphosphino-2',4',6'-triisopropylbiphenyl), DavePhos (2-dicyclohexylphosphino-2'-(N,N-dimethylamino) biphenyl), or 2,2'-bis(diphenylphosphino)-1,1'-binaphthyl (BINAP), more preferably, 2'-bis(diphenylphosphino)-1,1'-binaphthyl (BINAP); preferably in an amount of at least 0.05 times the stoichiometric amount,
   in the presence of a base, preferably $Na_2CO_3$, $K_2CO_3$, $Cs_2CO_3$, KF, sodium tert-butoxide, KOH, NaOH, $K_3PO_4$, or potassium tert-butoxide, more preferably potassium tert-butoxide, preferably in excess, more preferably in an amount of about 1 to about 5 times, preferably 1.2 to 2 times the stoichiometric amount, and yet more preferably in an amount of about 1.5 times the stoichiometric amount,
   in a solvent, preferably dioxane, tetrahydrofuran, 2-methyltetrahydrofuran, or toluene, more preferably toluene, preferably in a concentration of about 0.1M to about 1M, preferably about 0.25M to about 0.75M, and most preferably at a concentration of about 0.5M,
   at a temperature of about 50° C. to about 120° C., preferably about 50° C. to about 120° C., and more preferably at a temperature of 100° C.,
   for about 1 h to about 48 h, preferably 4 h to about 10 h, and more preferably for about 4 h to about 6 h, and/or (preferably and)
   under an inert atmosphere, preferably argon or nitrogen.
48. The method of embodiment 46 or 47, wherein step i) comprises preparing a solution of the 3-bromoaniline, the 1-fluoro-4-iodobenzene, the ligand, and the catalyst in the solvent, preferably stirring the solution for about 10 minutes to about 60 minutes (more preferably 30 minutes), and then adding the base to the solution.
49. The method of any one of embodiments 46 to 48, wherein the 3-bromo-N-(4-fluorophenyl)aniline are salified at step ii) in one or more, preferably all of, the following conditions:
   with an acid such as $H_2SO_4$, formic acid, or HCl, preferably HCl; preferably in excess, more preferably in an amount of about 1 to about 10 times, preferably about 1 to about 2 times the stoichiometric amount, and yet more preferably in an amount of about 1.5 times the stoichiometric amount,
   in a solvent, preferably diethyl ether, tert-butyl methyl ether, ethyl acetate, or dioxane, and more preferably dioxane,
   at a temperature of about 0° C. to about 30° C., preferably at room temperature, and/or (preferably and)
   for about 30 minutes to about 24 h, preferably for about 1 h to about 5 h, more preferably for about 2 h.
50. The method of any one of embodiments 46 to 49, wherein the 3-bromo-N-(4-fluorophenyl)aniline is salified with HCl at step ii).
51. The method of any one of embodiments 46 to 50, wherein the 3-bromo-N-(4-fluorophenyl)aniline salt and the N-(2,2-dimethoxyethyl)acetamide are reacted at step iii) in one or more, preferably all of, the following conditions:
   in the presence of N-(2,2-dimethoxyethyl)acetamide, preferably in excess, more preferably in an amount of about 1 to about 3 times the stoichiometric amount, and even more preferably in an amount of about 1.4 times the stoichiometric amount,
   in the presence trifluoroacetic acid; preferably in excess, more preferably in an amount of about 1 to about 20 times, yet more preferably about 1 to about 6 times the stoichiometric amount, and even more preferably in an amount of about 3 to about 4 times the stoichiometric amount,
   in the presence of triethylsilane, preferably in excess, more preferably in an amount of about 1 to about 5 times, yet more about 2 to about 4 times the stoichiometric amount, and even more preferably in an amount of 2.5 times the stoichiometric amount,
   in a solvent, preferably chloroform, tetrahydrofuran, 2-methyltetrahydrofuran, diethyl ether, 1,2-dichloroethane, dichloromethane, and more preferably dichloromethane,
   at a temperature of about-10° C. to about 50° C., preferably about 0° C. to about 30° C., and more preferably at room temperature, and/or (preferably and).
   for about 1 h to about 24 h, preferably about 2 to about 10 h, and more preferably for about 3.5 h.
52. The method of any one of embodiments 46 to 51, wherein step iii) comprises the step of combining the 3-bromo-N-(4-fluorophenyl)aniline salt, the N-(2,2-dimethoxyethyl)acetamide, the trifluoroacetic acid, and the triethylsilane at a temperature of about −10° C. to about 10° C., preferably at about 0° C., for about 5 minutes to about 30 minutes, preferably for about 10 minutes, and before performing the reaction.

53. A method of manufacture of a compound of formula (II):

(II)

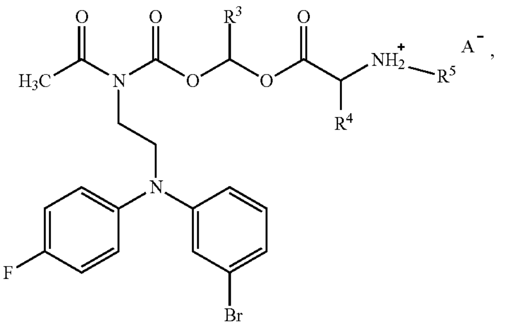

wherein $A^-$, $R^3$, $R^4$ and $R^5$ are as defined in any one of embodiments 1 to 15, the method comprising the steps of:

1. providing N-{2-[(-[(3-bromophenyl)-(4-fluorophenyl)amino]ethyl}acetamide (UCM924):

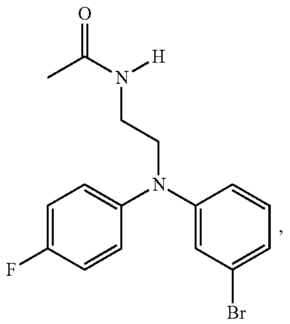

UCM 924

2. reacting UCM924 with a first base and a reactant of formula (IV) to produce a chloromethyl intermediate of formula (V):

(IV)

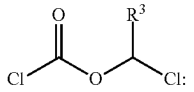

-continued (V)

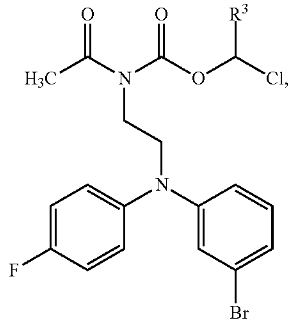

wherein $R^3$ is as defined in any one of embodiments 1 to 15;

3. reacting the chloromethyl intermediate of formula (V) with a second base and a reactant of formula (VI) to produce a protected compound of formula (VII):

(VI)

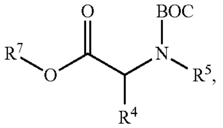

(VII)

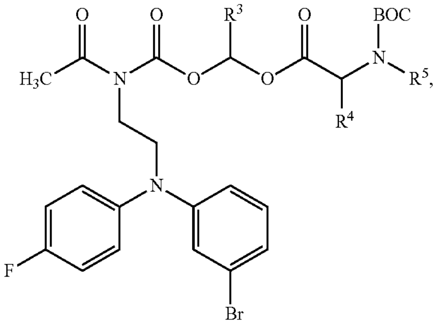

wherein $R^4$ and $R^5$ as described in any one of embodiments 1 to 15, $R_7$ represents H, Li, Na, K, Cs, or Ag, and BOC represents a tert-butyloxycarbonyl protecting group; and 4. reacting the protected compound of formula (VII) with an acid of formula $H^+ E^-$, to produce a salt of formula (VIII):

(VIII)

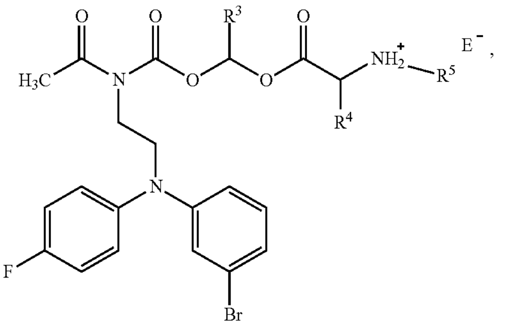

wherein $E^-$ is an anion, and 5. when $E^-$ is not a pharmaceutically acceptable anion, performing a salt metathesis to replace $E^-$ with a pharmaceutically acceptable anion ($A^-$), thus producing the compound of formula (II).

54. The method of embodiment 53, wherein, in step 1, UCM924 is manufactured according to the method of any one of embodiments 46 to 52.

55. The method of embodiment 53 or 54, wherein the first base is a base of an alkaline metal, preferably lithium bis(trimethylsilyl)amide (LiHMDS), sodium bis(trimethylsilyl)amide, or lithium diisopropylamide (LDA), more preferably lithium bis(trimethylsilyl)amide (LiHMDS).

56. The method of any one of embodiments 53 to 55, wherein step 2 comprises:

2' preparing a reaction mixture comprising UCM924 and the first base,

2" allowing UCM924 and the first base to react and produce an intermediate of formula (IX):

(IX)

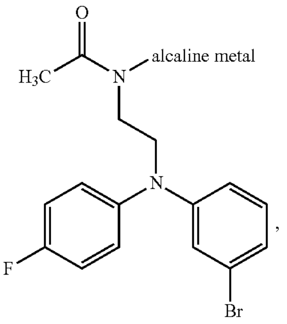

and

2'" reacting the intermediate of formula (IX) with the reactant of formula (IV) to produce a chloromethyl intermediate of formula (V).

57. The method of embodiment 56, wherein, at step 2", the UCM924 and the first base are allowed to react for about 10 minutes to about 24 h, preferably for about 1 h to about 5 h, more preferably for about 1 h to about 3 h, and most preferably for about 120 minutes, before step 2".

58. The method of embodiment 56 or 57, wherein step 2" comprises adding a solution of the reactant of formula (IV), preferably in the first solvent, dropwise to the reaction mixture, preferably in about 10 minutes to about 10 h, more preferably in about 30 minutes to about 3 h, and most preferably in about 60 minutes to about 90 minutes.

59. The method of any one of embodiments 57 to 58, wherein the reaction in step 2" is allowed to continue for about 0.5 h to about 24 h, preferably for about 0.5 h to about 3 h, more preferably for about 90 to 120 minutes, and most preferably for about 120 minutes, after the reactant of formula (IV) is added.

60. The method of any one of embodiments 53 to 59, wherein step 2 is carried out in tetrahydrofuran, 2-methyltetrahydrofuran, diethyl ether, tert-butyl methyl ether, 1,4-dioxane, toluene, dimethoxyethane, benzene, or a mixture thereof, preferably in tetrahydrofuran, as a first solvent.

61. The method of any one of embodiments 53 to 60, wherein step 2 is carried out in the presence of the first base in about the stoichiometric amount for the reaction, preferably the quantity of first base used about 1.05 times the stoichiometric amount for the reaction, and more preferably the concentration of the first base during step 2 is 1M.

62. The method of any one of embodiments 53 to 61, wherein step 2 is carried out in the presence of an excess of the reactant of formula (IV), preferably the quantity of reactant of formula (IV) used is about 1 to about 10 times, preferably about to about 5 times, preferably about 2 times the stoichiometric amount for the reaction.

63. The method of any one of embodiments 53 to 62, wherein step 2 is carried in an anhydrous atmosphere, preferably an inert atmosphere, more preferably in argon.

64. The method of any one of embodiments 53 to 63, wherein step 2 is carried out at a temperature of about-10° C. to about 23° C., preferably about 0° C. to about 10° C., and more preferably at a temperature of about 5° C.

65. The method of any one of embodiments 53 to 64, wherein the method further comprises the step of isolating, and preferably purifying, the chloromethyl intermediate of formula (V) before step 3.

66. The method of any one of embodiments 53 to 65, wherein $R_7$ is H.

67. The method of any one of embodiments 53 to 66, wherein the second base is $Cs_2CO_3$, triethylamine, CsCl, tert-butyl-OK, tert-butyl-ONa, methyl-ONa, $Cs_2CO_3$, $Na_2CO_3$, $K_2CO_3$, $NaHCO_3$, $KHCO_3$, NaH, KH, LiOH, NaOH, CsOH, or KOH, preferably a base of a monovalent metal, more preferably KOH.

68. The method of any one of embodiments 53 to 67, wherein, when the second base is a base of a monovalent metal (e.g., Li, K, Na, Cs), step 3 can comprise:

3' preparing a reaction mixture comprising the reactant of formula (VI) wherein $R_7$ is H, and the second base, 3" allowing the reactant of formula (VI) and the second base to react and produce a reactant of formula (X):

(X)

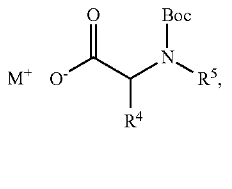

wherein $M^+$ is a monovalent metal cation, and reacting the intermediate of formula (IX) with the reactant of formula (X) to produce a protected compound of formula (VII).

69. The method of embodiment 68, wherein the monovalent metal cation is Lit, $Na^+$, $K^+$, or $Cs^+$.

70. The method of embodiment 68 or 69, wherein, at step 3", the reactant of formula (VI) and the second base are allowed to react for about 0.5 h to about 24 h, preferably for about 1 h to about 3 h, and more preferably for about 180 minutes, before step 3' ".

71. The method of any one of embodiments 68 to 70, wherein step 3" comprises adding the reaction mixture obtained at step 3", preferably dropwise, to a solution of the intermediate of formula (IX), preferably in about 10 minutes to about 10 h, preferably about 20 minutes to about 60 minutes, and more preferably in about 40 minutes.

72. The method of any one of embodiments 68 to 71, wherein the reaction is allowed to continue for about 2 h to about 7 days, preferably for about 20 h, after the intermediate of formula (IX) is added.

73. The method of any one of embodiments 53 to 72, wherein step 3 is carried out in tetrahydrofuran, $CH_3CN$, dimethylformamide, preferably in dimethylformamide as a second solvent.

74. The method of any one of embodiments 53 to 73, wherein step 3 is carried out in the presence of an excess of the reactant of formula (VI), preferably the quantity of reactant of formula (VI) used is in about 1 to about 10 times, preferably about 1 to about 5 times, yet more preferably about 2 to 4 times, and most preferably 2 times the stoichiometric amount for the reaction.

75. The method of any one of embodiments 53 to 74, wherein step 3 is carried out in the presence of an excess of the second base, particularly when $R_7$ represents H; preferably step 3 is carried out in the presence the second base in a quantity that is 1 to 10 times, preferably about 1 to about 5 times, and more preferably about 1 to about 2 times the stoichiometric amount for the reaction, preferably about the stoichiometric amount for the reaction.

76. The method of any one of embodiments 53 to 75, wherein step 3 is carried in an anhydrous atmosphere, preferably an inert atmosphere, more preferably in argon.

77. The method of any one of embodiments 53 to 76, wherein step 3 is carried out at a temperature of about 0° C. to about 50° C., preferably 10° C. to about 30° C., and most preferably at room temperature.

78. The method of any one of embodiments 53 to 77, further comprising the step of isolating, and preferably purifying, the protected compound of formula (VII) before step 4.

79. The method of any one of embodiments 53 to 78, wherein the acid in step 4 is citric acid, acetic acid, trifluoroacetic acid, phosphorous acid, phosphoric acid, formic acid, oxalic acid, nitric acid, boric acid, gluconic acid, lactic acid, tartaric acid, methanesulfonic acid, p-toluenesulfonic acid, benzenesulfonic acid, $H_2SO_4$, or HCl, preferably HCl.

80. The method of any one of embodiments 53 to 79, wherein step 4 is carried out in the presence of an excess of the acid (VI), preferably the quantity of reactant of formula (VI) used is about 2 to about 100 times, preferably about 5 to about 15 times, and more preferably 10 times the stoichiometric amount for the reaction.

81. The method of any one of embodiments 53 to 80, wherein step 4 is carried out in methanol, ethanol, isopropyl alcohol, diethyl ether, $CH_3CN$, tetrahydrofuran, 2-methyltetrahydrofuran, dichloromethane, acetone, chloroform, methyl tert-butyl ether, dioxane, preferably in dioxane, as a third solvent.

82. The method of any one of embodiments 53 to 81, wherein step 4 is carried out for about 0.5 h to about 6 h, preferably for about 0.5 h to 2.5 h, and more preferably for about 40 minutes.

83. The method of any one of embodiments 53 to 82, wherein step 4 is carried out at a temperature of about-10° C. to about 50° C., preferably about 0° C. to about 30° C., preferably at a temperature of about 0° C. to room temperature, and more preferably at room temperature.

84. A method of manufacture of a compound of the invention of formula (VI):

(VI)

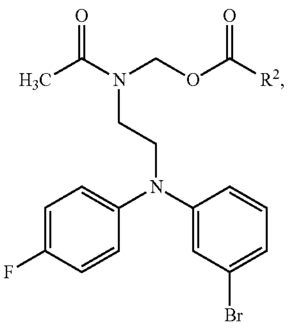

wherein $R^2$ is as described in any one of embodiments 1 to 15, the method comprising the steps of:

A. providing UCM924; and

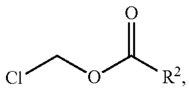

B. reacting UCM924 with wherein $R^2$ is as described in any one of embodiments 1 to 15, in the presence of NaH thus producing the compound of formula (VI).

85. The method of embodiment 84, wherein, in step A, UCM924 is manufactured according to the the method of any one of embodiments 46 to 52.

86. The method of embodiment 84 or 85, wherein step B is carried out in dimethylformamide, tetrahydrofuran, 2-methyltetrahydrofuran, dimethyl sulfoxide, dimethylacetamide, or N-methyl-2-pyrrolidone, preferably in dimethylformamide as a solvent.

87. The method of any one of embodiments 84 to 86, wherein step B is carried out at a temperature between about −78° C. and about 100° C., preferably between about 0° C. and about 30° C., and more preferably at room temperature.

88. The method of any one of embodiments 84 to 87, wherein step B is carried out for about 1 h to about 48 h, preferably for about 3 h to 24 h, and more preferably for about 3 h.

BRIEF DESCRIPTION OF THE DRAWINGS

In the appended drawings:

FIG. 1A: changes in 50% paw withdrawal threshold over time. FIG. 1B: Area under the curve (AUC) of FIG. 1A. Results are expressed as mean±sem. *p<0.05 vs. vehicle, p<0.001 vs. vehicle, *p<0.0001 vs. vehicle. N=8-25/group.

FIG. 2A: changes in 50% paw withdrawal threshold over time. FIG. 2B: Area under the curve (AUC) of FIG. 2A. Results are expressed as meantsem. *p<0.05 vs vehicle, p<0.01 vs vehicle, *p<0.001, ****p<0.0001 vs vehicle; xx p<0.01 vs Prodrug E by Bonferroni post-hoc test. N=8-25/group.

FIG. 3A: changes in 50% withdrawal threshold over time. FIG. 3B: Area under the curve (AUC) of FIG. 3A. Results are expressed as mean±sem. *p<0.05 vs vehicle, p<0.01 vs vehicle, *p<0.001, ****p<0.0001 vs vehicle by Bonferroni post-hoc test. N=8-25/group.

FIG. 6A: open arm time.

FIG. 6B: entries to open arm. FIG. 6C: closed arm time. FIG. 6D: distance travelled. p<0.01, *p<0.001 FIG. 7A: REM time (A). FIG. 7B: NREM time. FIG. 7C: time in wakefulness. FIG. 7D: sleep fragmentation index (SFI). Sham=9, SNI+VEH=5, SNI+ProdrugD=5, One-way ANOVA, followed by Bonferroni post-hoc test, *p<0.05, p<0.01, **p<0.0001

FIG. 8A-B depict a table (Table 6) showing the conditions and results for the second reaction step of Reaction scheme A.

DETAILED DESCRIPTION OF THE INVENTION

Figure 1A:
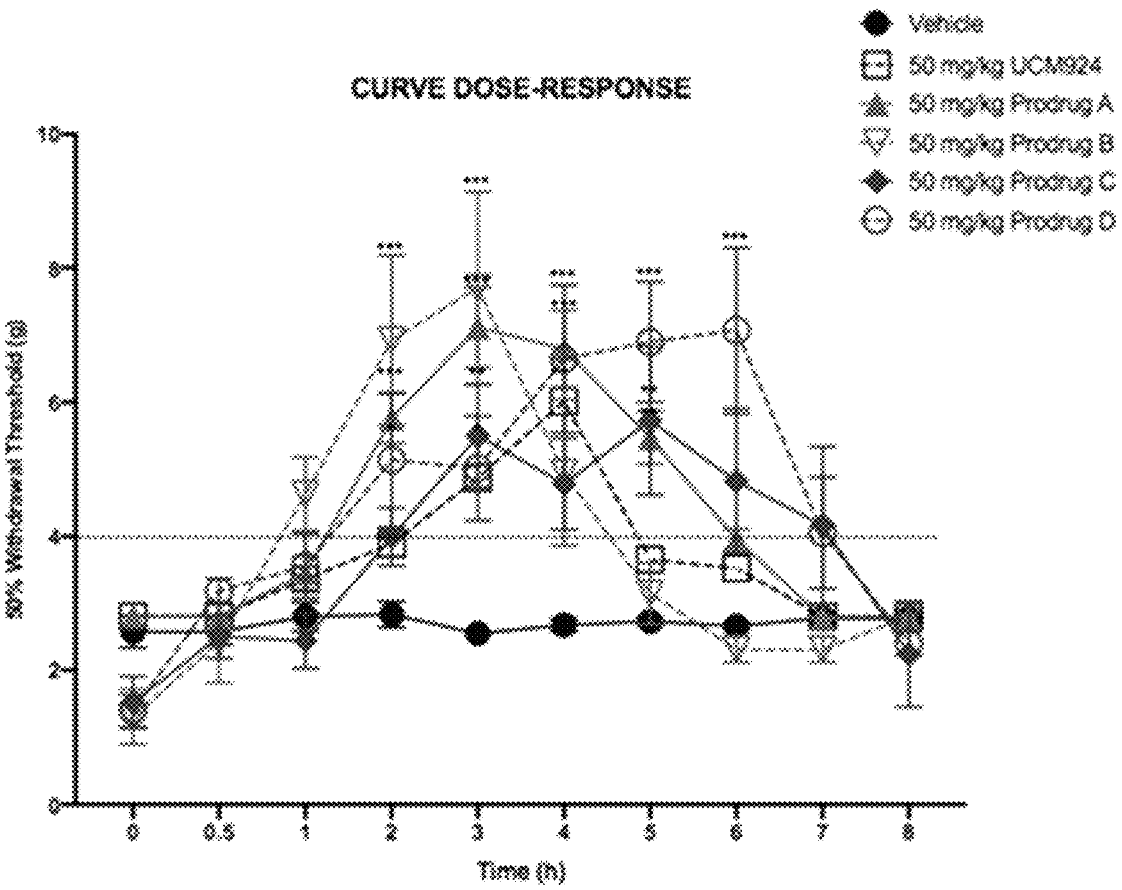
FIGS. 1A and 1B show the effects of Prodrugs A, B, C and D vs. UCM924 on mechanic allodynia in neuropathic rats.

Turning now to the invention in more details, there is provided a compound of formula (I):

(I)

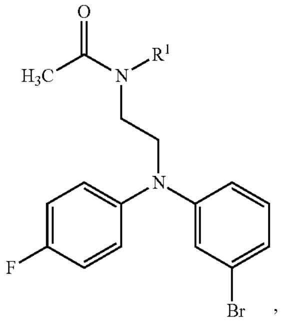

wherein:

$R^1$ is:

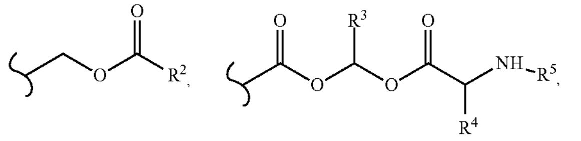

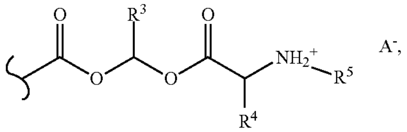

or

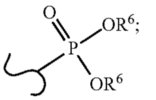

$R^2$ is an alkyl group or an —O-alkyl group;

$R^3$ is H or $CH_3$;

$R^4$ is H or a side chain of an amino acid and $R^5$ is H, or $R^4$ and $R^5$ together with the carbon atom and the nitrogen atom to which they are attached form a cyclopentyl group;

$OR^6$ represents OH, $O^-$ $Na^+$, or $O^-$ $K^+$; and

A is a pharmaceutically acceptable anion, or a pharmaceutically acceptable salt thereof.

Such compounds are melatonin $MT_2$ agonists. Indeed, the compounds of formula (I) are synthetic amino acid, ester, carbamate prodrugs of UCM924 (N-{2-[(3-bromophenyl)-(4-fluorophenyl)amino]ethyl}acetamide).

Such prodrugs are particularly useful, since it has now been found that both UCM765 and UCM924 have low oral bioavailability which are rapidly degraded by a first pass metabolism and/or plasmatic esterase, producing a bioavailability of 2% and 6%, respectively. On a positive side, these compounds are lipophilic drugs (calculated LogP of 2.64 for UCM765 and LogP 3.76 for UCM924), and their high lipophilicity led to a high brain penetrance (2.5 times more in the brain than plasma), thus making them ideal candidates for neurological and psychiatric diseases since they significantly cross the blood-brain barrier.

To overcome the problems of the low bioavailability and high lipophilicity, which confer them a low water-solubility, of previously described $MT_2$ partial agonists, the present inventors have generated novel oral prodrugs of these compounds. These prodrugs are represented by formula (I). The compounds of the invention are both oral bioavailable and water-soluble; after administration, they are converted within the body into pharmacologically active $MT_2$ partial agonists, thus generating high bioavailability of these active compounds.

As is well-known in the art, a prodrug is a poorly active or inactive compound containing a parental drug that undergoes some in vivo biotransformation through chemical or enzymatic cleavage, enabling the delivery of said parental drug at efficacious levels (Jornada, dos Santos Fernandes et al. 2015). After administration, prodrugs are converted within the body (i.e. stomach or duodenum) into the pharmacologically active parental drug.

Herein, an "alky" is a monovalent alkane radical of general formula —$CH_2$n+1. Unless otherwise specified, the alkyl groups can be linear or branched. Further, unless otherwise specified, the alkyl group and/or the —O-alkyl group in $R^2$ can contain between 1 and 18 carbon atoms, more specifically between 1 and 12 carbon atoms, between 1 and 6 carbon atoms, and preferably between 1 and 4 carbon atoms.

In embodiments, $R^1$ is

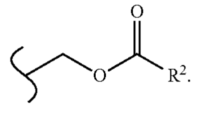

In embodiments, $R^2$ is an alkyl group. In preferred such embodiments, this alkyl group is a $C_{1-6}$ alkyl, preferably a $C_{1-4}$ alkyl, more preferably a $C_4$ alkyl, and most preferably tert-butyl.

In alternative embodiments, $R^2$ is an —O-alkyl group. In preferred such embodiments, the alkyl in the —O-alkyl group is a $C_{1-6}$ alkyl, preferably a $C_{1-4}$ alkyl, and most preferably ethyl.

In other embodiments, $R^1$ is

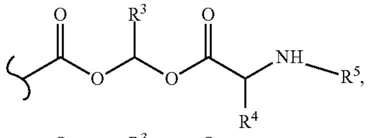

or

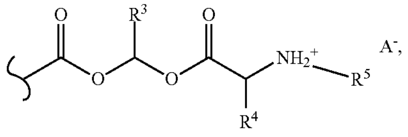

preferably

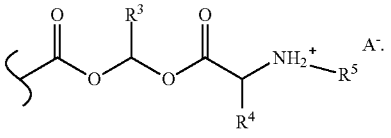

In such embodiments, the compound is thus of formula (II):

(II)

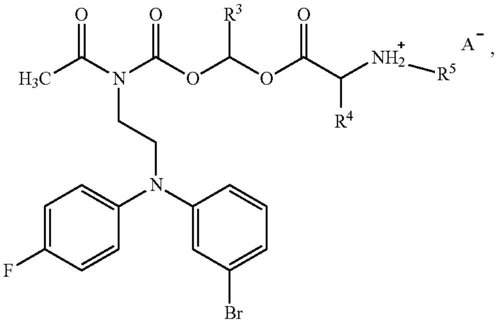

wherein $A^-$, $R^3$, $R^4$ and $R^5$ are as described above and below.

In embodiments, $R^3$ is H. In alternative embodiments, $R^3$ is $CH_3$.

Herein, the expression "$R^4$ and $R^5$ together with the carbon atom and the nitrogen atom to which they are attached form a cyclopentyl group" means that the compound is of formula (III):

(III)

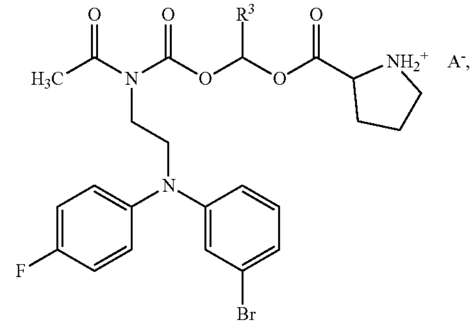

wherein $A^-$ and $R^3$ are as defined above and below.

It will be apparent to the skilled person that $R^4$ and $R^5$ are defined above to cover various amino groups. Namely, in preferred embodiments, $R^4$ and $R^5$ are as follow:

| $R^4$ | $R^5$ | Amino acid |
|---|---|---|
| $—CH_3$ | —H | Alanine |
| $—CH(CH_3)_2$ | —H | Valine |
| $—CH(CH_3)—CH_2—CH_3$ | —H | Isoleucine |
| $—CH_2—CH(CH_3)_2$ | —H | Leucine |
| $—(CH_2)_2—S—CH_3$ | —H | Methionine |
| 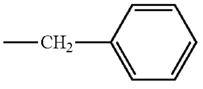 | —H | Phenylalanine |
| 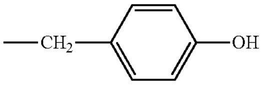 | —H | Tyrosine |
| 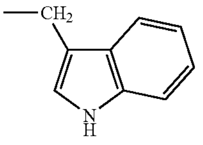 | —H | Tryptophan |
| $—CH_2—OH$ | —H | Serine |
| $—CH(OH)—CH_3$ | —H | Threonine |
| $—CH_2—C(=O)—NH_2$ | —H | Asparagine |
| $—(CH_2)_2—C(=O)—NH_2$ | —H | Glutamine |
| $—CH_2—SH$ | —H | Cysteine |
| $—CH_2—SeH$ | —H | Selenocysteine |
| —H | —H | Glycine |
| $R^4$ and $R^5$ together with the carbon atom and the nitrogen atom to which they are attached form a cyclopentyl group | | Proline |
| $—(CH_2)_3—NH—C(=NH_2^+)—NH_2$ | —H | Arginine* |
| 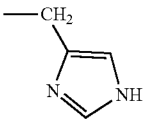 | —H | Histidine |
| $—(CH_2)_4—NH_3^+$ | —H | Lysine* |
| $—CH_2—COO—$ | —H | Aspartic Acid* |
| $—(CH_2)_2—COO$ | —H | Glutamic* |

*Shown in their ionized from found at physiological pH, neutral forms are also encompassed in the present invention.

In more preferred embodiments, $R^4$ and $R^5$ are as follow:

| $R^4$ | $R^5$ | Amino acid |
|---|---|---|
| —$CH_2$—$CH(CH_3)_2$ | —H | Leucine |
| —H | —H | Glycine |
| $R^4$ and $R^5$ together with the carbon atom and the nitrogen atom to which they are attached form a cyclopentyl group | | Proline |

In preferred embodiments, both $R^4$ and $R^5$ are H.

In most preferred embodiments, $R^3$, $R^4$ and $R^5$ are H.

Herein, a pharmaceutically acceptable anion is negatively charged ion that is pharmaceutically acceptable. Pharmaceutically acceptable anions are very well known and documented. Non-limiting examples of such anions (i.e. $A^-$ in formulas (I) to (III)) include aceglutamate, acephyllinate, acetamidobenzoate, acetate, acetylasparaginate, acetylaspartate, adipate, aminosalicylate, anhydromethylenecitrate, ascorbate, aspartate, benzoate, benzylate, besylate, bicarbonate, bisulphate, bitartrate, borate, bromide, butylbromide, camphorate, camsylate, carbonate, chloride, chlorophemoxyacetate, citrate, closylate, cromesilate, cyclamate, dehydrochloate, dihydrochloride, dimalonate, edetate, edisylate, estolate, esylate, ethylbromide, ethylsulfate, fendizoate, fluoride, formate, fosfatex, fumarate, gluceptate, gluconate, glucoronate, glutamate, glycerophosphate, glycinate, glycollylarsinilate, glycyrrhizate, hippurate, hemisulphate, hexylresorcinate, hybenzate, hydrobromide, hydrochloride, hydroiodide, hydroxybenzenesulfonate, hydroxybenzoate, iodide, isethionate, lactate, lactobionate, lysine, malate, maleate, mandalate, mesylate, methylbromide, methyliodide, methylnitrate, methylsulphate, monophosadenine, mucate, napadisylate, napsylate, nicotinate, nitrate, oleate, orotate, oxalate, oxoglurate, pamoate, pantothenate, pectinate, phenylethylbarbiturate, phosphate, picrate, policrilix, polistirex, pyridoxylphosphate, polygalacturonate, propionate, saccharinate, salicylate, stearate, stearylsulphate, subacetate, succinate, sulfate, sulfosalicylate, tannate, tartrate, teprosilate, terephthalate, teoclate, thiocyanate, timonaciate, tosylate, triethiodide, undecanoate, and xinafoate.

Preferred anions Ainclude acetate, besylate, bisulphate, bromide, carbonate, chloride, citrate, fluoride, formate, iodide, maleate, mesylate, methylsulphate, nitrate, nitrite, pamoate, phosphate, stearate, sulfate, and tartrate.

In more preferred embodiments, the anion $A^-$ is bromide, chloride, fluoride, iodide, or mesylate, preferably chloride or mesylate, and most preferably chloride.

Preferred compounds of formula (I) include the following and their pharmaceutically acceptable salts:

| Chemical Structure | Chemical name and code(s) used herein to refer to the compound |
|---|---|
| 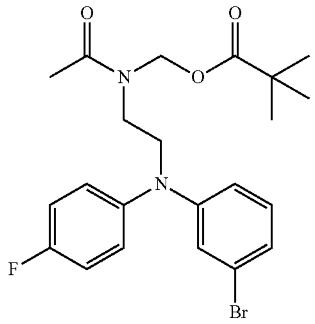 [SMILES: CC(=O)N(CCN(c1ccc(F)cc1)c1cccc(Br)c1)COC(=O)C(C)(C)C] | (N-(2-((3-bromophenyl)(4-fluorophenyl)amino)ethyl)acetamido)methyl pivalate, 4a, Prodrug A |
| 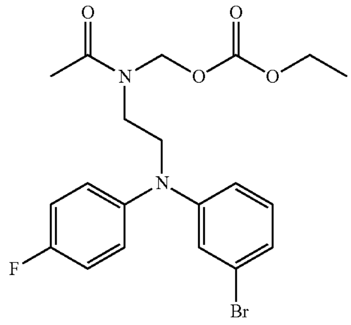 [SMILES: CCOC(=O)OCN(CCN(c1ccc(F)cc1)c1cccc(Br)c1)C(C)=O] | (N-(2-((3-bromophenyl)(4-fluorophenyl)amino)ethyl)acetamido)methyl ethyl carbonate, 4b, Prodrug B |

-continued

| Chemical Structure | Chemical name and code(s) used herein to refer to the compound |
| --- | --- |
| 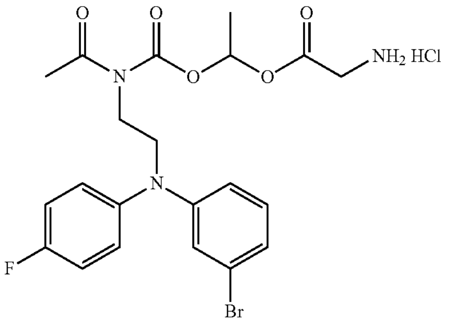 | 1-((acetyl(2-((3-bromophenyl)(4-fluorophenyl)amino)ethyl)carbamoyl)oxy)ethyl 2-aminoacetate hydrochloride, 7a, Prodrug C |
| 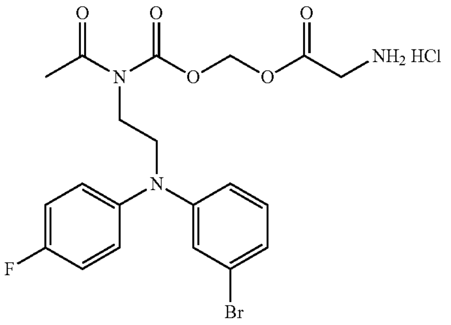 | ((acetyl(2-((3-bromophenyl)(4-fluorophenyl)amino)ethyl)carbamoyl)oxy)methyl 2-aminoacetate hydrochloride, 7b, Prodrug D |
| 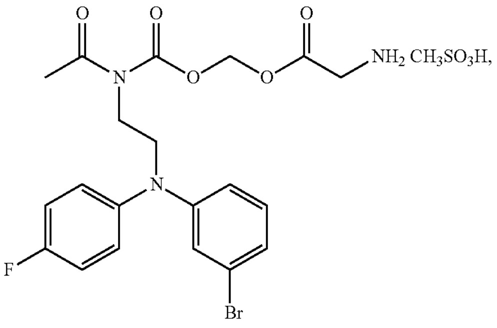 wherein the anion is replaced by a pharmaceutically acceptably anion. | ((acetyl(2-((3-bromophenyl)(4-fluorophenyl)amino)ethyl)carbamoyl)oxy)methyl 2-aminoacetate salt, 7b-2, Prodrug D-2 |
| 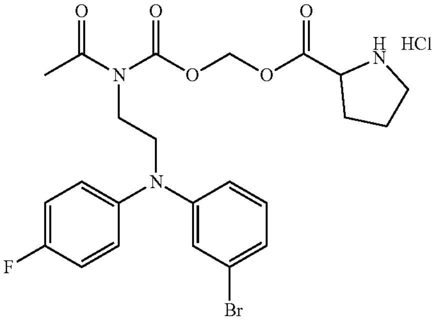 [SMILES: CC(=O)N(CCN(c1ccc(F)cc1)c1cccc(Br)c1)C(=O)OCOC(=O)C1CCCN1 ; Cl] | ((acetyl(2-((3-bromophenyl)(4-fluorophenyl)amino)ethyl)carbamoyl)oxy)methyl pyrrolidine-2-carboxylate hydrochloride, 7c, Prodrug E |

-continued

| Chemical Structure | Chemical name and code(s) used herein to refer to the compound |
|---|---|
| 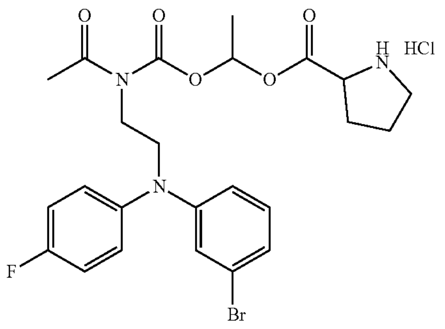 [SMILES: CC(=O)N(CCN(c1ccc(F)cc1)c1cccc(Br)c1)C(=O)OC(C)OC(=O)C1CCCN1 ; Cl] | (2S)-1-((acetyl(2-((3-bromophenyl)(4-fluorophenyl)amino)ethyl) carbamoyl)oxy)ethyl pyrrolidine-2-carboxylate hydrochloride, 7d |
| 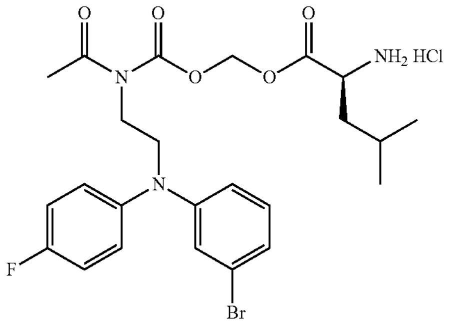 | ((S)-((acetyl(2-((3-bromophenyl)(4-fluorophenyl)amino)ethyl)carbamoyl)oxy)methyl 2-amino-4-methylpentanoate hydrochloride, 7e, Prodrug F |

It will be apparent to the skilled person that the —$NH_2HA$ (i.e., base and acid) illustrated above represent the salt from of the compounds, which can also be noted as —$NH_3^+ A^-$.

In a most preferred embodiments, the compounds of formula (I) are ((acetyl(2-((3-bromophenyl)(4-fluorophenyl)amino)ethyl)carbamoyl)oxy)methyl 2-aminoacetate hydrochloride (7b, Prodrug D) or a pharmaceutically acceptable salt thereof.

Pharmaceutical Compositions

In another aspect, there is provided a pharmaceutical composition comprising the compounds or pharmaceutically acceptable salts thereof defined herein.

Such compositions may be prepared in a manner well known in the pharmaceutical art by mixing the compounds or pharmaceutically acceptable salts thereof having a suitable degree of purity with one or more optional pharmaceutically acceptable carriers or excipients (see Remington: The Science and Practice of Pharmacy, by Loyd V Allen, Jr, 2012, 22$^{nd}$ edition, Pharmaceutical Press; Handbook of Pharmaceutical Excipients, by Rowe et al., 2012, 7th edition, Pharmaceutical Press). The carrier/excipient can be suitable for administration of the compounds or pharmaceutically acceptable salts thereof by any conventional administration route, for example, for oral, intravenous, parenteral, subcutaneous, cutaneous (dermatological), intramuscular, intracranial, intraorbital, ophthalmic, intraventricular, intracapsular, intraspinal, intrathecal, epidural, intracisternal, intraperitoneal, intranasal, or pulmonary (e.g., aerosol) administration. In an embodiment, the carrier/excipient is adapted for administration of the compounds or pharmaceutically acceptable salts thereof by the oral route.

An "excipient" as used herein has its normal meaning in the art and is any ingredient that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents, and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. Excipients are well known in the art, and the present compositions are not limited in these respects. In certain embodiments, the composition comprises one or more excipients, including for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive. Examples of commonly used excipient include water, saline, phosphate buffered saline, dextrose, glycerol, ethanol, and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives, or buffers, which increase the shelf life or effectiveness.

The compounds or pharmaceutically acceptable salts thereof described herein may be injected parenterally; this being intramuscularly, intravenously, or subcutaneously. For parenteral administration, the compounds or pharmaceutically acceptable salts thereof may be used in the form of sterile solutions containing solutes for example, sufficient saline or glucose to make the solution isotonic.

The compounds or pharmaceutically acceptable salts thereof may also be administered via transdermal routes using dermal or skin patches.

The compounds or pharmaceutically acceptable salts thereof may be administered orally in the form of tablets, coated tablets, capsules, or granules, containing suitable excipients non-limiting examples of which are starch, lactose, white sugar, and the like. The compounds or pharmaceutically acceptable salts thereof may be administered orally in the form of solutions which may contain coloring and/or flavoring agents. The compounds or pharmaceutically acceptable salts thereof may also be administered sublingually in the form of tracheas or lozenges in which the active ingredient(s) is/are mixed with sugar or corn syrups, flavoring agents, and dyes, and then dehydrated sufficiently to make the mixture suitable for pressing into solid form.

The solid oral compositions may be prepared by conventional methods of blending, granulation, compression, coating, filling, tabletting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, suspensions, syrups, or elixirs, or may be presented as a dry product for reconstitution with water alone or combined e.g., with a PEG, such as $PEG_{400}$; or other suitable vehicle before use. Such liquid preparations may or may not contain conventional additives. Non limiting examples of conventional additives include suspending agents such as sorbitol, syrup, natural gums, agar, methyl cellulose, gelatin, pectin, sodium alginate, hydroxyethyl cellulose, carboxymethylcellulose, aluminum stearate gel, or hydrogenated edible fats; emulsifying agents such as sorbitan monooleate or acacia; non-aqueous vehicles (which may include edible oils) such as almond oil, fractionated coconut oil, oily esters selected from the group consisting of glycerine, propylene glycol, ethylene glycol, and ethyl alcohol; preservatives such as for instance methyl para-hydroxybenzoate, ethyl para-hydroxybenzoate, n-propyl parahydroxybenzoate, n-butyl parahydroxybenzoate or sorbic acid; and, if desired conventional flavoring such as saccharose, glycerol, mannitol, sorbitol, or coloring agents.

For parenteral administration, fluid unit dosage forms may be prepared by utilizing the compounds or pharmaceutically acceptable salts thereof and a sterile vehicle (i.e., sterile water alone or combined e.g., with a PEG, such as $PEG_{400}$), and, depending on the concentration employed, the compounds or pharmaceutically acceptable salts thereof may be either suspended or dissolved in the vehicle. Other suitable vehicles may include olive oil, ethyl oleate, and glycols. If needed, a suitable quantity of lidocaine hydrochloride may also be included. Once in solution, the compounds or pharmaceutically acceptable salts thereof may be injected, and filter sterilized before filling a suitable vial or ampoule followed by subsequently sealing the carrier or storage package. Adjuvants, such as a local anesthetic, a preservative, or a buffering agent, may be dissolved in the vehicle prior to use. Stability of the pharmaceutical composition may be enhanced by freezing the composition after filling the vial and removing the water under vacuum (e.g., freeze drying). Parenteral suspensions may be prepared in substantially the same manner, except that the compounds or pharmaceutically acceptable salts thereof should be suspended in the vehicle rather than being dissolved, and, further, sterilization is not achievable by filtration. The compounds or pharmaceutically acceptable salts thereof may be sterilized, however, by exposing it to ethylene oxide before suspending it in the sterile vehicle. A surfactant or wetting solution may be advantageously included in the composition to facilitate uniform distribution of the compounds or pharmaceutically acceptable salts thereof.

The compounds or pharmaceutically acceptable salts thereof may be administered in the form of suppositories. Suppositories may contain pharmaceutically acceptable vehicles such as cocoa butter, polyethylene glycol, sorbitan, esters of fatty acids, lecithin, and the like.

In an embodiment of the present disclosure, the pharmaceutical composition is in the form of a unit dose or dosage form, such as an oral dosage form. The unit dose presentation forms for oral administration may be tablets, coated tablets and capsules and may contain conventional excipients. Non-limiting examples of conventional excipients include binding agents such as acacia, gelatin, sorbitol, or polyvinylpyrrolidone; fillers such as lactose, dextrose, saccharose, sugar, maize-starch, calcium phosphate, sorbitol or glycine; tabletting lubricants such as talc, stearic acid, calcium or magnesium stearate, polyethylene glycols (PEG), gums, gels; disintegrants such as starch, polyvinylpyrrolidone, sodium starch glycollate or microcrystalline cellulose; or pharmaceutically acceptable wetting agents such as sodium lauryl sulphate.

In an embodiment, the composition or unit dose comprises a saline solution. In another embodiment, the composition comprises PEG, preferably a low-molecular-weight grade PEG such as $PEG_{400}$. In an embodiment, the composition or unit dose comprises from about 10 or 20% to about 70 or 80% of PEG, for example from about 20% to about 60%, from about 30% to about 50%, or from about 35% to about 45% of PEG, preferably a low-molecular-weight grade PEG such as $PEG_{400}$. In a further embodiment, the composition or unit dose comprises about 40% of PEG, preferably a low-molecular-weight grade PEG such as $PEG_{400}$.

The above-noted composition or unit dose may be a sustained or delayed release composition or dosage form. Delayed release of the active ingredient (compounds or pharmaceutically acceptable salts thereof described herein) can be by the use of one or more release-delaying and/or release-sustaining agents. Any combination of release-delaying and/or release-sustaining agents may be used in the composition or dosage form described herein. A release-delaying agent acts to increase the period before release begins from a dosage form, and a release-sustaining agent acts increase the period of time during which the active ingredient is released from a dosage form.

The length of the lag period before delayed release occurs and the rate of release can by controlled using methods known to those of skill in the art, for instance by varying the choice, combination, form, shape and/or amount of release-delaying agent(s) and/or release-sustaining agent(s).

The delayed or sustained release formulations can be prepared, for example, by coating active ingredient or an active ingredient-containing composition with one or more release-delaying agent(s) and/or release-sustaining agent(s). In other instances, the release-delaying agent(s) and/or release-sustaining agent(s) can be intermixed with or in co-solution with the active ingredient. For example, delayed release by osmotic rupture can be achieved by a dosage form comprising one or more swelling agents that are contained in combination with the active ingredient within a semipermeable coating. The increase in volume of the swelling agent upon exposure of the unit dosage form to bodily fluids causes the semipermeable coating to rupture. In such agents, both the swelling agent and the semipermeable coating can be considered to be release-delaying agents. Thus, delayed release can be achieved by a combination of release-delaying agents, where each release-delaying agent does not necessarily delay release by itself.

Delayed release and/or sustained can be achieved by various processes such as dissolution, diffusion, erosion (e.g., based on the inherent dissolution of the agent and incorporated excipients), and/or rupture (e.g., by swelling). Common mechanisms include bulk erosion of polymers which restrict diffusion of the drug, surface erosion, (e.g., of layered medicaments), or rupture. Rupture can be osmotically controlled, for instance by swelling that results from the osmotic infusion of moisture. Rupture can also result from the reaction of effervescent agents, e.g., citric acid/sodium bicarbonate, with water or other fluids that penetrate into the dosage form. Release, including delayed release, from a unit dosage form can be achieved by more than one mechanism. For example, release can occur for example by simultaneous swelling and diffusion, simultaneous diffusion and erosion, and simultaneous swelling, diffusion, and erosion.

Two common classes of release-delaying agents are "enteric" (allowing release within a specific milieu of the gastro-intestinal tract) and "fixed-time" (allowing release after a "predetermined" or "fixed" time period after administration, regardless of gastro-intestinal milieu), each of which is discussed in more detail below. Enteric release-delaying agents for instance allow release at certain pHs or in the presence of degradative enzymes that are characteristically present in specific locations of the GI tract where release is desired. The formulation may comprise more than one release-delaying agent from any class, such as a combination of enteric and fixed-time release-delaying agents. In another embodiment, the release-delaying agent allows the release of drug after a predetermined period after the composition is brought into contact with body fluids ("fixed-time delayed release"). Unlike enteric release, fixed-time release is not particularly affected by environmental pH or enzymes.

A large number of fixed-time release-delaying agents are known to those of ordinary skill in the art. Exemplary materials which are useful for making the time-release coating of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose, cellulose acetate, cellulose acetate butyrate and ethyl cellulose; and other materials known to those of ordinary skill in the art. Other film-forming materials that can be used for this purpose include poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer. Other materials which can be used in the time-release coating include Acryl-EZER, Eudragit® NE, RL and RS, hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, and calcium pectinate can be included. Substances that are used as excipients within the pharmaceutical industry can also act as release-delaying agents.

Common types of fixed-time release dosage forms include erodible formulations, formulations that undergo osmotic rupture, or unit dosage form that use any combination of mechanisms for delayed release.

Fixed-time release-delaying agents can optionally achieve a delayed-burst release by osmotic rupture. Examples of such RDAs include swelling agents, osmogens, binders, lubricants, film formers, pore formers, coating polymers and/or plasticizers.

The release-delaying agent may comprise an "enteric" material that is designed to allow release upon exposure to a characteristic aspect of the gastrointestinal tract. In an embodiment, the enteric material is pH-sensitive and is affected by changes in pH encountered within the gastrointestinal tract (pH-sensitive release). The enteric material typically remains insoluble at gastric pH, then allows for release of the active ingredient in the higher pH environment of the downstream gastrointestinal tract (e.g., often the duodenum, or sometimes the colon). In another embodiment, the enteric material comprises enzymatically degradable polymers that are degraded by bacterial enzymes present in the lower gastrointestinal tract, particularly in the colon. Optionally, the unit dosage form is formulated with a pH-sensitive enteric material designed to result in a release within about 0-2 hours when at or above a specific pH. In various embodiments, the specific pH can for example be from about 4 to about 7, such as about 4.5, 5, 5.5, 6, 6.5 or 7.

Materials used for enteric release formulations, for example as coatings, are well known in the art and include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the trade-name Acryl-EZE® (Colorcon, USA), Eudragit® (Rohm Pharma; Westerstadt, Germany), including Eudragit® L30D-55 and L100-55 (soluble at pH 5.5 and above), Eudragit® L-IOO (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetatecrotonic acid copolymer, and ethylene-vinyl acetate copolymer; enzymatically degradable polymers such as azo polymers, pectin, chitosan, amylose and guar gum; zein and shellac. Combinations of different enteric materials may also be used. Multi-layer coatings using different polymers may also be applied. The properties, manufacture and design of enteric delivery systems are well known to those of ordinary skill in the art. See, e.g., Development of Biopharmaceutical Parenteral Dosage Forms (Drugs and the Pharmaceutical Sciences), by Bontempo (Publishers: Informa Healthcare (Jul. 25, 1997).

Use of the Compounds

The present disclosure relates to the use of the compounds or pharmaceutically acceptable salts thereof described herein (or pharmaceutical compositions comprising same) for managing or treating a disease or disorder associated with melatonin receptor activity. Melatonin and melatonin $MT_2$ receptor are known to be involved in pain (chronic pain, inflammatory pain, neuropathic pain, acute pain, post-traumatic pain), neuropsychiatric disorders including mood disorders (such as depression) and anxiety disorders, sleep, chronobiological and circadian rhythm disorders, body temperature regulation, as well as metabolic disorders such as diabetes.

Thus, in another aspect, the present disclosure relates to a method for managing or treating a disease or disorder associated with melatonin receptor activity, preferably $MT_2$ receptor activity in a subject in need thereof comprising administering to the subject an effective amount of the compounds, pharmaceutically acceptable salts thereof, or pharmaceutical compositions comprising same, described herein. The present disclosure also relates to the use of the compounds, pharmaceutically acceptable salts thereof, or pharmaceutical compositions comprising same, described herein for managing or treating a disease or disorder associated with melatonin receptor activity, preferably $MT_2$ receptor activity in a subject. The present disclosure also relates to the use of the compounds, pharmaceutically acceptable salts thereof, or pharmaceutical compositions comprising same, described herein for the manufacture of a medicament for managing or treating a disease or disorder associated with melatonin receptor activity, preferably $MT_2$ receptor activity in a subject. The present disclosure also relates to the compounds, pharmaceutically acceptable salts thereof, or pharmaceutical compositions comprising same, described herein, for use in managing or treating a disease or disorder associated with melatonin receptor activity, preferably $MT_2$ receptor activity in a subject.

In an embodiment, the disease or disorder is pain, a neuropsychiatric disorder, a sleep or chronobiological disorder, an eating disorder, hyperthermia, or a metabolic disorder.

In more specific embodiments, the present disclosure relates to a method for alleviating pain in a subject comprising administering to the subject an effective amount of the compounds, pharmaceutically acceptable salts thereof, or pharmaceutical compositions comprising same, described herein. The present disclosure also relates to the use of the compounds, pharmaceutically acceptable salts thereof, or pharmaceutical compositions comprising same, described herein for alleviating pain in a subject. The present disclosure also relates to the use of the compounds, pharmaceutically acceptable salts thereof, or pharmaceutical compositions comprising same, described herein for the manufacture of a medicament for alleviating pain in a subject. The present disclosure also relates to the compounds, pharmaceutically acceptable salts thereof, or pharmaceutical compositions comprising same, described herein for use in alleviating pain in a subject.

The pain to be alleviated or treated is chronic pain or acute pain. In an embodiment, the pain to be alleviated or treated is chronic pain. In an embodiment, the pain to be alleviated or treated is acute pain.

in an embodiment, the pain is, for example, acute tonic pain, pain relating to surgery (e.g., post-surgical pain, surgical pain), and/or pain relating to trauma (e.g., post-traumatic pain).

In another embodiment, the pain is hyperalgesia pain or allodynic pain.

In another embodiment, the pain is myalgic pain and/or inflammatory pain (e.g., pain associated with an inflammatory disease or condition), including chronic inflammatory pain.

In another embodiment the pain is neuropathic pain and/or nociceptive pain. In another embodiment, the pain is headache including tension headache, visceral pain, or pelvic pain. In a further embodiment, the nociceptive pain is visceral pain or somatic pain, for example musculo-skeletal pain or post-traumatic pain. In another embodiment, the neuropathic pain is peripheral neuropathic pain or central neuropathic pain. In a further embodiment, the pain is back pain, including low-back pain, or joint pain. In embodiments, the neuropathic pain is post-herpetic neuralgia, cancer-related pain, pain related to spinal cord injury, pain caused by reflex sympathetic dystrophy, HIV-associated pain, phantom pain, post-stroke pain, or pain caused by trigeminal neuralgia. In yet another embodiment, the pain is head pain (e.g., headache).

In another embodiment, the pain is pain associated with a disorder or condition. In an embodiment, the disorder or condition is chosen from fibromyalgia, irritable bowel syndrome, arthritis, ulcer, diabetic neuropathy, including diabetic (Type 1 or Type 2) peripheral neuropathy, sciatica, and migraine. In embodiments, the ulcer is a gastric ulcer. In another embodiment, the pain is pain associated to vulvodynia. The skilled person would understand that one or more types of pain can for example be treated and/or alleviated at the same time.

In embodiments, the present disclosure relates to a method for treating a neuropsychiatric disorder (as described in APA, DMS-V) in a subject comprising administering to the subject an effective amount of the compounds, pharmaceutically acceptable salts thereof, or pharmaceutical compositions comprising same, described herein. The present disclosure also relates to the use of the compounds, pharmaceutically acceptable salts thereof, or pharmaceutical compositions comprising same, described herein for treating a neuropsychiatric disorder in a subject. The present disclosure also relates to the use of the compounds, pharmaceutically acceptable salts thereof, or pharmaceutical compositions comprising same, described herein for the manufacture of a medicament for treating a neuropsychiatric disorder in a subject. The present disclosure also relates to the compounds, pharmaceutically acceptable salts thereof, or pharmaceutical compositions comprising same, described herein for use in treating a neuropsychiatric disorder in a subject.

Neuropsychiatric disorders include such as attention deficit disorders, cognitive deficit disorders, autism spectrum disorder, migraine headaches, addictions, eating disorders, mood disorders such as depression, and anxiety disorders (APA, DSM-V), such as generalized anxiety. In an embodiment, the neuropsychiatric disorder is a mood disorder. In a further embodiment, the mood disorder is depression, for example major depressive disorder or seasonal affective disorder (SAD). In a further embodiment, the mood disorder is an anxiety disorder. In a further embodiment, the anxiety disorder is generalized anxiety.

In another aspect, the present disclosure relates to a method for treating a sleep, chronobiological and/or circadian rhythm disorder in a subject comprising administering to the subject an effective amount of the compounds, pharmaceutically acceptable salts thereof, or pharmaceutical compositions comprising same, described herein. The present disclosure also relates to the use of the compounds, pharmaceutically acceptable salts thereof, or pharmaceutical compositions comprising same, described herein for treating a sleep, chronobiological and/or circadian rhythm disorder in a subject. The present disclosure also relates to the use of the compounds, pharmaceutically acceptable salts thereof, or pharmaceutical compositions comprising same, described herein for the manufacture of a medicament for treating a sleep, chronobiological and/or circadian rhythm disorder in a subject.

The present disclosure also relates to the compounds, pharmaceutically acceptable salts thereof, or pharmaceutical compositions comprising same, described herein for use in treating a sleep, chronobiological and/or circadian rhythm disorder in a subject. In an embodiment, the compounds, pharmaceutically acceptable salts thereof, or pharmaceutical compositions comprising same, improve the quality of sleep, sleep latency and/or daytime function.

In embodiments, the sleep, chronobiological and/or circadian rhythm disorder is a sleep disorder (such as insomnia, apnea insomnia associated to pain, narcolepsy, restless leg syndrome, parasomnias, REM sleep behavior disorder, non-24 hour sleep wake disorders, and sleep disorders associated to mental disorders), a sleep-wake disorder, or a sleep disorder associated to mental disorders (including autism spectrum disorder).

In another aspect, the present disclosure relates to a method for treating a metabolic disorder in a subject comprising administering to the subject an effective amount of the compounds, pharmaceutically acceptable salts thereof, or pharmaceutical compositions comprising same described herein. The present disclosure also relates to the use of the compounds, pharmaceutically acceptable salts thereof, or pharmaceutical compositions comprising same described herein for treating a metabolic disorder in a subject. The present disclosure also relates to the use of the compounds, pharmaceutically acceptable salts thereof, or pharmaceutical compositions comprising same described herein for the manufacture of a medicament for treating a metabolic disorder in a subject. The present disclosure also relates to the compounds, pharmaceutically acceptable salts thereof, or pharmaceutical compositions comprising same described herein for use in treating a metabolic disorder in a subject.

Examples of metabolic disorders include impaired glucose tolerance, insulin resistance and diabetes. In an embodiment, the metabolic disorder is diabetes, including type 2 or type 1 diabetes.

Any suitable amount of the compounds, pharmaceutically acceptable salts thereof, or pharmaceutical compositions may be administered to a subject. The dosages will depend on many factors including the mode of administration. Typically, the amount of the compounds, pharmaceutically acceptable salts thereof, or pharmaceutical compositions contained within a single dose will be an amount that effectively prevent, delay, or treat the above-noted diseases or disorders without inducing significant toxicity.

For the prevention, treatment or reduction in the severity of a given disease or disorder, the appropriate dosage of the compounds, pharmaceutically acceptable salts thereof, or pharmaceutical compositions will depend on the type of disease or condition to be treated, the severity and course of the disease or condition, whether the compound/composition is administered for preventive or therapeutic purposes, previous therapy, the patient's clinical history and response to the compounds, pharmaceutically acceptable salts thereof, or pharmaceutical compositions, and the discretion of the attending physician. The compounds, pharmaceutically acceptable salts thereof, or pharmaceutical compositions is suitably administered to the patient at one time or over a series of treatments.

Preferably, it is desirable to determine the dose-response curve in vitro, and then in useful animal models prior to testing in humans. The present disclosure provides dosages for the compounds, pharmaceutically acceptable salts thereof, or pharmaceutical compositions comprising same. For example, depending on the type and severity of the disease, about 1 μg/kg to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

These are simply guidelines since the actual dose must be carefully selected and titrated by the attending physician based upon clinical factors unique to each patient or by a nutritionist. The optimal daily dose will be determined by methods known in the art and will be influenced by factors such as the age of the patient and other clinically relevant factors. In addition, patients may be taking medications for other diseases or conditions. The other medications may be continued during the time that the compounds, pharmaceutically acceptable salts thereof, or pharmaceutical compositions is given to the patient, but it is particularly advisable in such cases to begin with low doses to determine if adverse side effects are experienced.

In an embodiment, the above-mentioned treatment comprises the use/administration of more than one (i.e., a combination of) active/therapeutic agent, one of which being the above-mentioned compounds or pharmaceutically acceptable salts thereof. The combination of prophylactic/therapeutic agents and/or compositions of the present disclosure may be administered or co-administered (e.g., consecutively, simultaneously, at different times) in any conventional dosage form. Co-administration in the context of the present disclosure refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more compounds or pharmaceutically acceptable salts thereof described herein is used/administered in combination with one or more agent(s) currently used to prevent or treat the disorder in question.

Manufacture of the Compounds of the Invention

The compounds of the invention can be manufactured from UCM924 by two pathways depending on the nature of $R^1$.

Reaction Scheme A

In embodiments, there is provided a method of manufacture of a compound of formula (II)

(II)

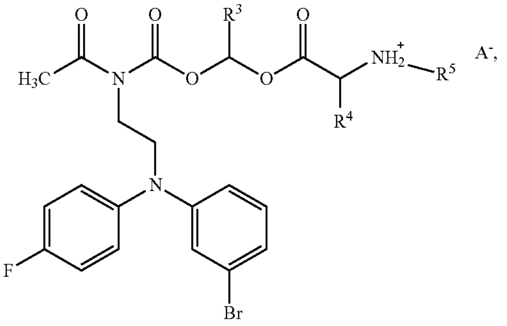

wherein $A^-$, $R^3$, $R^4$ and $R^5$ are as described above, the method comprising the steps of:

1. providing N-{2-[(-[(3-bromophenyl)-(4-fluorophenyl)amino]ethyl}acetamide (UCM924):

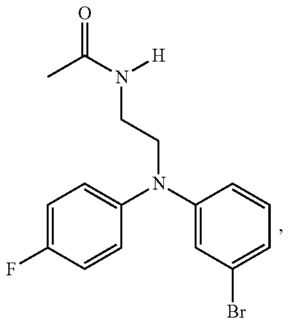

UCM 924

2. reacting UCM924 with a first base and a reactant of formula (IV) to produce a chloromethyl intermediate of formula (V):

(IV)

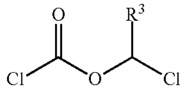

(V)

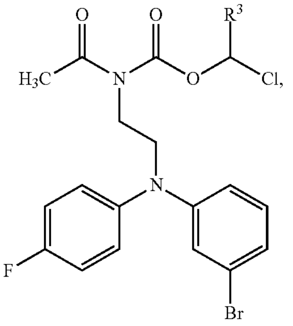

wherein $R^3$ is as defined above;

3. reacting the chloromethyl intermediate of formula (V) with a second base and a reactant of formula (VI) to produce a protected compound of formula (VII):

(VI)

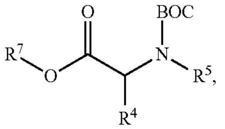

(VII)

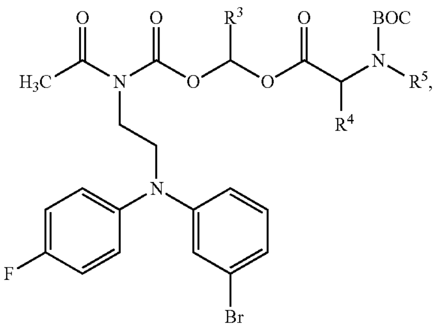

wherein $R^4$ and $R^5$ as described above, $R_7$ represents H, Li, Na, K, Cs, or Ag, and BOC represents a tert-butyloxycarbonyl protecting group; and 4. reacting the protected compound of formula (VII) with an acid of formula $H^+$ $E^-$, to produce a salt of formula (VIII):

(VIII)

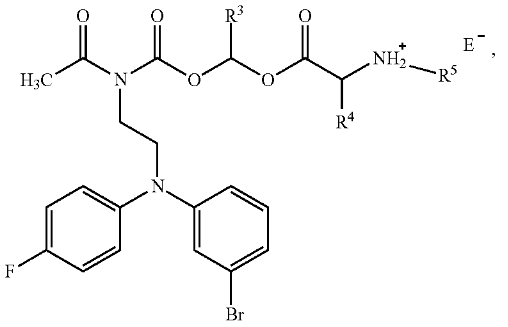

wherein $E^-$ is an anion, and 5. when $E^-$ is not a pharmaceutically acceptable anion, performing a salt metathesis to replace $E^-$ with a pharmaceutically acceptable anion ($A^-$), thus producing the compound of formula (II).

Step 1

In preferred embodiments, in step 1, UCM924 is manufactured according to the method described in the next section.

In alternative embodiments, UCM924 is manufactured according to methods described in the art, which are known to the skilled person, such as those described in (WO2014/117253A1, WO2015021535A1, Rivara, Vacondio et al. 2009, incorporated herein by reference).

Step 2

In preferred embodiments, the first base is a base of an alkaline metal, preferably lithium bis(trimethylsilyl)amide (LiHMDS), sodium bis(trimethylsilyl)amide, or lithium diisopropylamide (LDA). In more preferred embodiments, the first base is lithium bis(trimethylsilyl)amide (LiHMDS).

In preferred embodiments, step 2 comprises:

2' preparing a reaction mixture comprising UCM924 and the first base,

2" allowing UCM924 and the first base to react and produce an intermediate of formula (IX):

(IX)

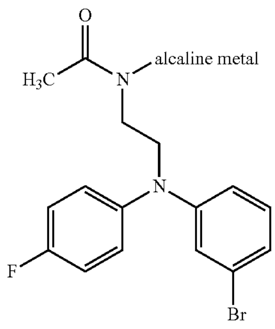

, and

2"' reacting the intermediate of formula (IX) with the reactant of formula (IV) to produce a chloromethyl intermediate of formula (V).

In preferred embodiments, at step 2", the UCM924 and the first base are allowed to react for about 10 minutes to about 24 h, preferably for about 1 h to about 5 h, more preferably for about 1 h to about 3 h, and most preferably for about 120 minutes, before step 2". Note that a stronger base will react faster than a weaker base, thus impacting the reaction time.

In preferred embodiments, step 2" comprises adding a solution of the reactant of formula (IV), preferably in the first solvent, dropwise to the reaction mixture, preferably in about 10 minutes to about 10 h, more preferably in about 30 minutes to about 3 h, and most preferably in about 60 minutes to about 90 minutes. Note that it will be longer to add a larger amount of reactant of formula (IV).

In preferred embodiments, the reaction in step 2"' is allowed to continue for about 0.5 h to about 24 h, preferably for about 0.5 h to about 3 h, more preferably for about 90 to 120 minutes, and most preferably for about 120 minutes, after the reactant of formula (IV) is added.

In preferred embodiments, step 2 is carried out in tetrahydrofuran, 2-methyltetrahydrofuran, diethyl ether, tert-butyl methyl ether, 1,4-dioxane, toluene, dimethoxyethane, benzene, or a mixture thereof, preferably in tetrahydrofuran as a first solvent.

In preferred embodiments, step 2 is carried out in the presence of the first base in about the stoichiometric amount for the reaction. Thus, in more preferred embodiments, the quantity of first base used about 1.05 times the stoichiometric amount for the reaction. In embodiments, the concentration of the first base during step 2 is 1M.

In preferred embodiments, step 2 is carried out in the presence of an excess of the reactant of formula (IV). Thus, in more preferred embodiments, the quantity of reactant of formula (IV) used is about 1 to about 10 times, preferably about to about 5 times, preferably about 2 times the stoichiometric amount for the reaction.

Step 2 is typically carried in an anhydrous atmosphere. In preferred embodiments, step 2 is carried out in an inert atmosphere, preferably in argon.

In preferred embodiments, step 2 is carried out at a temperature of about −10° C. to about 23° C., preferably about 0° C. to about 10° C., and more preferably at a temperature of about 5° C. Such temperature can be achieved with an ice bath.

In preferred embodiments, the method further comprises the step of isolating, and preferably purifying, the chloromethyl intermediate of formula (V) before step 3.

Step 3

In preferred embodiments, $R_7$ is H.

In preferred embodiments, the second base is $Cs_2CO_3$, triethylamine, CsCl, tert-butyl-OK, tert-butyl-ONa, methyl-ONa, $Cs_2CO_3$, $Na_2CO_3$, $K_2CO_3$, $NaHCO_3$, $KHCO_3$, NaH, KH, LiOH, NaOH, CsOH, or KOH, preferably a base of a monovalent metal. In preferred embodiments, the second base is KOH. Among all the other bases, KOH unexpectedly yields a product with a higher purity in a higher yield.

In preferred embodiments in which the second base is a base of a monovalent metal (e.g., Li, K, Na, Cs), step 3 can comprise:

3' preparing a reaction mixture comprising the reactant of formula (VI) wherein $R_7$ is H, and the second base, 3" allowing the reactant of formula (VI) and the second base to react and produce a reactant of formula (X):

(X)

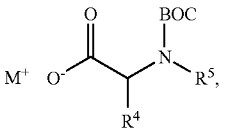

wherein $M^+$ is a monovalent metal cation (i.e., a reactant of formula (VI) wherein $R_7$ is not H), and 3"' reacting the intermediate of formula (IX) with the reactant of formula (X) to produce a protected compound of formula (VII).

This sequence for combining the various reactant unexpectedly reduced the generation of undesired UCM924. When using KOH, extremely high yields and purity are obtained (>90% yield, <10% starting material remaining).

Examples of monovalent metal cations include in the reactant of formula (X) include Lit, Nat, $K^+$, and Cs+.

In preferred embodiments, at step 3", the reactant of formula (VI) and the second base are allowed to react for about 0.5 h to about 24 h, preferably for about 1 h to about 3 h, and more preferably for about 180 minutes, before step 3". Note that a stronger base will react faster than a weaker base, thus impacting the reaction time.

In preferred embodiments, step 3" comprises adding the reaction mixture obtained at step 3", preferably dropwise, to a solution of the intermediate of formula (IX), preferably in about 10 minutes to about 10 h, preferably about 20 minutes to about 60 minutes, and more preferably in about 40 minutes. Note that it will be longer to add a larger amount of reactant of reaction mixture.

In preferred embodiments, the reaction is allowed to continue for about 2 h to about 7 days, preferably for about 20 h, after the intermediate of formula (IX) is added. Note that the reaction time will depend on the monovalent metal cation—from slowest reaction to fastest reaction: $Li^+<Na^+<K^+<Cs^+$.

In preferred embodiments, step 3 is carried out in tetrahydrofuran, $CH_3CN$, dimethylformamide, preferably in dimethylformamide as a second solvent.

In alternative embodiments, the chloromethyl intermediate of formula (V) is not isolated before step 3. In preferred such embodiments, the base, the quantity of base used, and the second solvent at step 3 are the same as the base, the quantity of base used, and the first solvent at step 2.

In preferred embodiments, step 3 is carried out in the presence of an excess of the reactant of formula (VI). Thus, in more preferred embodiments, the quantity of reactant of formula (VI) used is in about 1 to about 10 times, preferably about 1 to about 5 times, yet more preferably about 2 to 4 times, and most preferably 2 times the stoichiometric amount for the reaction.

In preferred embodiments, step 3 is carried out in the presence of an excess of the second base, particularly when $R_7$ represents H. In preferred embodiments, step 3 is carried out in the presence the second base in a quantity that is 1 to 10 times, preferably about 1 to about 5 times, and more preferably about 1 to about 2 times the stoichiometric amount for the reaction, preferably about the stoichiometric amount for the reaction. Note that the quantity of second base will increase with increasing quantity of reactant of formula (VI).

Step 3 is typically carried in an anhydrous atmosphere. In preferred embodiments, step 3 is carried out in an inert atmosphere, preferably in argon.

In preferred embodiments, step 3 is carried out at a temperature of about 0° C. to about 50° C., preferably 10° C. to about 30° C., and most preferably at room temperature. Care must be taken to avoid using too high temperatures that could result in the decomposition of the starting materials.

In preferred embodiments, the method further comprises the step of isolating, and preferably purifying, the protected compound of formula (VII) before step 4.

Steps 4 and 5

In preferred embodiments, the acid in step 4 is citric acid, acetic acid, trifluoroacetic acid, phosphorous acid, phosphoric acid, formic acid, oxalic acid, nitric acid, boric acid, gluconic acid, lactic acid, tartaric acid, methanesulfonic acid, p-toluenesulfonic acid, benzenesulfonic acid, $H_2SO_4$, or HCl, preferably HCl.

In preferred embodiments, step 4 is carried out in the presence of an excess of the acid (VI). Thus, in more preferred embodiments, the quantity of reactant of formula (VI) used is about 2 to about 100 times, preferably about to about 15 times, and more preferably 10 times the stoichiometric amount for the reaction.

In preferred embodiments, step 4 is carried out in methanol, ethanol, isopropyl alcohol, diethyl ether, $CH_3CN$, tetrahydrofuran, 2-methyltetrahydrofuran, dichloromethane, acetone, chloroform, methyl tert-butyl ether, dioxane, preferably in dioxane as a third solvent.

In preferred embodiments, step 4 is carried out for about 0.5 h to about 6 h, preferably for about 0.5 h to 2.5 h, and more preferably for about 40 minutes.

In preferred embodiments, step 4 is carried out at a temperature of about −10° C. to about 50° C., preferably about 0° C. to about 30° C., preferably at a temperature of about 0° C. to room temperature, and more preferably at room temperature. Note that the product of the reaction tends to decompose at too high temperatures and that the reaction will stop working at too low temperatures.

The salt metathesis at step 5 is a common technique for exchanging counterions. The choice of reactants is guided by a solubility chart or lattice energy as known in the art.

Reaction Scheme B

In other embodiments, there is provided a method of manufacture of a compound of the invention of formula (VI):

(VI)

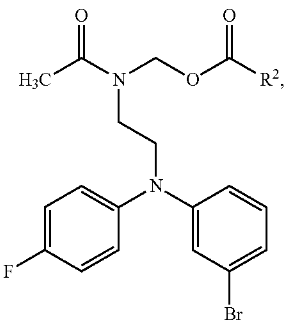

wherein $R^2$ is as described above, the method comprising the steps of:

A. providing UCM924; and

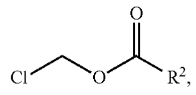

B. reacting UCM924 with wherein $R^2$ is as described above, in the presence of NaH thus producing the compound of formula (VI).

In preferred embodiments, in step A, UCM924 is manufactured according to the method described in the next section.

In preferred embodiments, step B is carried out in dimethylformamide, tetrahydrofuran, 2-methyltetrahydrofuran, dimethyl sulfoxide, dimethylacetamide, or N-methyl-2-pyrrolidone, preferably in dimethylformamide as a solvent.

In preferred embodiments, step B is carried out at a temperature between about −78° C. and about 100° C., preferably between about 0° C. and about 30° C., and more preferably at room temperature.

In preferred embodiments, step B is carried out for about 1 h to about 48 h, preferably for about 3 h to 24 h, and more preferably for about 3 h.

Manufacture of UCM924

In another aspect of the invention, there is provided a method of manufacturing N-{2-[(-[(3-bromophenyl)-(4-fluorophenyl)amino]ethyl}acetamide (UCM924):

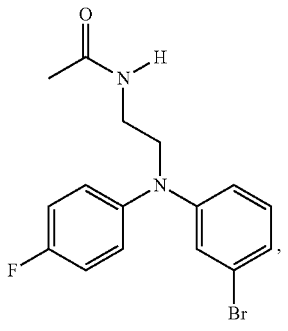

UCM 924 the method comprising the steps of:

i) reacting 3-bromoaniline

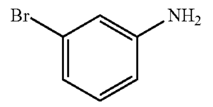

with 1-fluoro-4-iodobenzene

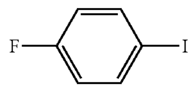

to produce 3-bromo-N-(4-fluorophenyl)aniline:

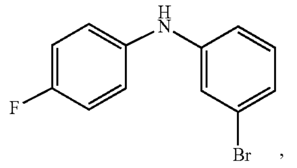 [SMILES: Fc1ccc(Nc2cccc(Br)c2)cc1]

ii) salifying the 3-bromo-N-(4-fluorophenyl)aniline to produce a 3-bromo-N-(4-fluorophenyl)aniline salt, and isolating said salt as a solid, and iii) reacting the 3-bromo-N-(4-fluorophenyl)aniline salt with N-(2,2-dimethoxyethyl)acetamide

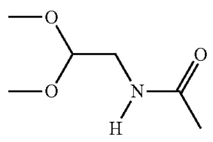

to produce UCM924.

Unexpectedly, step ii) allows to obtain UCM924 at step iii):

at large scales (e.g., >100 mmol)

in a high yield, especially when using only recrystallization for isolating the UCM924, and in a shorter time.

Indeed, according to the results reported in Table 4 below, it can be seen that:

without step ii) and at smaller scales (<50 mmol, entries 1, 2 and 4), relatively high UCM924 yields (80-90%) can be obtained in 2 to 4 h, but it is necessary to perform a recrystallization (yields 70-80%) followed by flash column chromatography (yield 7-12%) to arrive at those results;

without step ii) and at larger scales (180 mmol, entry 5), a similar highUCM924 yield (87%) is obtained, but it takes longer (6 h) and it is even more necessary to perform a recrystallization (yield 61.8% only) followed by flash column chromatography (yield 20.6%) to arrive at those results; and with step ii), at larger scales (140 mmol, entry 7), a similarhighUCM924 yield is obtained (85%) in less than 4 h and it is NOT necessary to perform flash column chromatography, since a yield of 85% is obtained by using recrystallization only.

In preferred embodiments, the 3-bromoaniline and the 1-fluoro-4-iodobenzene are reacted at step i) in one or more, preferably all of, the following conditions:

in the presence of an excess of 1-fluoro-4-iodobenzene, preferably in an amount of about 1 to about 5 times, preferably about 1 to about 2 times the stoichiometric amount, and more preferably in an amount of about 1.05 times the stoichiometric amount, in the presence of a palladium catalyst; such as palladium pivalate, palladium(ii) bromide, palladium(ii) acetylacetonate, palladium(ii) iodide, palladium(ii) trifluoroacetate, palladium(ii) propionate, palladium(ii) chloride, dichlorobis(triethylphosphine) palladium(ii), palladium(ii) hexafluoroacetylacetonate, tetrakis(triphenylphosphine) palladium(0), bis(triphenylphosphine) palladium(ii) dichloride, bis(dibenzylideneacetone)palladium(0), dichlorobis(tricyclohexylphosphine) palladium(ii), dichloro(1,5-cyclooctadiene) palladium(ii), bis(dibenzylideneacetone)palladium(0), or palladium (II) acetate ($Pd(OAc)_2$), preferably $Pd(OAc)_2$, preferably in an amount of at least 0.04 times the stoichiometric amount, for example, the catalyst can be at a concentration of about 0.1 mol % to about 10 mol %, preferably of about 1 mmol % to about 5 mmol %.

in the presence of a ligand, preferably a phosphine ligand, more preferably triphenylphosphine, XPhos (dicyclohexyl [2',4',6'-tris(propan-2-yl) [1,1'-biphenyl]-2-yl] phosphane), Xantphos (4,5-bis(diphenylphosphino)-9, 9-dimethylxanthene), 1,1'-bis(diphenylphosphino) ferrocene (DPPF), RuPhos (2-dicyclohexylphosphino-2',6'-diisopropoxybiphenyl), SPhos (dicyclohexyl(2',6'-dimethoxy [1,1'-biphenyl]-2-yl)phosphane), tricyclohexylphosphine, BrettPhos (2-(dicyclohexylphosphino) 3,6-dimethoxy-2',4',6'-triisopropyl-1,1'-biphenyl), JohnPhos ((2-biphenylyl) di-tert-butylphosphine, 2-(di-tert-butylphosphino) biphenyl, (2-biphenyl)di-tert-butylphosphine), tBuXPhos (2-di-tert-butylphosphino-2',4',6'-triisopropylbiphenyl), DavePhos (2-dicyclohexylphosphino-2'-(N,N-dimethylamino) biphenyl), or 2,2'-bis (diphenylphosphino)-1,1'-binaphthyl (BINAP), more preferably, 2'-bis(diphenylphosphino)-1,1'-binaphthyl (BINAP); preferably in an amount of at least 0.05 times the stoichiometric amount, in the presence of a base, preferably $Na_2CO_3$, $K_2CO_3$, $Cs_2CO_3$, KF, sodium tert-butoxide, KOH, NaOH, $K_3PO_4$, or potassium tert-butoxide, more preferably potassium tert-butoxide, preferably in excess, more preferably in an amount of about 1 to about 5 times, preferably 1.2 to 2 times the stoichiometric amount, and yet more preferably in an amount of about 1.5 times the stoichiometric amount, in a solvent, preferably dioxane, tetrahydrofuran, 2-methyltetrahydrofuran, or toluene, more preferably toluene, preferably in a concentration of about 0.1M to about 1M, preferably about 0.25M to about 0.75M, and most preferably at a concentration of about 0.5M, at a temperature of about 50° C. to about 120° C., preferably about 50° C. to about 120° C., and more preferably at a temperature of 100° C., for about 1 h to about 48 h, preferably 4 h to about 10 h, and more preferably for about 4 h to about 6 h, and/or (preferably and)

under an inert atmosphere, preferably argon or nitrogen.

In preferred embodiments, step i) comprises preparing a solution of the 3-bromoaniline, the 1-fluoro-4-iodobenzene, the ligand, and the catalyst in the solvent, preferably stirring the solution for about 10 minutes to about 60 minutes (more preferably 30 minutes), and then adding the base to the solution.

In preferred embodiments, the 3-bromo-N-(4-fluorophenyl)aniline are salified at step ii) in one or more, preferably all of, the following conditions:

- with an acid such as $H_2SO_4$, formic acid, or HCl, preferably HCl; preferably in excess, more preferably in an amount of about 1 to about 10 times, preferably about 1 to about 2 times the stoichiometric amount, and yet more preferably in an amount of about 1.5 times the stoichiometric amount,
- in a solvent, preferably diethyl ether, tert-butyl methyl ether, ethyl acetate, or dioxane, and more preferably dioxane,
- at a temperature of about 0° C. to about 30° C., preferably at room temperature, and/or (preferably and)·
- for about 30 minutes to about 24 h, preferably for about 1 h to about 5 h, more preferably for about 2 h.

In preferred embodiments, the 3-bromo-N-(4-fluorophenyl)aniline is salified with HCl at step ii). In such embodiments, the 3-bromo-N-(4-fluorophenyl)aniline salt is a HCl salt, also called 3-bromo-N-(4-fluorophenyl)benzene-aminium chloride.

The isolation of the 3-bromo-N-(4-fluorophenyl)aniline salt at step ii) can be carried out by any means known in the art.

Step iii) can be carried out as known in the art, for example, using the method reported in Righi, M.; Bedini, A.; Piersanti, G.; Romagnoli, F.; Spadoni, G.; *J. Org. Chem.* 2011, 76, 704, incorporated herein by reference. In preferred embodiments, the 3-bromo-N-(4-fluorophenyl)aniline salt and the N-(2,2-dimethoxyethyl)acetamide are reacted at step iii) in one or more, preferably all of, the following conditions:

- in the presence of N-(2,2-dimethoxyethyl)acetamide, preferably in excess, more preferably in an amount of about 1 to about 3 times the stoichiometric amount, and even more preferably in an amount of about 1.4 times the stoichiometric amount,
- in the presence trifluoroacetic acid; preferably in excess, more preferably in an amount of about 1 to about times, yet more preferably about 1 to about 6 times the stoichiometric amount, and even more preferably in an amount of about 3 to about 4 times the stoichiometric amount,
- in the presence of triethylsilane, preferably in excess, more preferably in an amount of about 1 to about 5 times, yet more about 2 to about 4 times the stoichiometric amount, and even more preferably in an amount of 2.5 times the stoichiometric amount,
- in a solvent, preferably chloroform, tetrahydrofuran, 2-methyltetrahydrofuran, diethyl ether, 1,2-dichloroethane, dichloromethane, and more preferably dichloromethane,
- at a temperature of about-10° C. to about 50° C., preferably about 0° C. to about 30° C., and more preferably at room temperature, and/or (preferably and)
- for about 1 h to about 24 h, preferably about 2 to about 10 h, and more preferably for about 3.5 h.

In preferred embodiments, step iii) comprises the step of combining the 3-bromo-N-(4-fluorophenyl)aniline salt, the N-(2,2-dimethoxyethyl)acetamide, the trifluoroacetic acid, and the triethylsilane at a temperature of about −10° C. to about 10° C., preferably at about 0° C., for about 5 minutes to about 30 minutes, preferably for about 10 minutes, and before performing the reaction as noted above.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted. In contrast, the phrase "consisting of" excludes any unspecified element, step, ingredient, or the like. The phrase "consisting essentially of" limits the scope to the specified materials or steps and those that do not materially affect the basic and novel characteristic(s) of the invention.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure, such as Formulas I to III, with various substituents ($R_1$, $R_2$, etc.) and various radicals (alkyl, halogen atom, etc.) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present disclosure will become more apparent upon reading of the following non-restrictive description of specific embodiments thereof, given by way of example only with reference to the accompanying drawings.

Description of Illustrative Embodiments

The present disclosure is illustrated in further details by the following non-limiting examples.

Example 1—Synthesis of UMC924

UMC924 was synthesized according to the following reaction scheme.

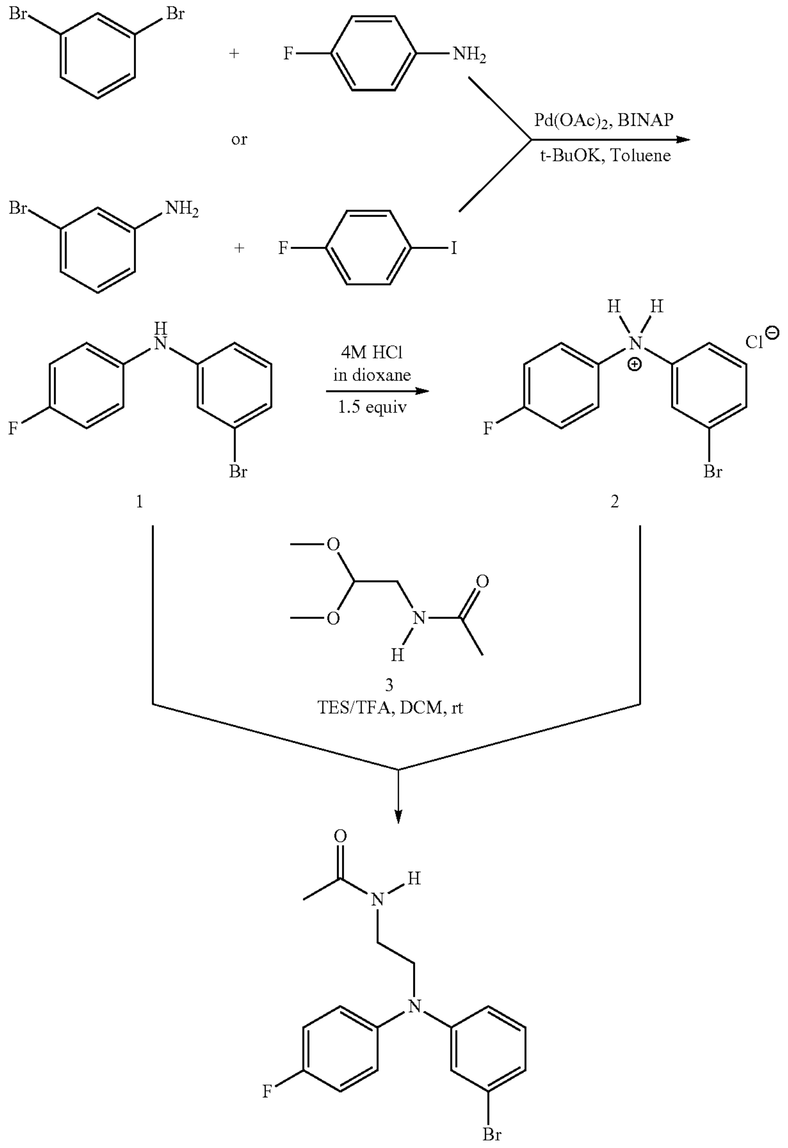

UCM 924

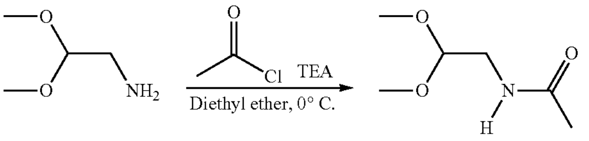

3

Namely, intermediate compound 3-bromo-N-(4-fluorophenyl)aniline1 was synthesized, optionally salified, and then reacted with intermediate N-(2,2-dimethoxyethyl)acetamide 3

Synthesis of Intermediate 3-bromo-N-(4-fluorophenyl)aniline 1

The synthesis of intermediate 1 was improved in the following fashion.

A first serie of synthesis reactions was carried out in the conditions reported in Rivara, S.; Vacondio, F.; Fioni, A.; Silva, C.; Carmi, C.; Mor, M.; Lucini, V.; Pannacci, M.; Caronno, A.; Scaglione, F.; Gobbi, G.; Spadoni, G.; Bedini, A.; Orlando, P.; Lucarini, S.; Tarzia, G. *ChemMedChem* 2009, 4, 1746.

The reaction scheme was:

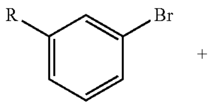

1.0 equiv

-continued

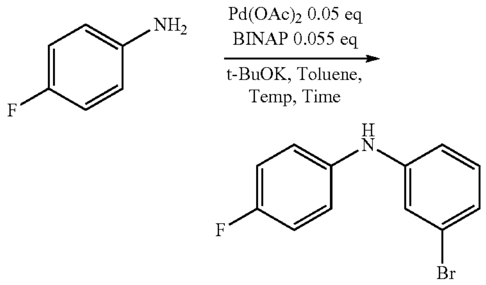

The conditions used and the results were as reported in Table 1.

TABLE 1

Conditions and results of the first series of synthesis reactions for intermediate 1

| Entry | R | 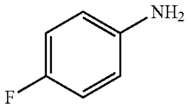 /eq | t-BuOK/ eq | Temp/° C. | Time/h | Yield % | Scale mmol |
|---|---|---|---|---|---|---|---|
| 1 | Br | 1.2 | 1.4 | 100 | 4 | 38 | 5 |
| 2 | Br | 0.5 | 1.5 | 90 | overnight | 37 | 25 |
| 3 | Br | 1.2 | 1.5 | 80 | overnight | 53 | 50 |
| 4 | Br | 1.2 | 1.5 | 80 | 24 | 60.5 | 200 |
| 5 | I | 1.0 | 1.5 | 110 | 6 | 35 | 50 |
| 6 | I | 1.0 | 1.5 | 60 | 24 | ND | 50 |
| 7 | I | 1.2 | 1.5 | 80 | 24 | 32 | 50 |

t-BuOK = potassium tert-butoxide, ND = not determined

Entry 4 reported in Table1 had the highest yield. For this entry, the reaction scheme and protocol were as follows.

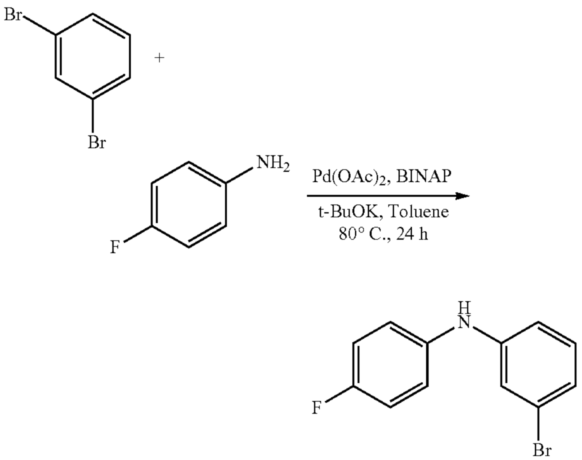

In dry and degassed toluene (500 ml) were sequentially added 1,3-Dibromobenzene (25 ml, 200 mmol, 1 equiv), 4-Fluoroaniline (23 ml, 240 mmol, 1.2 equiv), $Pd(OAc)_2$ (2.24 g, 10 mmol, 0.05 equiv), BINAP (6.84 g, 10 mmol, 0.05 equiv) and t-BuOK (34.4 g, 300 mmol, 1.5 equiv). The reaction was left stirring for 24 hours at 80° C. (Bath temperature) under argon. After cooling to rt, the mixture was filtered through a short pad of Celite to remove the insoluble impurity and washed with 20% EtOAc in Hexane. The organic solvents were evaporated under vacuum and flash column chromatography with 5% EtOAc in Hexane to give the desired product 32.2 g as brown oil in 60.5% yield with around 95% purity.

A second series of synthesis reactions were carried out according to the following reactions scheme and in the conditions reported in Table2.

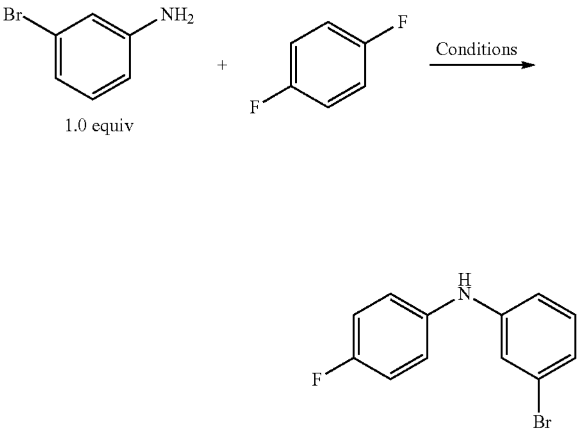

TABLE 2

Conditions and results of the second series of synthesis reactions for intermediate 1

| Entry | /eq | Base/eq | Solvent/ Conc. | Temp/ ° C. | Time/h | Yield % | Scale mmol |
|---|---|---|---|---|---|---|---|
| 1 | 1.0 | t-BuOK/1.0 | DMSO/2M | rt + 90 | 2 + 18 | decomposed | 10 |
| 2 | 1.0 | t-BuOK/1.0 | DMSO/2M | rt | 16 | No reaction | 10 |
| 3 | 1.0 | t-BuOK/1.0 | Toluene/1M | rt | 16 | No reaction | 1 |
| 4 | 1.0 | t-BuOK/1.0 | Dioxane/1M | rt | 16 | No reaction | 1 |
| 5 | 1.0 | t-BuOK/1.0 | THF/1M | rt | 16 | No reaction | 1 |

TABLE 2-continued

Conditions and results of the second series of synthesis reactions for intermediate 1

| Entry | /eq | Base/eq | Solvent/ Conc. | Temp/ ° C. | Time/h | Yield % | Scale mmol |
|---|---|---|---|---|---|---|---|
| 6 | 1.0 | t-BuOK/1.0 | DMF/1M | rt | 16 | No reaction | 1 |
| 7 | 1.0 | NaH/1.0 | DMSO/1M | rt + 90 | 1.5 + 1 | No reaction | 1 |
| 8 | 1.0 | NaH/1.0 | THF/1M | rt | 1.5 | No reaction | 1 |
| 9 | 10 | t-BuOK/2.0 | neat | 90 | 24 | No reaction | 1 |
| 10 | 10 | t-BuOK/2.0 | DMSO/1M | 90 | 24 | 21 | 1 |

t-BuOK = potassium tert-butoxide;
THF = tetrahydrofuran;
DMSO = dimethyl sulfoxide;
rt = room temperature Then, a third series of synthesis reactions were carried out according to the following reactions scheme and in the conditions reported in Table 3.

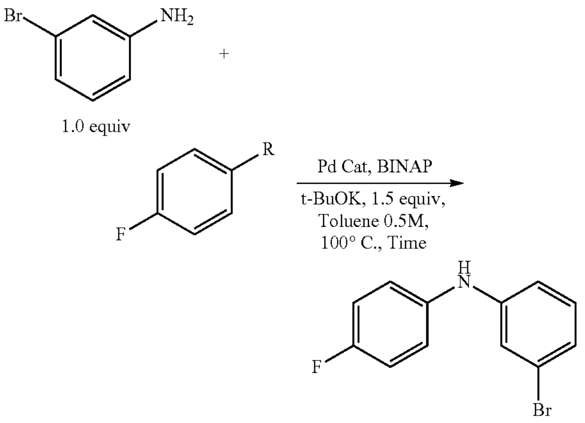

TABLE 3

Conditions and results of the third series of synthesis reactions for intermediate 1

| Entry | R/eq | Cat./eq | Ligand/eq | Time/h | Yield % | Scale mmol |
|---|---|---|---|---|---|---|
| 1 | I/1.0 | $Pd(OAc)_2$/0.025 | BINAP/0.025 | 4 | trace | 10 |
| 2 | Br/1.0 | $Pd(OAc)_2$/0.025 | BINAP/0.025 | 4 | trace | 10 |
| 3 | I/1.0 | $Pd(OAc)_2$/0.050 | BINAP/0.050 | 4 | 83 | 1 |
| 4 | I/1.0 | $Pd(PPh_3)_4$/0.050 | BINAP/0.050 | 4 | trace | 1 |
| 5 | I/1.0 | $Pd(dba)_2$/0.050 | BINAP/0.050 | 4 | 56 | 1 |
| 6 | I/1.0 | $Pd_2(dba)_3$/0.050 | BINAP/0.050 | 4 | 63 | 1 |
| 7 | I/1.0 | $PdCl_2$/0.050 | BINAP/0.050 | 4 | trace | 1 |
| 8 | I/1.0 | $Pd(OAc)_2$/0.025 | BINAP/0.025 | 4 | trace | 1 |
| | | | | 24 | 11 | |
| 9 | I/1.2 | $Pd(OAc)_2$/0.025 | BINAP/0.025 | 4 | trace | 1 |
| | | | | 24 | ND | |
| 10 | I/1.2 | $Pd(OAc)_2$/0.010 | BINAP/0.010 | 4 | 0 | 1 |
| | | | | 24 | trace | |
| 11 | I/1.0 | $Pd(OAc)_2$/0.05 | BINAP/0.05 | 6 | 70 | 10 |
| 12 | I/1.0 | $Pd(OAc)_2$/0.04 | BINAP/0.05 | 6 | 82 | 10 |
| 13 | I/1.05 | $Pd(OAc)_2$/0.04 | BINAP/0.05 | 6 | 71 | 100 |

Cat. = catalyst;
$Pd(OAc)_2$ = palladium (II) acetate;
$Pd(PPh_3)_4$ = tetrakis(triphenylphosphine)palladium(0);
$Pd(dba)_2$ = bis(dibenzylideneacetone)palladium(0);
$Pd_2(dba)_3$ = tris(dibenzylideneacetone)dipalladium(0);
BINAP = (2,2'-bis(diphenylphosphino)-1,1'-binaphthyl)

For Entry 13 reported in Table 3, the reaction scheme and protocol were as follow.

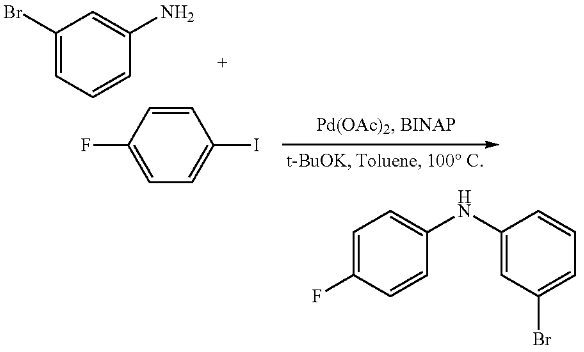

In an oven-dried flask and under argon atmosphere, a mixture of 3-Bromoaniline (11.1 ml, 100 mmol, 1 equiv, 98%), 4-Fluoroiodobenzene (12.11 ml, 105 mmol, 1.05 equiv, 99%), rac-BINAP (3.11 g, 5 mmol, 0.05 equiv, 97%)

and $Pd(OAc)_2$ (900 mg, 4 mmol, 0.04 equiv, 98%) was dissolved in dry and degassed toluene (200 mL) and the mixture was stirred for 30 mins at room temperature. Then KOtBu (16.83 g, 150 mmol, 1.5 equiv, 98%) was added and the mixture was heated to 100° C. for 6 h. After cooling to rt, the mixture was filtered through a short pad of Celite to remove the insoluble impurity and washed with 20% EtOAc in Hexane. The organic solvents were evaporated under vacuum, the residue was purified by Flash Column Chromatography ($SiO_2$, 0-5% EtOAc in Hexane) to give the desired product 19 g as brown oil in 71% yield.

This procedure has also successfully been used for 1 to 5 Kg scale syntheses.

$^1H$ NMR (600 MHz, Acetone-d6): δ 7.54 (s, 1H), 7.21 (dd, J=8.8, 4.7 Hz, 2H), 7.19-7.12 (m, 2H), 7.11-7.09 (m, 2H), 7.01 (dd, J=8.2, 1.7 Hz, 1H), 6.96 (dd, J=7.9, 1.7 Hz, 1H).

Synthesis of 3-bromo-N-(4-fluorophenyl)aniline HCl salt 2

The salt of intermediate 1, 3-bromo-N-(4-fluorophenyl) aniline HCl salt 2, was produced as follows.

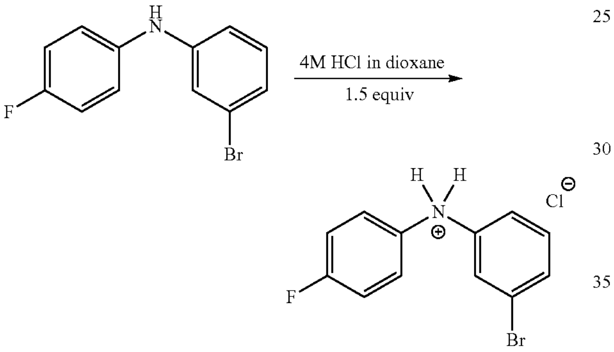

Treatment of 107 g of 3-bromo-N-(4-fluorophenyl)aniline (70-80% purity) with 1.5 equiv of HCl (4 M in dioxane) and kept stirring at rt for 2 hours (at least 2 hours, 30 mins to overnight was tested by small scale) to precipitate the crude HCl salt as pale brown solid. Then dioxane was evaporated under vacuum and the residue was re-dissolved with 20% diethyl ether in hexane and kept stirring at room temperature for another 1 to 2 hours to precipitate the desired 3-bromo-N-(4-fluorophenyl)aniline HCl salt as fine white or pale brown solid (Air sensitive, it will become back to brown oil while expose to the air) which was filtrated to give the desired product 80.45 g with >99% purity.

This procedure has also successfully been used for 1 to 5 Kg scale syntheses.

$^1H$ NMR (600 MHz, DMSO-d6): δ 7.16-7.08 (m, 6H), 6.97 (d, J=8.2 Hz, 1H), 6.91 (d, J=7.8 Hz, 1H).

Synthesis of Intermediate N-(2,2-dimethoxyethyl)acetamide 3

The synthesis of intermediate 3 was carried out in the following fashion.

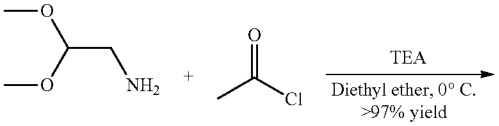

-continued

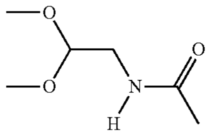

To a solution of 2,2-dimethoxyethylamine (400 mmol, 44.93 ml) and triethylamine (420 mmol, 1.05 equiv, 58.54 ml) in diethyl ether (750 ml) was slowly added dropwise acetic chloride (420 mmol, 1.05 equiv, 30 ml) at 0° C. The mixture was stirred and slowly warmed up to room temperature for 1.5 hours to complete the reaction. The mixture was filtered through a short pad of Celite® to remove the precipitated white salt and washed with 300 ml of diethyl ether. The organic solvents were evaporated under vacuum to give the desired product N-(2,2-dimethoxyethyl)acetamide 57.1 g as colorless (or pink) oil in 97% yield which was used for next step without any further purification.

$^1H$ NMR (600 MHz, $CDCl_3$): δ 5.79 (s, 1H), 4.38 (t, J=5.2 Hz, 1H), 3.40 (d, J=7.4 Hz, 2H), 3.40 (s, 6H), 2.00 (s, 3H).

Synthesis of UCM924

The synthesis of UCM924 was carried out according to the method reported in Righi, M.; Bedini, A.; Piersanti, G.; Romagnoli, F.; Spadoni, G.; *J. Org. Chem.* 2011, 76, 704 and improved as follows.

The reaction scheme was:

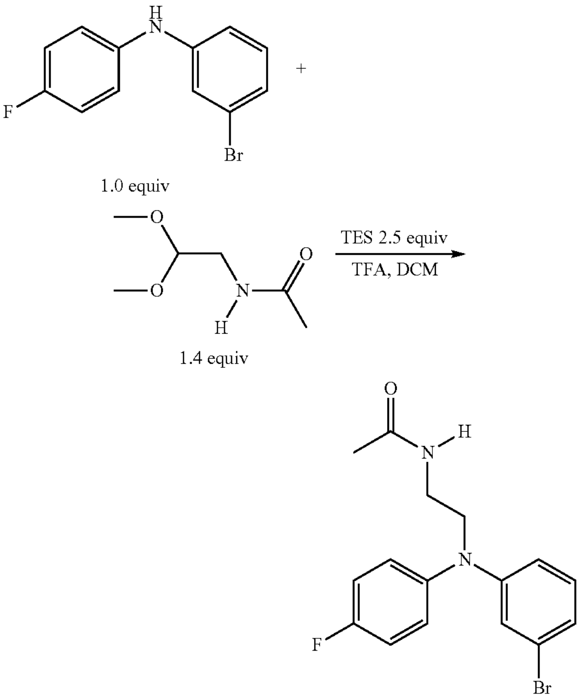

UCM 924
Recrystallization

The conditions used and the results were as reported in Table 4.

TABLE 4

Conditions and results for the synthesis of UMC924

| Entry | DCM/Conc | TFA | temperature | Time/h | Yield % | Scale mmol |
|---|---|---|---|---|---|---|
| ref | DCM:TFA 2:1 0.25M 17.4 equiv | | rt | 2 | 90%$_{FCC}$ | 1.0 |
| 1 | 25 ml/0.4M | 10 ml 13 equiv | 0° C. 5 mins rt 2h | 2 | 90% (79%$_{recry}$ + 11%$_{FCC}$) | 10 |
| 2 | 20 ml/0.5M | 2.68 ml 3.5 equiv | 0° C. 45 mins rt overnight | 24 | 81.6% (70%$_{recry}$ + 11.6%$_{FCC}$) | 10 |
| 3 | 20 ml/0.5M | 1.53 ml 2.0 equiv | 0° C. 5 mins rt overnight | 20 | 33.5%$_{FCC}$ | 10 |
| 4 | 50 ml/0.5M | 7.75 ml 4.0 equiv | 0° C. 5 mins rt 4h | 4 | 87% (80%$_{recry}$ + 7%$_{FCC}$) | 25 |
| 5 | 300 ml/ 0.6M | 56.14 ml 4.0 equiv | 0° C. 30 mins rt 5.5h | 6 | 82.4% (61.8%$_{recry}$ + 20.6%$_{FCC}$) | 180 |
| 6* | 10 ml/0.5M | 1.53 ml 4.0 equiv | rt | 1.5 | 93.7%$_{FCC}$ | 5.0 |
| 7* | 250 ml/ 0.56M | 42.95 ml 4.0 equiv | 0° C. 10 mins rt 3.5h | 3.5 | 85%$_{Recry}$ | 140 |

*
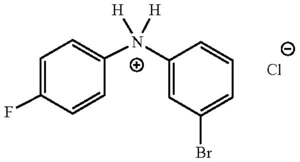
was the starting material.

DCM = dichloromethane; TFA = trifluoroacetic acid; rt = room temperature; recry = recrystallisation; FCC = Isolated yield by Flash Column Chromatography.

For Entry 5 reported in Table 4, the reaction scheme and protocol were as follow.

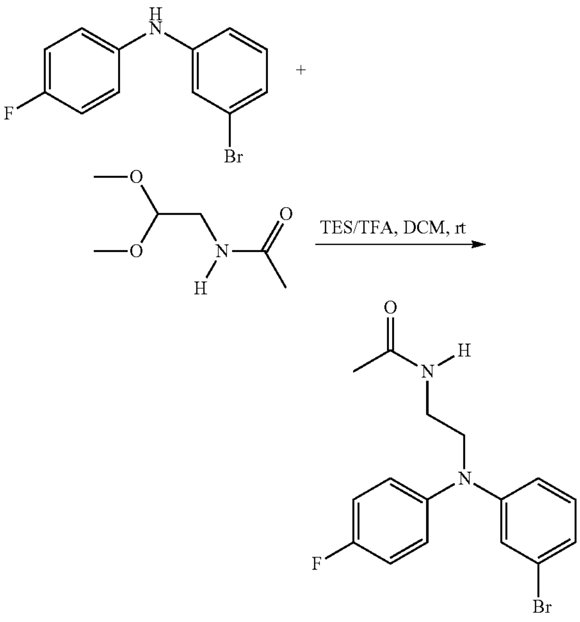

UCM 924

To a solution of 3-bromo-N-(4-fluorophenyl)aniline (183.3 mmol, 48.8 g) and N-(2,2-dimethoxyethyl)acetamide (1.4 equiv, 256.62 mmol, 37.77 g) in DCM (300 ml) at 0° C., were slowly added trifluoroacetic acid (TFA, 4 equiv, 733.2 mmol, 56.14 ml) in around 10 mins, then triethylsilane (TES, 2.5 equiv, 458.5 mmol, 73.234 ml) was slowly dropwise in 10 mins with dropping funnel. The resulting mixture was stirred at 0° C. for 30 mins and room temperature for another 5.5 hours to complete the reaction. The reaction was cooled at 0° C. and carefully neutralized with saturated solution of $NaHCO_3$ then diluted with EtOAc and $H_2O$. The aqueous layer was extracted with EtOAc (3×) and the combined organic phases were washed with $H_2O$ and brine, dried over $Na_2SO_4$, and concentrated under reduce pressure to give the crude product as brown solid which was further recrystallized from diethyl ether and Hexane to furnish 39.78 g of the desired UCM924 as white (or pale brown) solid in 61.8% yield. The mother liquid residue was concentrated under vacuum and flash column chromatography with 0% to 100% EtOAc/Hexane to give the desired product 13.28 g as white solid in 20.6% yield. The combined yield was 82.4%.

For Entry 7 reported in Table 4, the reaction scheme and protocol were as follow.

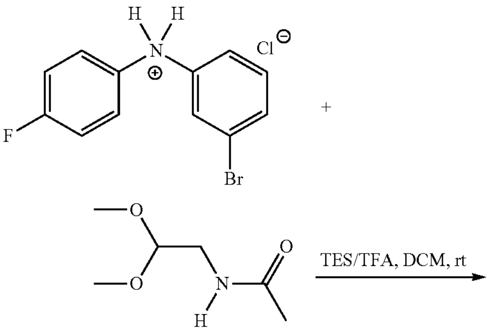

-continued

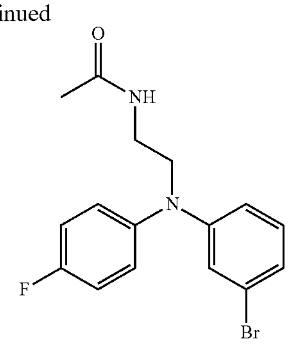

UCM 924

To a solution of 3-bromo-N-(4-fluorophenyl)aniline HCl salt (140 mmol, 42.36 g) and N-(2,2-dimethoxyethyl)acetamide (1.4 equiv, 196 mmol, 28.84 g) in DCM (250 ml) at 0° C., were slowly added trifluoroacetic acid (TFA, 4 equiv, 560 mmol, 42.95 ml) in around 10 mins, then triethylsilane (TES, 2.5 equiv, 350 mmol, 55.9 ml) was slowly dropwise in 10 mins with dropping funnel. The resulting mixture was stirred at 0° C. for 10 mins and room temperature for another 3.5 hours to complete the reaction. The reaction was cooled at 0° C. and carefully neutralized with saturated solution of $NaHCO_3$ then diluted with EtOAc and $H_2O$. The aqueous layer was extracted with EtOAc (3×) and the combined organic phases were washed with $H_2O$ and brine, dried over $Na_2SO_4$, and concentrated under reduce pressure to give the crude product as brown solid which was further recrystallized from DCM and Hexane to furnish 41.7 g of the desired UCM924 as pale brown solid in 85% yield.

$^1H$ NMR (600 MHz, Acetone) δ 7.31-7.28 (m, 3H), 7.20 (t, J=8.7 Hz, 2H), 7.11 (t, J=8.1 Hz, 1H), 6.98 (s, 1H), 6.91 (d, J=7.9 Hz, 1H), 6.83 (dd, J=8.4, 2.2 Hz, 1H), 3.81 (t, J=7.0 Hz, 2H), 3.42 (dd, J=13.5, 6.5 Hz, 2H), 1.86 (s, 3H).

Example 2—Synthesis of Compounds of the Invention

Various compounds were synthesized according to the two reaction schemes shown below.

A

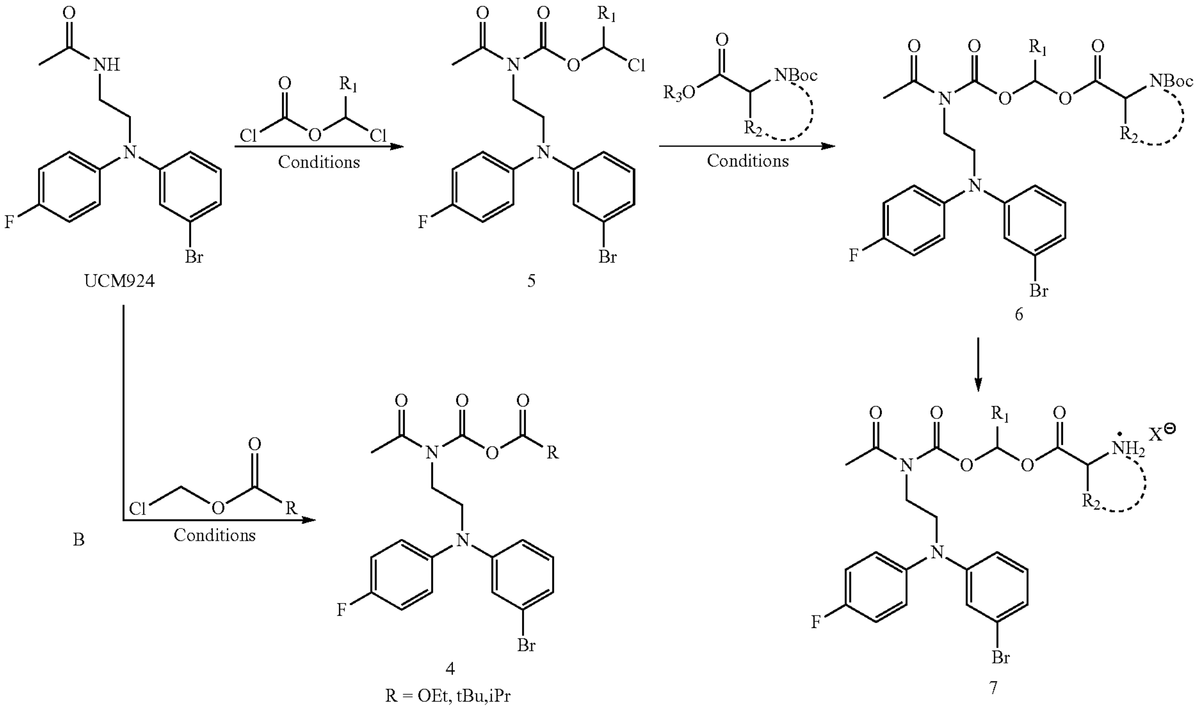

UCM924

5

6

B

4

R = OEt, tBu,iPr

7

In reaction scheme A, shown top right, a first reaction step leads to intermediate 5, then a second reaction step leads intermediate 6, and finally a third reaction step leads to compound 7. This reaction scheme was used to produce the following compounds:

-continued
Prodrug C 7a
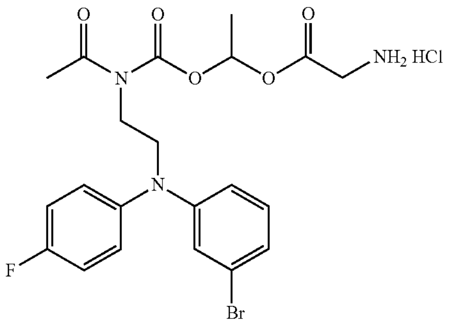
Prodrug D 7b
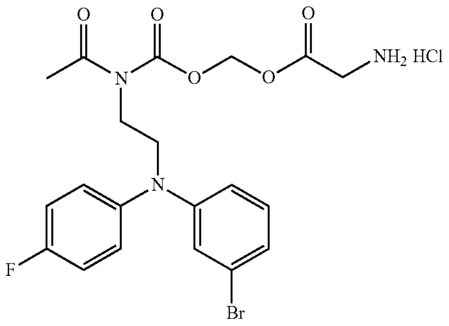
Prodrug D-2 7b-2
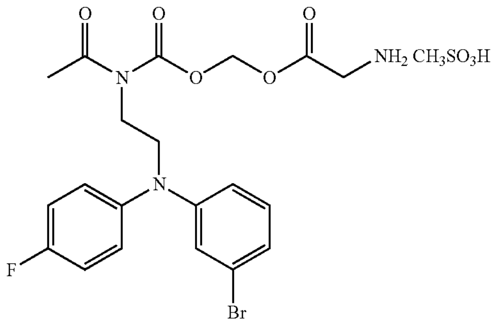
Prodrug E 7c
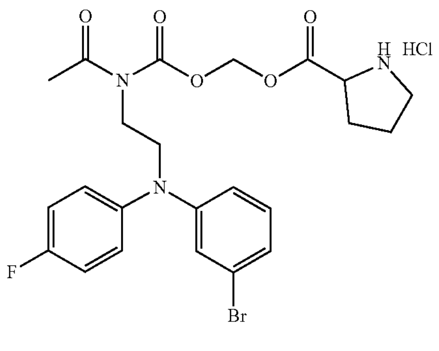
7d
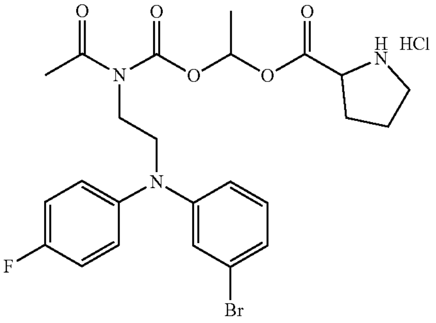
Prodrug F 7e
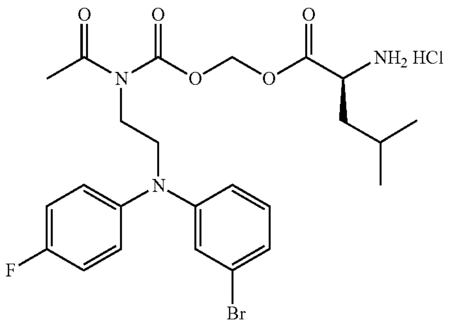
In reaction scheme B, shown bottom left, a single reaction step leads to compound 4. This reaction scheme was used to produce the following compounds:
Prodrug A 4a
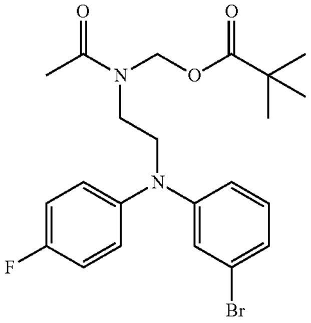
Prodrug B 4b
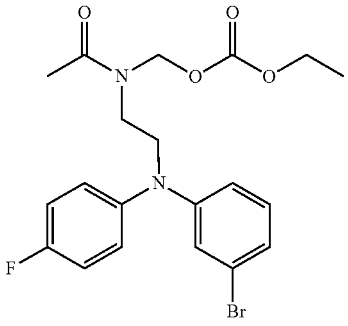

Synthesis Using to Reaction Scheme A

First Reaction Step of Reaction Scheme A—Synthesis of Intermediate 5

The first reaction step of reaction scheme A was carried out according to the following reaction scheme and improved using the conditions reported in Table 5.

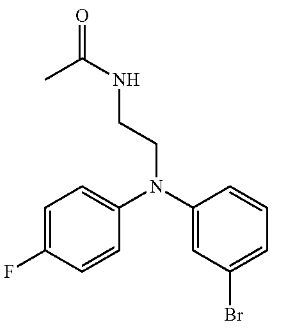

UCM 924

+

-continued

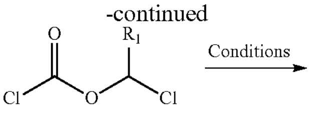

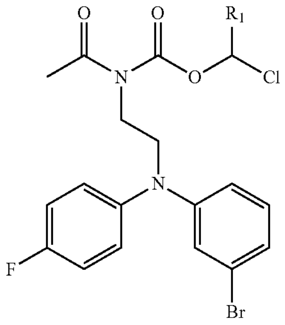

5

TABLE 5

Conditions and results for the first reaction step of Reaction scheme A

| Entry | 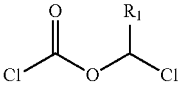 /eq | Base/ eq | Additive/ eq | Solvent/ Conc. | Temp/ ° C. | Time/h | Isolated Yield % | Scale mmol |
|---|---|---|---|---|---|---|---|---|
| 1 | $R_1$ = Me/2 | NaH/2 | — | THF/0.1M | rt | 24 | Trace, recover UCM924 | 0.1 |
| 2 | $R_1$ = Me/2 | LiHMDS/2[a] | — | THF/0.05M | rt | 24 | Product was observed, yield ND | 0.1 |
| 3 | $R_1$ = Me/2 | LiHMDS/2[a] | — | THF/0.05M | 0 | 0.5 | 62 | 0.1 |
| 4 | $R_1$ = Me/2 | LiHMDS/2[a] | — | THF/0.05M | 0 | 0.7 | 82 | 2.0 |
| 5 | $R_1$ = H/2 | LiHMDS/2[a] | — | THF/0.1M | 0 | 1.0 | Product was observed, yield ND | 0.1 |
| 6 | $R_1$ = H/2 | LiHMDS/2[a] | — | THF/0.06M | 0 | 2.0 | 71 | 3.0 |
| 7 | $R_1$ = H/2 | LiHMDS/2[a] | — | THF/0.06M | 0 | 2.0 | 78 | 3.0 |
| 8 | $R_1$ = H/2 | LiHMDS/2[b] | — | THF/0.3M | 0 | 2.0 | 13.8 | 15 |
| 9 | $R_1$ = H/2 | LiHMDS/2[b] | — | THF/0.06M | 0 | 2.0 | 38 | 2.0 |
| 10 | $R_1$ = H/2 | LiHMDS/2[b] | — | THF/0.3M | 0 | 3.0 | 30.7 | 2.0 |
| 11 | $R_1$ = H/2 | LiHMDS/2[b] | — | THF/0.3M | −10 to 0 | 3.0 | | 2.0 |
| 12 | $R_1$ = H/2 | LiHMDS/1.1[b] | — | THF/0.06M | 0 | 2.0 | 66.5 (+22 SM) | 2.0 |
| 13 | $R_1$ = H/2 | NaHMDS/1.1[b] | — | THF/0.2M | 0 | 2.0 | 24.3 | 2.0 |
| 14 | $R_1$ = H/2 | LiHMDS/1.3[b] | — | THF/0.2M | 0 | 2.0 | 62 (+14 SM) | 2.0 |
| 15 | $R_1$ = H/2.5 | LiHMDS/1.3[b] | — | THF/0.2M | 0 | 2.0 | 53.4 | 2.0 |
| 16 | $R_1$ = H/2 | LiHMDS/1.1[b] | — | DMF/0.1M | 0 | 2.0 | SM was decomposed | 2.0 |
| 17 | $R_1$ = H/2 | LiHMDS/1.1[c] | — | THF/0.05M | 0 | 2.0 | 53.3 | 15 |
| 18 | $R_1$ = H/2 | LiHMDS/1.1[c] | HMDS/2 | THF/0.08M | 0 | 2.0 | 56 | 2 |
| 19 | $R_1$ = H/2 | LiHMDS/1.1[c] | DIPEA/2 | THF/0.08M | 0 | 2.0 | | 2 |
| 20 | $R_1$ = H/2 | LiHMDS/1.05[c] | — | THF/0.05M | 0 | 2.0 | 41.7 | 20 |
| 21[d] | $R_1$ = H/2 | LiHMDS/1.1[c] | — | THF/0.2M | 0 | 1.0 | 82.9 | 2 |
| 22[d] | $R_1$ = H/2 | LiHMDS/1.05[c] | — | THF/0.05M | 0 | 1.0 | 80.1 | 20 |

*General Procedure: To the solution of UCM924 was added LiHMDS dropwise at 0° C. under argon atmosphere. After stirring 1h at 0° C., chloromethyl chloroformate was added and keep stirring.

[a]LiHMDS 1M in THF, Old bottle;

[b]LiHMDS 1M in THF, New bottle;

[c]LiHMDS 1.5M in THF, New bottle;

[d]To the solution of UCM924 was added LiHMDS dropwise at 0° C. under argon atmosphere. After stirring 1h at 0° C., then transform the above clear solution into the THE solution of chloromethyl chloroformate at 0° C. in 30-60 mins.

LiHMDS = lithium bis(trimethylsilyl)amide; HMDS = hexamethyldisiloxane; DIPEA = N,N-diisopropylethylamine; THF = tetrahydrofuran; DMF = dimethylformamide; rt = room temperature; SM = starting material; ND = not determined.

Two of the intermediate compounds produced were used in subsequent steps of the synthesis:

acetyl(2-((3-bromophenyl)(4-fluorophenyl)amino)ethyl) carbamate 5a, 1-chloroethyl acetyl(2-((3-bromophenyl)(4-fluorophenyl) amino)ethyl)carbamate 5b.

For Entry 22 reported in Table 5 (intermediate compound acetyl(2-((3-bromophenyl)(4-fluorophenyl)amino)ethyl) carbamate 5a), the reaction scheme and protocol were as follow.

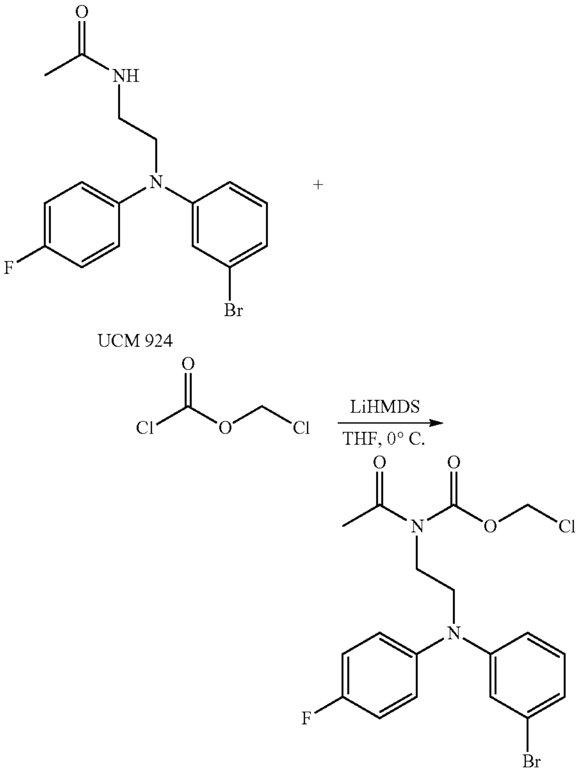

UCM 924

5a

In a dry round bottom flask (500 ml) was added UCM924 (7.024 g, 20 mmol, 1 equiv). The flask was evacuated and refilled with argon, this operation was repeated 3 times, followed by dry THF (200 ml) was added at 0° C. Then LiHMDS (21 ml, 21 mmol, 1M in THF, 1.05 equiv) was added dropwise into the reaction mixture in 10 mins at 0° C. under argon atmosphere. The reaction mixture was stirred at 0° C. for 60 min to complete the reaction. Slowly transform the above clear solution into a THF (200 ml) solution of chloromethylchloroformate (3.63 ml, 40 mmol, 2 equiv) at 0° C. in 30 mins. The resulting mixture was stirring at 0° C. for another 30 mins to complete the reaction. Quenched the reaction with water, the THF was removed under reduced pressure and the residue was diluted with Diethyl ether (or EtOAc). The aqueous solution was extracted with Diethyl ether (×3). The combined extracts were washed with brine, dried with $Na_2SO_4$, and concentrated under reduced pressure to give a crude residue of the desired product, which was purified by flash column chromatography ($SiO_2$, Hexane and EtOAc) to give the desired product 7.11 g as white solid in 80.1% yield.

$^1$H NMR (600 MHz, Acetone-d6): δ 7.31-7.19 (m, 4H), 7.15 (t, J=8.1 Hz, 1H), 7.05 (s, 1H), 6.96 (d, J=7.8 Hz, 1H), 6.86 (d, J=8.3 Hz, 1H), 5.98 (s, 2H), 4.09-4.02 (m, 2H), 3.92-3.86 (m, 2H), 2.45 (s, 3H).

For Entry 4 reported in Table 5 (intermediate compound 1-chloroethyl acetyl(2-((3-bromophenyl)(4-fluorophenyl) amino)ethyl)carbamate 5b), the reaction scheme and protocol were as follows.

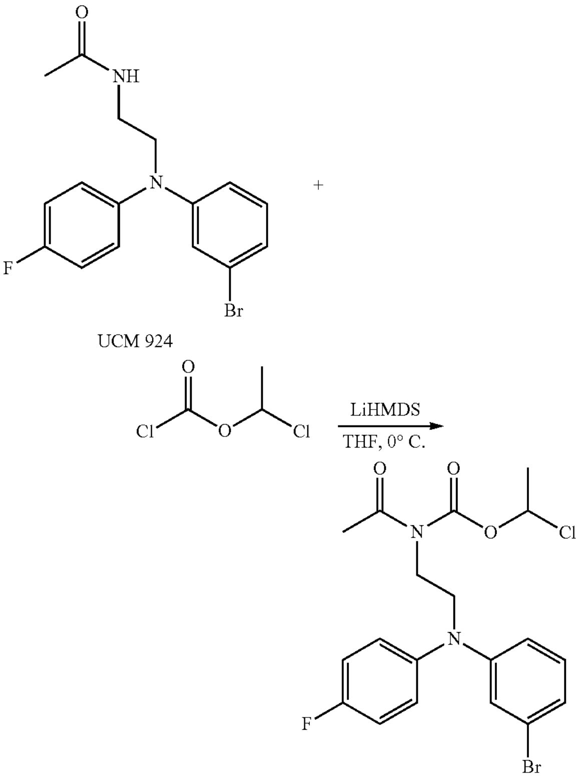

UCM 924

5b

To a THF (40 ml) solution of UCM924 (705 mg, 2 mmol, 1 equiv) was added dropwise LiHMDS (1M in THF, 2 equiv, 4 ml) at 0° C. under argon atmosphere. The mixture was stirred at 0° C. for 60 min, then 1-chloroethyl chloroformate (444 μl, 2 equiv, 4 mmol) was added, and the resulting mixture was stirring at 0° C. for another 40 mins to complete the reaction. Quenched the reaction with water, and the aqueous solution was extracted with EtOAc. The combined extracts were washed with brine, dried with $Na_2SO_4$, and concentrated under reduced pressure to give a crude residue of the desired product, which was purified by flash column chromatography to give the desired product 755 mg as pale yellow oil (pale yellow solid under vacuum overnight) in 82% yield.

$^1$H NMR (600 MHz, Acetone-d6): δ 7.34-7.27 (m, 2H), 7.25-7.20 (m, 2H), 7.16 (t, J=8.1 Hz, 1H), 7.03 (t, J=2.1 Hz, 1H), 6.96 (dd, J=7.9, 1.0 Hz, 1H), 6.88 (dd, J=8.4, 2.0 Hz, 1H), 6.64 (q, J=5.8 Hz, 1H), 4.12-3.99 (m, 2H), 3.94-3.80 (m, 2H), 2.44 (s, 3H), 1.79 (d, J=5.8 Hz, 3H).

Second Reaction Step of Reaction Scheme A—Synthesis of Intermediate 6

The second reaction step of reaction scheme A was carried out according to the following reaction scheme and improved using the conditions reported in Table 6 (FIG. 8A-B).

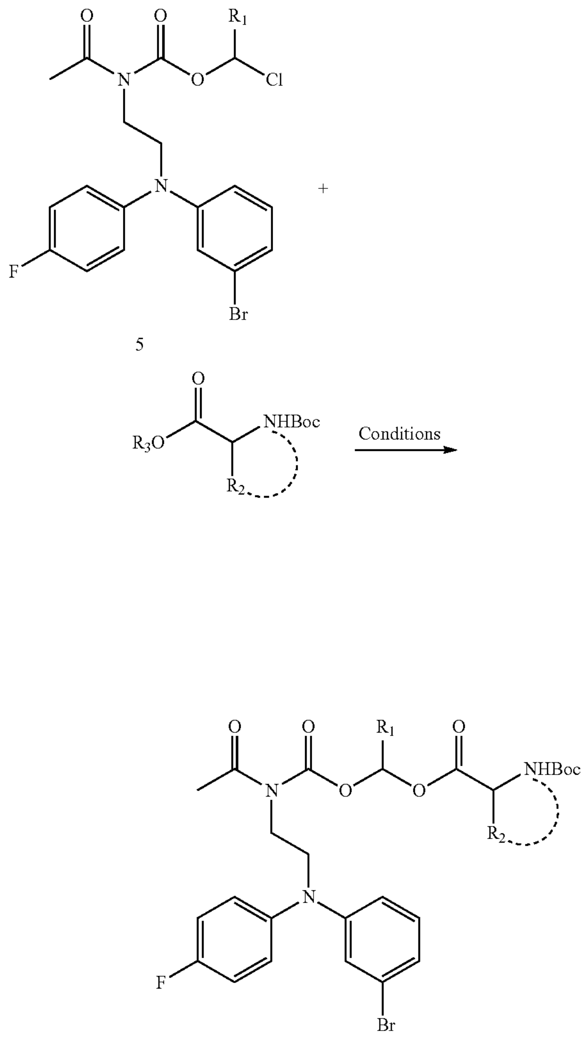

5

6

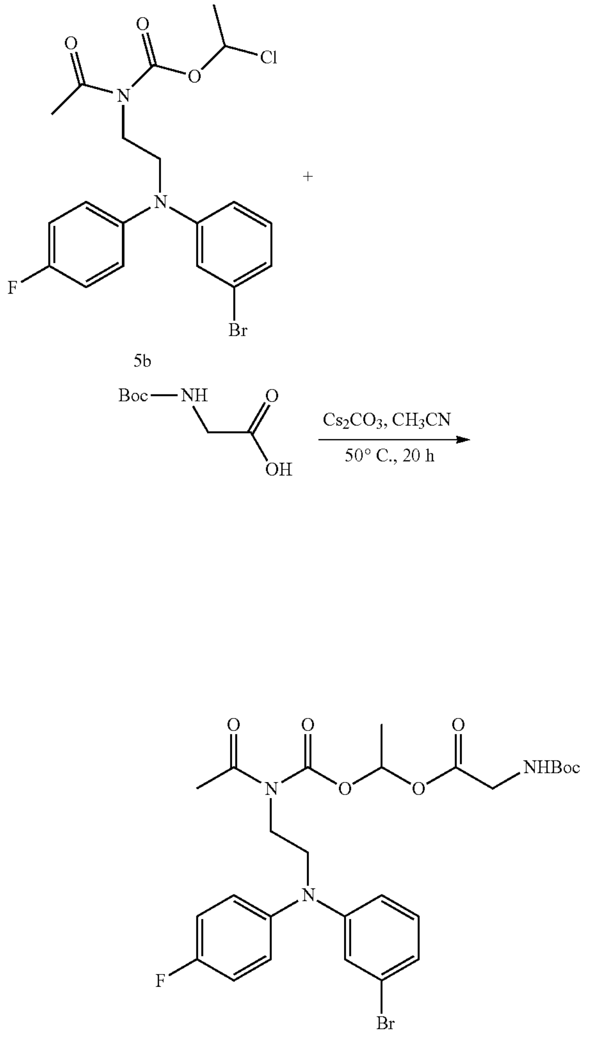

5b

6a

Five of the intermediate compounds produced were used in subsequent steps of the synthesis:

1-((acetyl(2-((3-bromophenyl)(4-fluorophenyl)amino)ethyl)carbamoyl)oxy)ethyl 2-((tert-butoxycarbonyl)amino)acetate 6a, ((acetyl(2-((3-bromophenyl)(4-fluorophenyl)amino)ethyl)carbamoyl)oxy)methyl 2-((tert-butoxycarbonyl)amino)acetate 6b, 2-(((acetyl(2-((3-bromophenyl)(4-fluorophenyl)amino)ethyl)carbamoyl)oxy)methyl) 1-tert-butyl pyrrolidine-1,2-dicarboxylate 6c, (2S)-2-(1-((acetyl(2-((3-bromophenyl)(4-fluoro-phenyl)amino)ethyl)carbamoyl)oxy)ethyl) 1-tert-butylpyro-lidine-1,2-dicarboxylate 6d, and (S)-((acetyl(2-((3-bromophenyl)(4-fluorophenyl)amino)ethyl)carbamoyl)oxy)methyl 2-((tert-butoxycarbonyl)amino)-4-methylpentanoate 6e.

For Entry 9 reported in Table 6 (intermediate compound 1-((acetyl(2-((3-bromophenyl)(4-fluorophenyl)amino)ethyl)carbamoyl)oxy)ethyl 2-((tert-butoxycarbonyl)amino)acetate 6a), the reaction scheme and protocol were as follow.

To a dry round bottom flask was added 1-chloroethyl acetyl(2-((3-bromophenyl)(4-fluorophenyl)amino)ethyl)carbamate (1 equiv, 1 mmol, 458 mg), Boc-Gly-OH (4 equiv, 4 mmol, 700 mg), $Cs_2CO_3$ (4equiv, 4 mmol, 1.3 mg) and $CH_3CN$ (36 ml). The reaction mixture was stirred at 50° C. for 20 h to complete the reaction. The solvent was removed under high vacuum and the residue was re-dissolved with EtOAc and water. The aqueous layer was extracted with EtOAc. The combined extracts were washed with brine, dried with $Na_2SO_4$, and concentrated under reduced pressure to give a crude residue of the desired product, which was purified by flash column chromatography to give the desired product 348 mg as colorless oil in 58% yield.

$^1H$ NMR (600 MHz, MeOD) δ 7.24-7.18 (m, 2H), 7.17-7.08 (m, 3H), 6.99 (s, 1H), 6.95-6.83 (m, 3H), 4.01 (t, J=7.1 Hz, 2H), 3.86-3.78 (m, 4H), 2.41 (s, 3H), 1.47 (d, J=5.4 Hz, 3H), 1.44 (s, 9H).

For Entry 23 reported in Table 6 (intermediate compound ((acetyl(2-((3-bromophenyl)(4-fluorophenyl)amino)ethyl)carbamoyl)oxy)methyl 2-((tert-butoxycarbonyl)amino)acetate 6b), the reaction scheme and protocol were as follow.

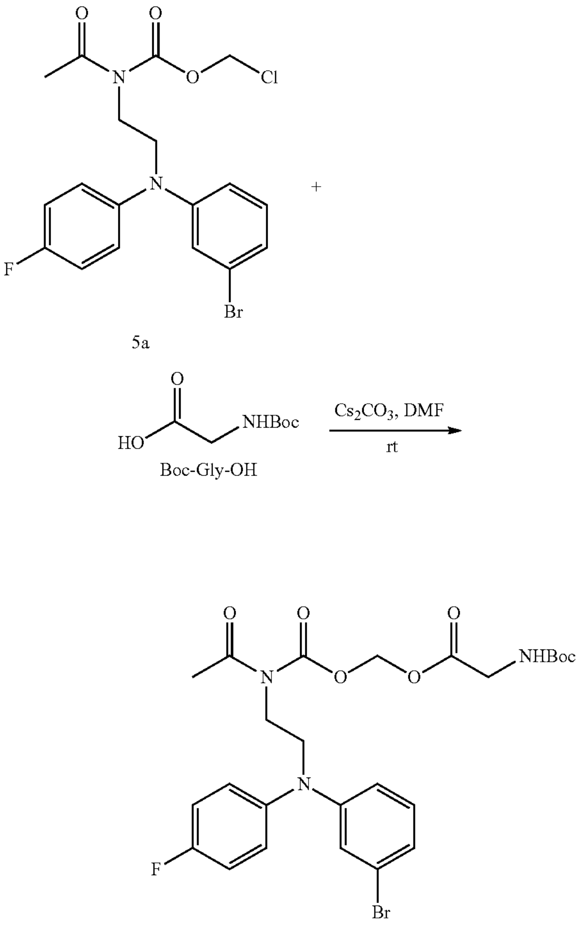

5a

Boc-Gly-OH

6b

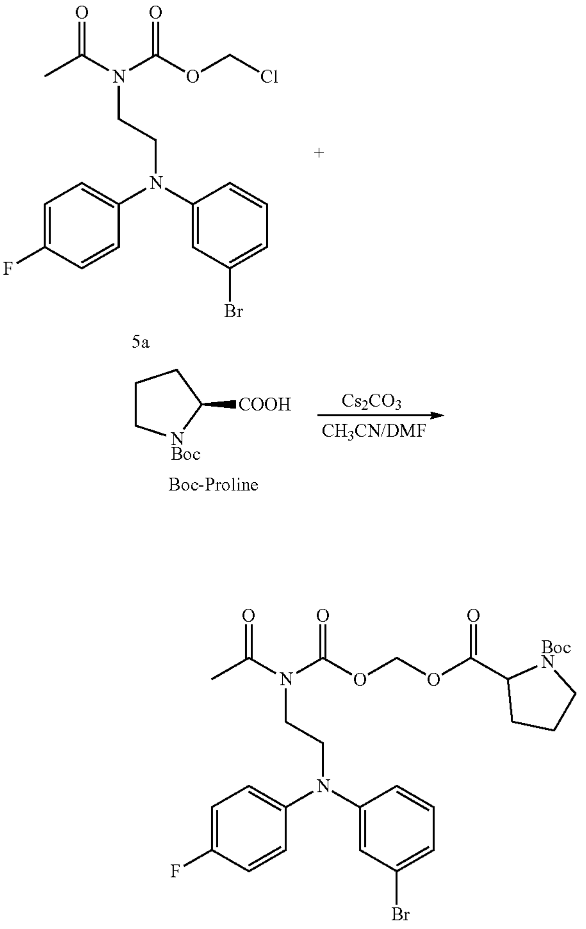

5a

Boc-Proline

6c

To a dry round bottom flask was added chloromethyl-acetyl(2-((3-bromophenyl)(4-fluorophenyl)amino)ethyl) carbamate (16 g, 36 mmol, 1 equiv), Boc-Gly-OH (12.87 g, 72 mmol, 2equiv), $Cs_2CO_3$ (23.7 g, 72 mmol, 2 equiv) and dry DMF (150 ml). The reaction mixture was stirred at rt for 6 hours to complete the reaction. The generated white precipitated was removed by filtration and washed with Diethyl ether (or EtOAc). The solution was concentrated under high vacuum to remove most of DMF, and the residue was diluted with Diethyl ether (or EtOAc) and $H_2O$. The aqueous layer was extracted with Diethyl ether (or EtOAc). The combined extracts were washed with brine, dried with $Na_2SO_4$, and concentrated under reduced pressure to give a crude residue of the desired product, which was purified by flash column chromatography ($SiO_2$, Hexane and EtOAc) to give the desired product 19.8 g as very viscous colorless oil in 87.7% yield.

$^1$H NMR (600 MHz, Acetone-d6): δ 7.31-7.15 (m, 5H), 7.03 (s, 1H), 6.96 (d, J=7.8 Hz, 1H), 6.92 (d, J=8.2 Hz, 1H), 6.44 (s, 1H), 5.92 (s, 2H), 4.03-3.98 (m, 2H), 3.92 (d, J=6.1 Hz, 2H), 3.88-3.84 (m, 2H), 2.43 (s, 3H), 1.41 (s, 9H).

For Entry 6 reported in Table 6 (intermediate compound 2-(((acetyl(2-((3-bromophenyl)(4-fluorophenyl)amino) ethyl)carbamoyl)oxy)methyl) 1-tert-butyl pyrrolidine-1,2-dicarboxylate 6c), the reaction scheme and protocol were as follow.

To a dry round bottom flask was added chloromethyl-acetyl(2-((3-bromophenyl)(4-fluorophenyl)amino)ethyl) carbamate (1 equiv, 0.5 mmol, 222 mg), Boc-Proline (4 equiv, 2.0 mmol, 431 mg), $Cs_2CO_3$ (4 equiv, 2.0 mmol, 652 mg) and $CH_3CN$ (10 ml). The reaction mixture was stirred at rt for 2 days. Then 10 ml of DMF was added into the reaction mixture (to increase the solubility) and kept stirring for another 5 hours to complete the reaction. The solvent was removed under high vacuum and the residue was re-dissolved with EtOAc and water. The aqueous layer was extracted with EtOAc. The combined extracts were washed with brine, dried with $Na_2SO_4$, and concentrated under reduced pressure to give a crude residue of the desired product, which was purified by flash column chromatography to give the desired product 262 mg as colorless oil in 84% yield.

$^1$H NMR (600 MHz, MeOD) δ 7.22-7.19 (m, 2H), 7.18-7.09 (m, 3H), 7.00 (s, 1H), 6.96-6.82 (m, 2H), 5.88 (dd, J=16.1, 5.8 Hz, 2H), 4.34-4.23 (m, 1H), 4.06-3.73 (m, 4H), 3.55-3.38 (m, 2H), 2.45 (s, 3H), 2.32-2.18 (m, 1H), 1.98-1.89 (m, 3H), 1.40 (d, J=11.2 Hz, 9H).

For Entry 1 reported in Table 6 (intermediate compound (2S)-2-(1-((acetyl(2-((3-bromophenyl)(4-fluoro-phenyl) amino)ethyl)carbamoyl)oxy)ethyl) 1-tert-butylpyro-lidine-1,2-dicarboxylate 6d), the reaction scheme and protocol were as follow.

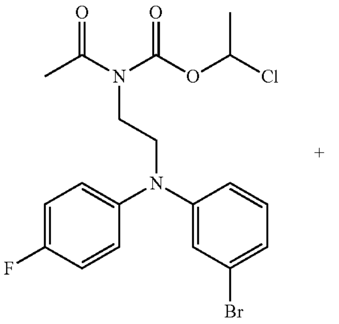

5a

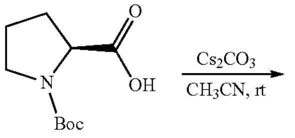

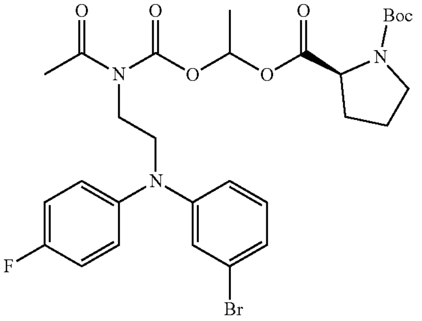

6d

To a dry round bottom flask was added 1-chloroethyl acetyl(2-((3-bromophenyl)(4-fluorophenyl)amino)ethyl) carbamate (1 equiv, 0.1 mmol, 45.8 mg), Boc-Proline (2 equiv, 0.2 mmol, 43 mg), $Cs_2CO_3$ (2equiv, 0.2 mmol, 66 mg) and $CH_3CN$ (1 ml). The reaction mixture was stirred at rt for 4 days. The solvent was removed under high vacuum and the residue was re-dissolved with EtOAc and water. The aqueous layer was extracted with EtOAc. The combined extracts were washed with brine, dried with $Na_2SO_4$, and concentrated under reduced pressure to give a crude residue of the desired product, which was purified by flash column chromatography to give the desired product 30 mg in 47% yield.

$^1H$ NMR (600 MHz, DMSO) δ 7.30-7.19 (m, 4H), 7.16-7.10 (m, 1H), 6.95-6.93 (m, 2H), 6.85-6.69 (m, 2H), 4.19-4.14 (dd, J=19.4, 7.8 Hz, 1H), 3.96-3.71 (m, 4H), 3.40-3.25 (m, 2H), 2.33 (s, 3H), 2.27-2.07 (m, 1H), 1.91-1.69 (m, 3H), 1.48-1.25 (m, 12H).

For Entry 17 reported in Table 6 (intermediate compound (S)-((acetyl(2-((3-bromophenyl)(4-fluorophenyl)amino) ethyl)carbamoyl)oxy)methyl 2-((tert-butoxycarbonyl) amino)-4-methylpentanoate 6e), the reaction scheme and protocol were as follow.

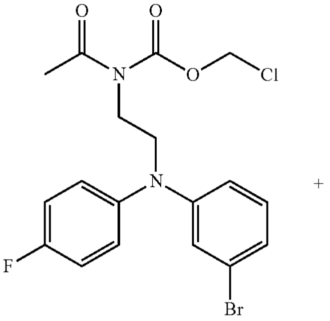

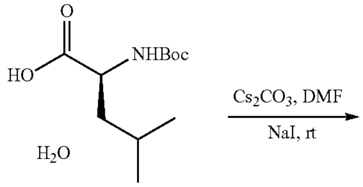

Boc-Leu-OH $H_2O$

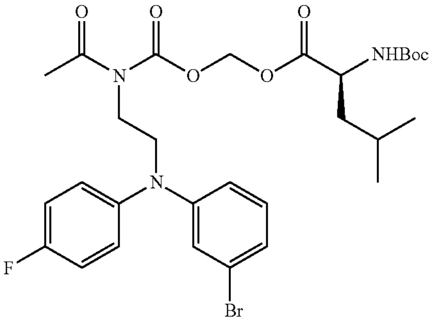

To a dry round bottom flask was added chloromethyl-acetyl(2-((3-bromophenyl)(4-fluorophenyl)amino)ethyl) carbamate (1 equiv, 0.8 mmol, 355.2 mg), Boc-Leu-OH $H_2O$ (4 equiv, 3.2 mmol, 800 mg), NaI (4 equiv, 3.2 mmol, 480 mg), $Cs_2CO_3$ (4 equiv, 3.2 mmol, 1.042 g) and DMF (15 ml). The reaction mixture was stirred at rt for overnight to complete the reaction. The DMF was removed under high vacuum and the residue was re-dissolved with EtOAc and water. The aqueous layer was extracted with EtOAc. The combined extracts were washed with brine, dried with $Na_2SO_4$, and concentrated under reduced pressure to give a crude residue of the desired product, which was purified by flash column chromatography to give the desired product 446 mg as colorless oil in 87% yield.

$^1H$ NMR (600 MHz, Acetone) δ 7.31-7.26 (m, 2H), 7.23-7.14 (m, 3H), 7.04 (t, J=2.0 Hz, 1H), 6.94 (ddd, J=9.9, 8.1, 1.3 Hz, 2H), 6.42 (d, J=7.6 Hz, 1H), 5.93 (s, 2H), 4.26-4.21 (m, 1H), 4.03-3.98 (m, 2H), 3.89-3.82 (m, 2H), 2.44 (s, 3H), 1.85-1.54 (m, 3H), 1.38 (s, 9H), 0.94 (dd, J=9.1, 6.6 Hz, 6H).

Combined First and Second Reaction Steps of Reaction Scheme A

In some tests, the first and second reaction steps of Reaching Scheme A were carried out without isolation of intermediate compound 5. The combined reaction step was carried out according to the following reaction scheme and improved using the conditions reported in Table 7, to yield compound 6b.

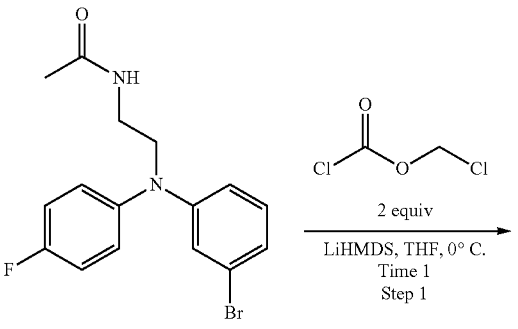

UCM924

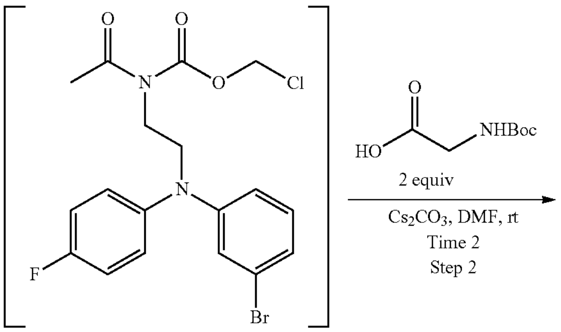

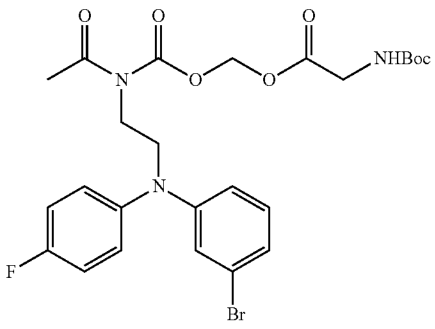

6b

In a dry round bottom flask (1000 ml) was added UCM924 (35.12 g, 100 mmol, 1 equiv). The flask was evacuated and refilled with argon, this operation was repeated 3 times, followed by dry THF (400 ml) was added at 0° C. Then LiHMDS (70 ml, 105 mmol, 1.5 M in THF, 1.05 equiv) was added dropwise into the reaction mixture in 10 mins at 0° C. under argon atmosphere. The reaction mixture was stirred at 0° C. for 75 mins to complete the reaction. Slowly transform the above clear solution into a THF (600 ml) solution of chloromethylchloroformate (18.15 ml, 200 mmol, 2 equiv) at 0° C. in 60 mins. The resulting mixture was stirring at 0° C. for another 90 mins to complete the reaction. Quenched the reaction with water, the THF was removed under reduced pressure and the residue was diluted with Diethyl ether. The aqueous solution was extracted with Diethyl ether (×3). The combined extracts were washed with brine, dried with $Na_2SO_4$, and concentrated under reduced pressure to give a crude product, which was used for next step without further purification.

The resulting residue, chloromethylacetyl(2-((3-bromophenyl)(4-fluorophenyl)amino)ethyl)carbamate was dissolved in dry DMF 300 ml at room temperature. Then Boc-Gly-OH (35.75 g, 200 mmol, 2 equiv) and $Cs_2CO_3$ (65.8 g, 200 mmol, 2 equiv) were added and the reaction mixture was stirred at rt for 6 hours to complete the reaction. The generated white precipitated was removed by filtration and washed with Diethyl ether. The solution was concentrated under high vacuum to remove most of DMF, and the residue was diluted with Diethyl ether and $H_2O$. The aqueous layer was extracted with Diethyl ether. The combined extracts were washed with brine, dried with $Na_2SO_4$, and concentrated under reduced pressure to give a crude residue of the desired product, which was purified by flash column chromatography ($SiO_2$, Hexane and EtOAc) to give the desired product 37.95 g as very viscous colorless oil in 65% yield.

Third Reaction Step of Reaction Scheme A—Synthesis of Compound 7

The third and last reaction step of reaction scheme A was first attempted according to the following reaction scheme and improved using the conditions reported in Table 8.

TABLE 7

Conditions and results for the second reaction step of Reaction scheme A

| | Step 1 | | | Step 2 | | | | |
|---|---|---|---|---|---|---|---|---|
| Entry | Base/eq | Solvent/ Conc. | Time/h | Base/eq | Solvent/ Conc. | Time/h | Yield % | Scale mmol |
| 1 | LiHMDS/1.05 | THF/0.06M | 2.0 | $Cs_2CO_3$/2 | DMF/0.27 | 6.0 | 62.2 | 40 |
| 2 | LiHMDS/1.05 | THF/0.06M | 2.0 | $Cs_2CO_3$/2 | DMF/0.27 | 6.0 | 72.5 | 40 |
| 3 | LiHMDS/1.05 | THF/0.1M | 2.5 | $Cs_2CO_3$/2 | DMF/0.33 | 6.0 | 65 | 100 |

LiHMDS = lithium bis(trimethylsilyl)amide;

THF = tetrahydrofuran;

DMF = dimethylformamide;

no difference in the conditions in entries 1 and 2 (verification of reproducibility);

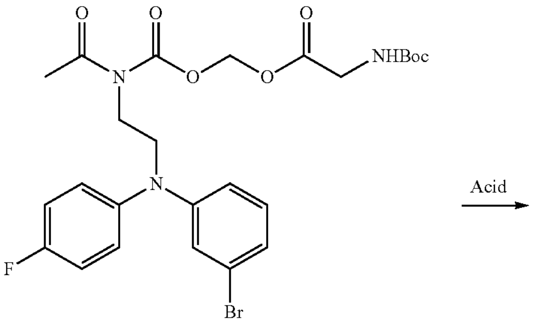

6b

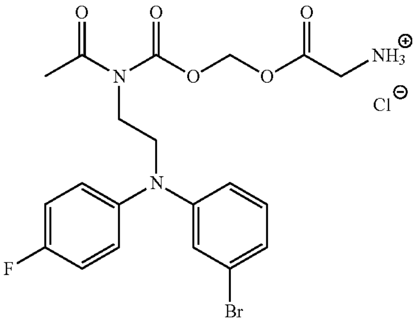

7

TABLE 8

| Conditions and results for the last reaction step of Reaction scheme A | | | | | | | |
|---|---|---|---|---|---|---|---|
| Entry | 4M HCl in dioxane | Solvent/Conc. | Temp/° C. | Time/h | Note HPLC | Yield % | Scale mmol |
| 1 | 30 eq | Diethyl ether/0.05M | rt | 4.5 | SM 80% + <1% UCM924 | trace | 0.1 |
| 2 | 15 eq | MeOH/0.05M | rt | 1.5 | Lots of UCM924 was observed | 38 | 0.57 |
| 3 | 0 eq | MeOH/0.1M | rt | 2.5 | SM 60% + 29% UCM924 | — | 0.1 |
| 4 | 10 eq | EtOH/0.05M | rt | 3.0 | SM 57% + 19% UCM924 | $15_{HPLC}$ | 0.1 |
| 5 | 10 eq | IPA/0.05M | rt | 2.0 | SM 81% + 2% UCM924 | $6_{HPLC}$ | 0.1 |
| 6 | 10 eq, 0.5M | HCl in $H_2O$/0.05M | rt | 4.5 | Not determined | | 0.1 |
| 7 | 10 eq | $CH_3CN$/0.05M | rt | 3.5 | SM 5% + trace UCM924 | $88_{HPLC}$ | 0.1 |
| 8 | 10 eq | $CH_3CN$/0.05M | rt | 4 | — | 85.5 | 4.5 |
| 9 | 10 eq | $CH_3CN$/0.068M | rt | 40 min | ~90% with 1 × HCl, ~10 with 2 × HCl | 100 | 34 |
| 10 | 10 eq | $CH_3CN$/0.065M | 0-rt | 60 min | 1 × HCl | 93.1 | 65 |

MeOH = methanol;
EtOH = ethanol;
IPA = isopropyl alcohol;
rt = room temperature;
SM = starting material Based on the above result, the third reaction step of reaction scheme A was attempted according to the following reaction scheme and improved using the conditions reported in Table 9.

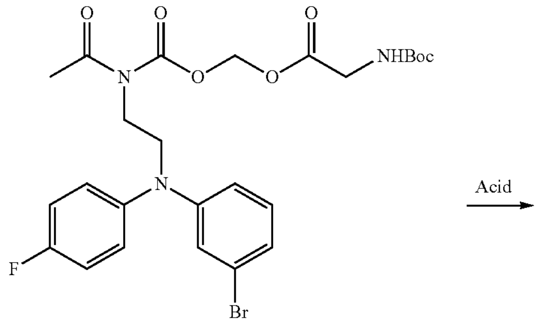

6b

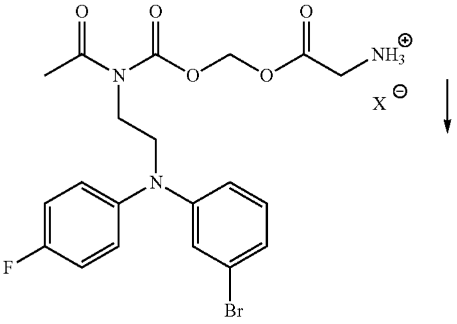

7

TABLE 9

| Conditions and results for the last reaction step of Reaction scheme A | | | | | | |
|---|---|---|---|---|---|---|
| Entry | Acid | Solvent | Temp/° C. | Time/h | Note | Product |
| 1 | PTSA $H_2O$ 10 eq | THF | rt | 24 | No product precipitated from the solution | — |
| 2 | $CH_3SO_3H$ 10 eq | MTBE | rt | 1.5 | White solid was precipitated from the solution | 82% |
| 3 | $PhSO_3H$ 5 eq | MTBE | rt | 5-72 | No product precipitated from the solution after 5 h Very viscous oil was precipitated from the solution over weekend | — |
| 4 | PTSA $H_2O$ 5 eq | MTBE | rt | 5-72 | No product precipitated from the solution after 5 h Very viscous oil was precipitated from the solution over weekend | — |

PTSA = p-toluenesulfonic acid;

$PhSO_3H$ = benzenesulfonic acid;

THF = tetrahydrofuran;

MTBE = methyl tert-butyl ether

Using the reaction conditions determined above, six compounds were produced:

Compound 7a—Prodrug C: 1-((acetyl(2-((3-bromophenyl)(4-fluorophenyl)amino)ethyl)carbamoyl)oxy)ethyl 2-aminoacetate hydrochloride, Compound 7b—Prodrug D: ((acetyl(2-((3-bromophenyl)(4-fluorophenyl)amino)ethyl)carbamoyl)oxy)methyl 2-aminoacetate hydrochloride, Compound 7b-2—Prodrug D-2: ((acetyl(2-((3-bromophenyl)(4-fluorophenyl)amino)ethyl)carbamoyl)oxy)methyl 2-aminoacetate methane-sulfonate, Compound 7c—Prodrug E: ((acetyl(2-((3-bromophenyl)(4-fluorophenyl)amino)ethyl)carbamoyl)oxy)methyl pyrrolidine-2-carboxylate hydrochloride, Compound 7d—Prodrug G: (2S)-1-((acetyl(2-((3-bromophenyl)(4-fluorophenyl)amino)ethyl)carbamoyl)oxy)ethyl pyrrolidine-2-carboxylate hydrochloride, and Compound 7e—Prodrug F: ((S)-((acetyl(2-((3-bromophenyl)(4-fluorophenyl)amino)ethyl)carbamoyl)oxy)methyl 2-amino-4-methylpentanoate hydrochloride.

Compound 7a—Prodrug C

Compound 7a—Prodrug C (1-((acetyl(2-((3-bromophenyl)(4-fluorophenyl)amino)ethyl)carbamoyl)oxy)ethyl 2-aminoacetate hydrochloride) was synthesized as follows.

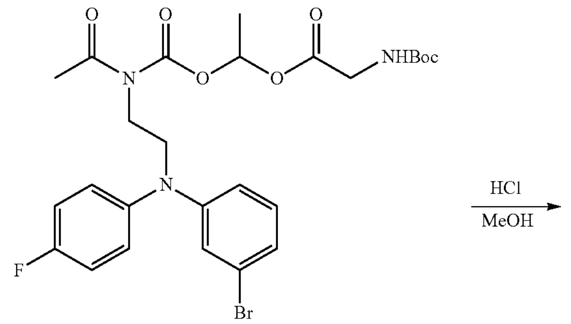

6a

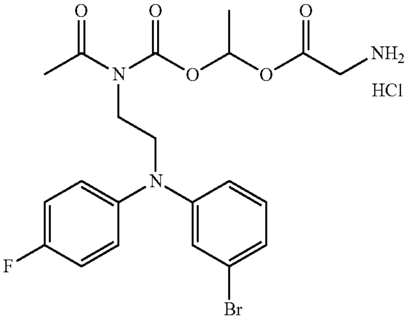

7a

To a MeOH (10 ml) solution of starting material (340 mg, 0.57 mmol, 1 equiv) was added dropwise HCl (4M in dioxane, 15 equiv, 2.14 ml) at 0° C. The mixture was stirred at 0° C. for 1 h, then warmed up to rt for another 1.5 h to complete the reaction. The organic solvents were evaporated under vacuum, the residue was suspended in trace amount of EtOAc, diethyl ether and Hexane was added to induce precipitation of the desired HCl salt as white solid or very viscous colorless oil. This procedure was repeated for three times. The resulting product was re-dissolved with 5-10 ml of DI water, the mixture was then frozen and dried under lyophilizer to give the final product as a white solid 104 mg in 32% yield.

Compound 7b—Prodrug D

Compound 7b—Prodrug D (((acetyl(2-((3-bromophenyl)(4-fluorophenyl)amino)ethyl)carbamoyl)oxy)methyl 2-aminoacetate hydrochloride) was synthesized as follows.

-continued

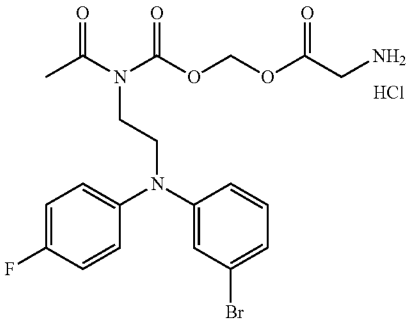

7b Prodrug D

To a $CH_3CN$ (500 ml) solution of starting material (19.8 g, 92.9% purity, 31.58 mmol, 1 equiv) was added HCl solution (4M in dioxane, 79 ml, 316 mmol, 10equiv) at room temperature. The mixture was stirred at rt for 40 min to complete the reaction. The organic solvents were evaporated under vacuum, the residue was suspended in trace amount of EtOAc, and diethyl ether was added to induce precipitation of the desired HCl salt as white solid (or very viscous colorless oil was sticky on the flask), then remove the supernatant. This procedure was repeated for three times. The desired white solid (or very viscous colorless oil) was under high vacuum to give the final product as a white foam solid 14.7 gin 89.7% yield.

$^1$H NMR (600 MHz, DMSO-d6): δ 8.46 (s, 3H), 7.28-7.22 (m, 4H), 7.16 (t, J=7.9 Hz, 1H), 6.96 (s, 1H), 6.96 (d, J=7.8 Hz, 1H), 6.80 (d, J=7.9 Hz, 1H), 5.88 (s, 2H), 3.91 (s, 2H), 3.89-3.85 (m, 2H), 3.81-3.74 (m, 2H), 2.38 (s, 3H).

MS: Calcd. For $C_{20}H_{22}BrFN_3O_5^+[M-Cl^-]$: 482.07; Found: 482.43.

Compound 7b-2—Prodrug D-2

Compound 7b-2—Prodrug D-2 (((acetyl(2-((3-bromophenyl)(4-fluorophenyl)amino)ethyl)carbamoyl)oxy) methyl 2-aminoacetate methane-sulfonate) was synthesized as follows.

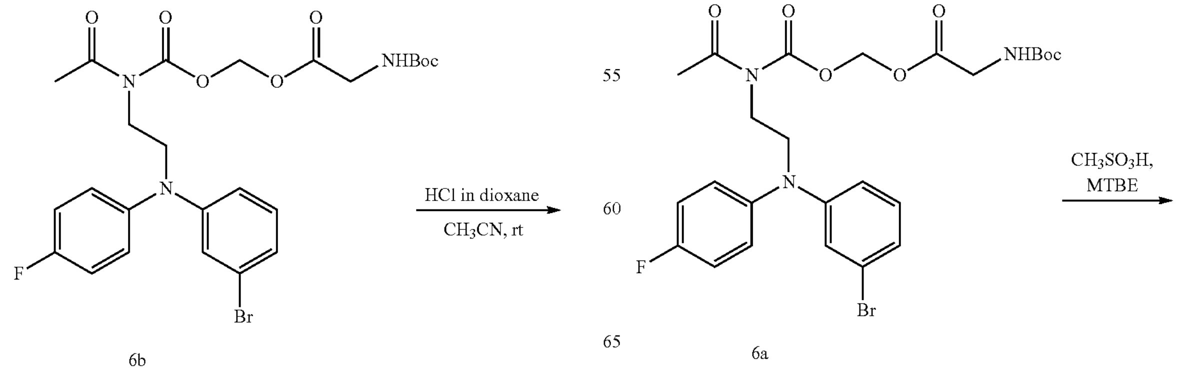

6b

6a

-continued

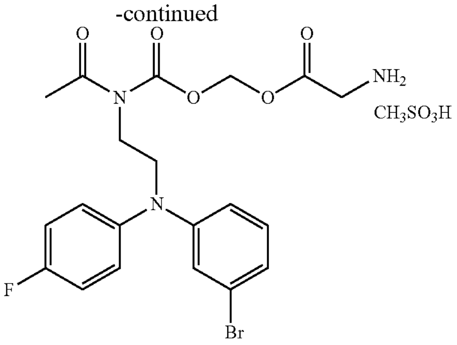

7b-2

To a MTBE (5 ml) solution of starting material (582.4 mg, 1.0 mmol, 1 equiv) was added $CH_3SO_3H$ (0.65 ml, mmol, 10 equiv) at room temperature. The mixture was stirred at rt for 1.5 h to complete the reaction. The precipitated white solid was filtrated, washed with MTBE and Hexane to give the desired product 475 mg as white powder in 82% yield.

$^1$H NMR (600 MHz, DMSO) δ 8.30 (s, 3H), 7.29-7.20 (m, 4H), 7.16 (t, J=8.1 Hz, 1H), 6.96 (d, J=7.6 Hz, 2H), 6.83-6.75 (m, 1H), 5.88 (s, 2H), 3.94 (d, J=5.3 Hz, 2H), 3.91-3.84 (m, 2H), 3.81-3.73 (m, 2H), 2.38 (s, 3H), 2.35 (s, 3H).

Compound 7c—Prodrug E

Compound 7c—Prodrug E (((acetyl(2-((3-bromophenyl)(4-fluorophenyl)amino)ethyl)carbamoyl)oxy)methyl pyrrolidine-2-carboxylate hydrochloride) was synthesized as follows.

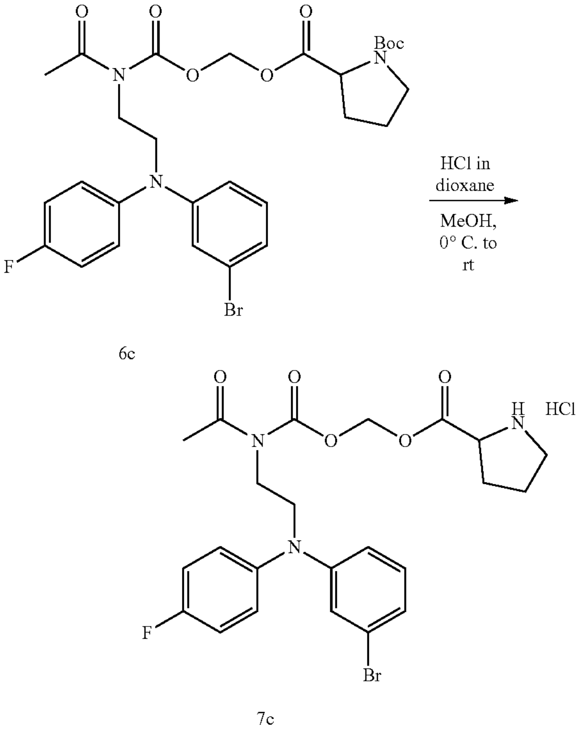

6c

7c

To a MeOH (12 ml) solution of starting material (446 mg, 0.699 mmol, 1equiv) was added dropwise HCl (4M in dioxane, 15 equiv, 2.6 ml) at 0° C. under argon atmosphere.

The mixture was stirred at 0° C. for 10-15 min, then warmed up to rt for another 1.5 h to complete the reaction. The organic solvents were evaporated under vacuum, the residue was suspended in trace amount of EtOAc, diethyl ether and Hexane was added to induce precipitation of the desired HCl salt as white solid or very viscous colorless oil. This procedure was repeated for three times. The resulting product was re-dissolved with 5-10 ml of DI water, the mixture was then frozen and dried under lyophilizer to give the final product as a white solid 92.3 mg in 39% yield.

$^1$H NMR (600 MHz, MeOD) δ 7.21 (dd, J=8.7, 4.8 Hz, 2H), 7.18-7.08 (m, 3H), 7.02 (s, 1H), 6.94 (d, J=7.8 Hz, 1H), 6.87-6.82 (m, 1H), 5.97 (dd, J=42.7, 6.0 Hz, 2H), 4.57-4.40 (m, 1H), 4.04 (t, J=7.3 Hz, 2H), 3.88-3.78 (m, 2H), 3.53-3.34 (m, 2H), 2.46 (s, 3H), 2.49-2.41 (m, 1H), 2.19-2.03 (m, 3H).

Compound 7d—Prodrug G

Compound 7d—Prodrug G (2S)-1-(acetyl(2-((3-bromophenyl)(4-fluorophenyl)amino)ethyl) carbamoyl)oxy)ethyl pyrrolidine-2-carboxylate hydrochloride) was synthesized as follows.

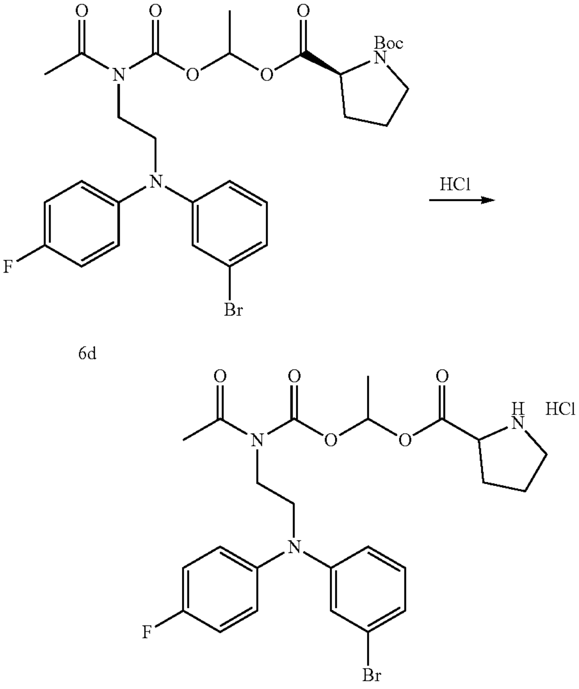

6d

7d

To a Diethyl ether (1 ml) solution of starting material (30 mg, 0.05 mmol, 1equiv) was added dropwise HCl (4M in dioxane, 0.3 ml) at 0° C. The mixture was stirred at rt for 5 h. The organic solvents were evaporated under vacuum, the residue was suspended in trace amount of EtOAc, diethyl ether and Hexane was added to induce precipitation of the desired HCl salt as white solid or very viscous colorless oil. This procedure was repeated for three times. The resulting product was re-dissolved with 2 ml of DI water, the mixture was then frozen and dried under lyophilizer to give the final product as a white solid <10 mg.

Compound 7e—Prodrug F

Compound 7e—Prodrug F(((S)-((acetyl(2-((3-bromophenyl)(4-fluorophenyl)amino)ethyl)carbamoyl)oxy)methyl 2-amino-4-methylpentanoate hydrochloride) was synthesized as follows.

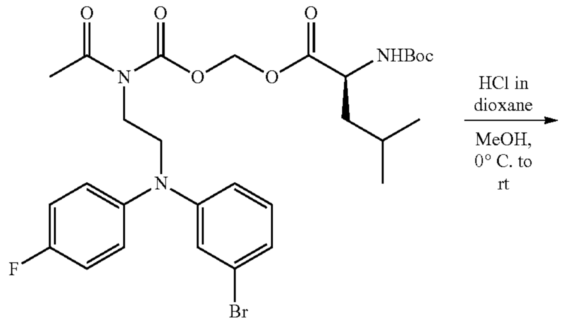

6e

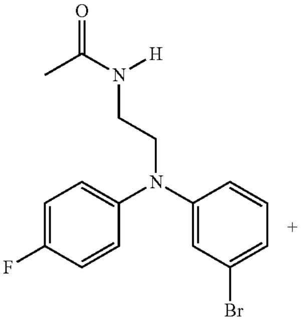

UMC924

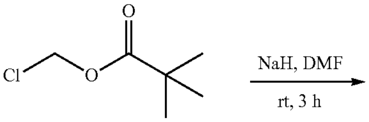

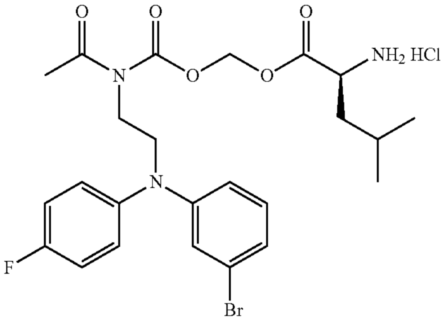

7e

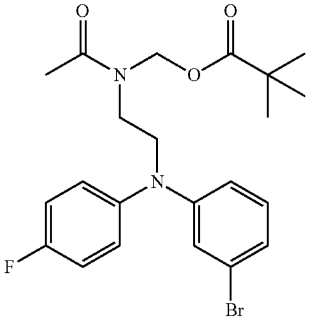

4a

To a MeOH (12 ml) solution of starting material (446 mg, 0.699 mmol, 1equiv) was added dropwise HCl (4M in dioxane, 15 equiv, 2.6 ml) at 0° C. under argon atmosphere. The mixture was stirred at 0° C. for 10-15 min, then warmed up to rt for another 1.5 h to complete the reaction. The organic solvents were evaporated under vacuum, the residue was suspended in trace amount of diethyl ether, and Hexane was added to induce precipitation of the desired HCl salt as white solid or very viscous colorless oil. This procedure was repeated for three times. The resulting product was re-dissolved with 5-10 ml of DI water, the mixture was then frozen and dried under lyophilizer to give the final product as a white solid 70 mg in 17.5% yield (major impurity is UCM924).

$^1$H NMR (600 MHz, MeOD) δ 7.21 (dd, J=8.6, 4.9 Hz, 2H), 7.18-7.09 (m, 3H), 7.03 (s, 1H), 6.95 (d, J=7.8 Hz, 1H), 6.86 (d, J=8.3 Hz, 1H), 5.97 (dd, J=38.1, 6.0 Hz, 2H), 4.13 (t, J=7.0 Hz, 1H), 4.05-3.99 (m, 2H), 3.89-3.83 (m, 2H), 2.47 (s, 3H), 1.87-1.75 (m, 2H), 1.75-1.65 (m, 1H), 1.06-0.95 (m, 6H).

Synthesis Using to Reaction Scheme B

As noted above, reaction scheme B allows producing compounds from UCM924 in a single step Compound 4a—Prodrug A Compound 4a—Prodrug A (N-(2-((3-bromophenyl)(4-fluorophenyl)amino)ethyl)acetamido) methyl pivalate) was synthesized as follows.

The UCM924 (50.0 mg, 0.142 mmol) was dissolved in DMF (2.85 mL) then NaH (6.0 mg, 0.157 mmol) was added at room temperature and the reaction mixture was stirred for 15 min. Chloromethyl pivalate (0.042 mL, 0.285 mmol) was added and the reaction mixture was stirred at room temperature for 3 h. To the previous solution, water was added, and the aqueous layer was extracted twice with EtOAc. The combined organic layers were washed with a saturated aqueous solution of sodium chloride, dried over $Na_2SO_4$, filtered and the solvent evaporated in vacuum. The crude material was purified on silica gel with a gradient from 0% to 60% EtOAc in Hexane to provide the desired material as a colorless oil (51.4 mg, 77.6%).

$^1$H NMR (600 MHz, Chloroform-d) δ 7.21-7.12 (m, 2H), 7.12-7.06 (m, 3H), 7.02 (d, J=2.3 Hz, 1H), 6.95 (d, J=8.0 Hz, 1H), 6.85 (dd, J=8.3, 2.6 Hz, 1H), 5.31 (d, J=1.3 Hz, 2H), 3.86 (t, J=7.3 Hz, 2H), 3.68 (t, J=7.5 Hz, 2H), 2.21 (d, J=1.4 Hz, 3H), 1.21 (d, J=2.5 Hz, 9H). MS m/z: 363.5 [M—$(CH_3)_3CCO_2$].

Compound 4b—Prodrug B

Compound 4b—Prodrug B((N-(2-((3-bromophenyl)(4-fluorophenyl)amino)ethyl)acetamido) methyl ethyl carbonate) was synthesized as follows:

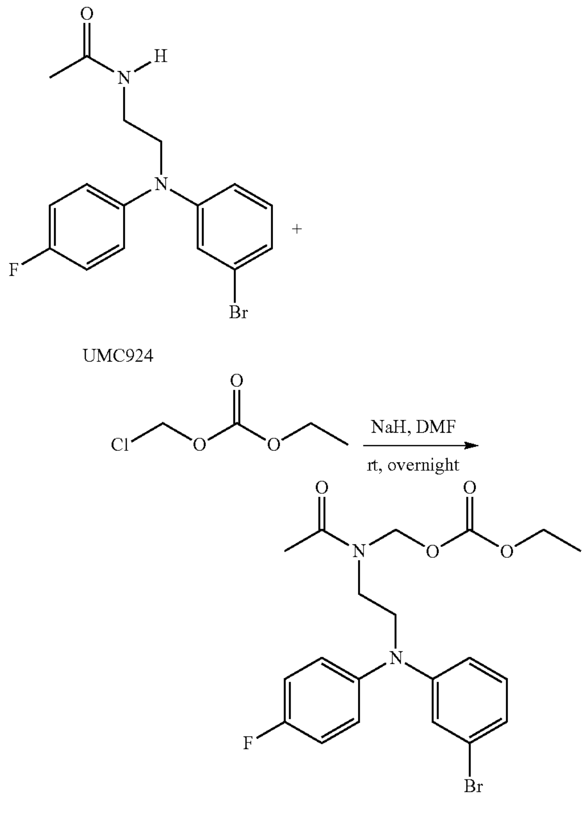

UMC924

4b

A solution of the UCM924 (210 mg, 0.6 mmol, 1 equiv) in dry DMF (5 mL) was added NaH (60% dispersion in mineral oil, 48 mg, 1.2 mmol, 2equiv) under argon atmosphere. The mixture was stirred at 0° C. for 60 min, then chloromethyl ethyl carbonate (0.215 mL, 1.8 mmol, 3 equiv) was added dropwise, and the resulting mixture was warmed up to room temperature for overnight to complete the reaction. Quenched the reaction with water, and the aqueous solution was extracted with diethyl ether (×3). The combined extracts were washed with brine, dried with $Na_2SO_4$, and concentrated under reduced pressure to give a crude residue of the desired product, which was purified by flash column chromatography to give the desired product 63 mg as colorless oil in 23% yield.

$^1$H NMR (600 MHz, Acetone) δ 7.30 (dd, J=8.8, 4.9 Hz, 2H), 7.20 (t, J=8.7 Hz, 2H), 7.13 (t, J=8.1 Hz, 1H), 7.06 (s, 1H), 6.95-6.89 (m, 2H), 5.50 (s, 2H), 4.17 (q, J=7.1 Hz, 2H), 3.93-3.84 (m, 2H), 3.74-3.66 (m, 2H), 2.21 (s, 3H), 1.25 (t, J=7.1 Hz, 3H).

Example 3—Improving the Second Step of the Synthesis of the Compounds of the Invention According to Reaction Scheme A of In this example, we report the improvement of the second step of the synthesis of the compounds of the invention starting from UCM924 as reported in Example 2, Reaction scheme A. We show below this whole synthesis, more details on the second step of this synthesis as well as the proposed mechanism for the second step.

Synthesis of Compound of the Invention Starting from UCM924:

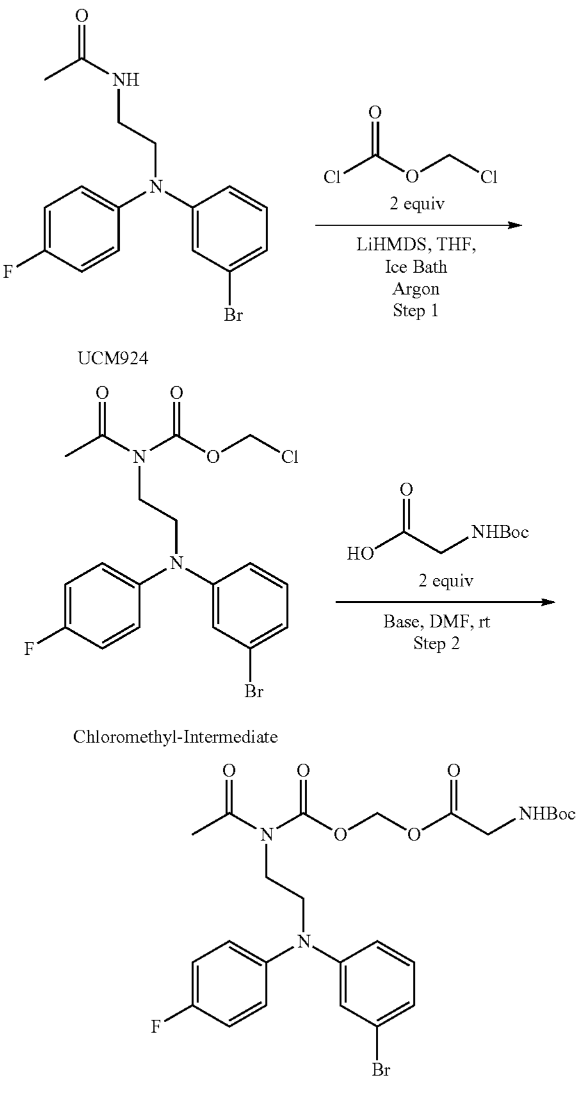

UCM924

Chloromethyl-Intermediate

Boc-Prodrug D

Second step—CsCO: Conditions:

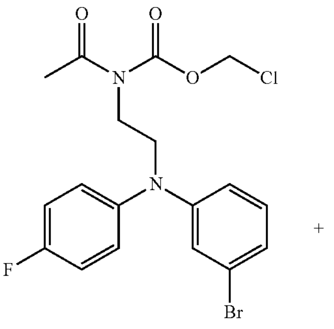

Chloromethyl-Intermediate

-continued

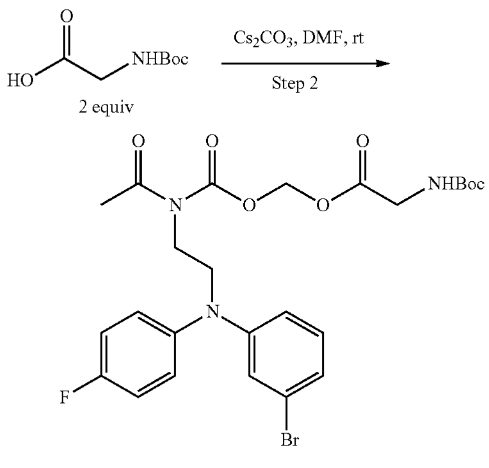

Boc-Prodrug D

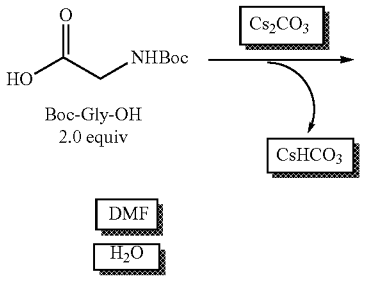

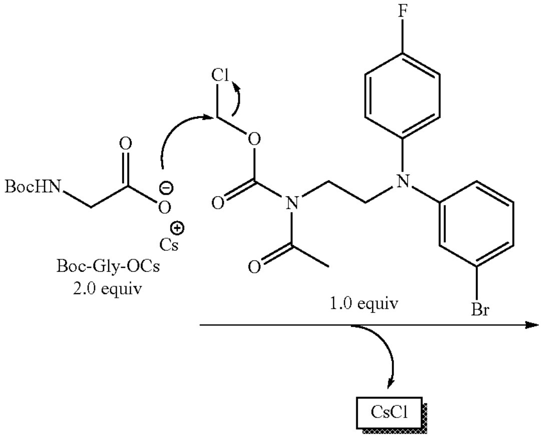

-continued

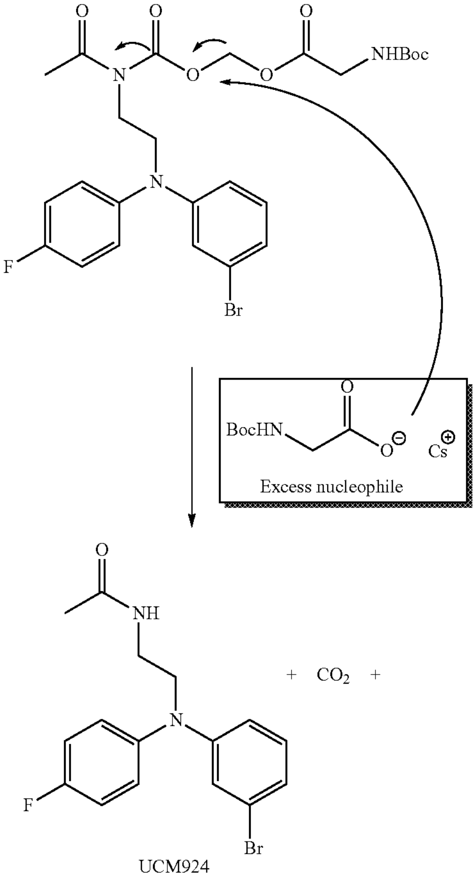

UCM924

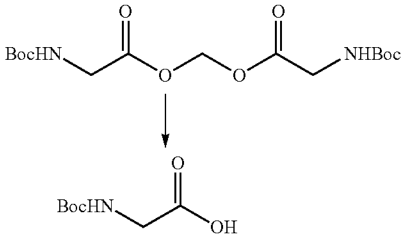

X 2

We confirmed that the base used, the temperature, the solvent, the order in which the reactants are added, and the reaction time could have an impact on this reaction.

According to the $Cs_2CO_3$ condition used in Example 2, the starting chloromethyl-intermediate and desired product have to coexists with $Cs_2CO_3$, $CsHCO_3$, CsCl, Excess Boc-Gly-OCs, DMF and even trace amount of water in the system for a few hours.

Through the following experiments, we figured out which factor(s) resulted into the decomposition of the Boc-Prodrug D or the starting Chloromethyl-Intermediate.

Experiment and Results for the Stability Analysis of Boc-Prodrug D

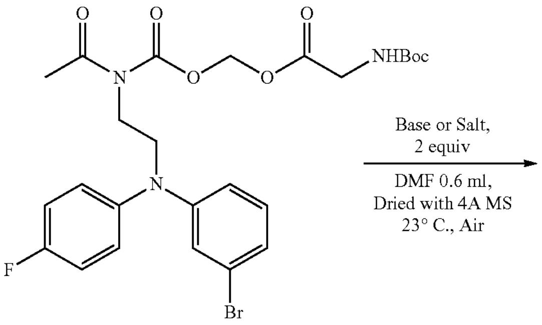

Boc-Prodrug D
0.1 mmol, 95% HPLC
61.3 mg, After 18 months
in Fridge

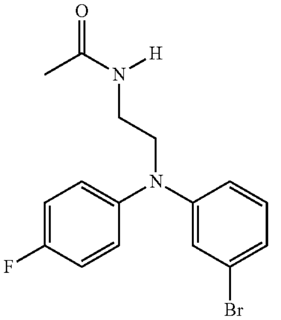

UCM924

Stability Analysis of Chloromethyl Intermediate:

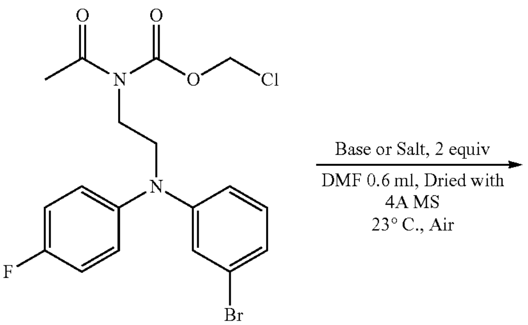

Chloromethyl Intermediate
0.1 mmol, 94.83% HPLC
46.7 mg

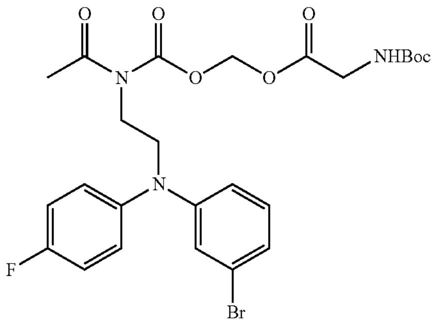

Boc-Prodrug D

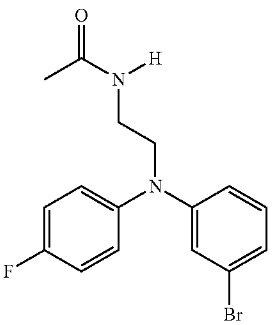

UCM924

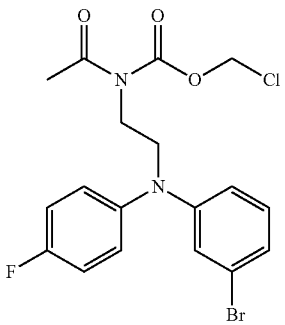

Chloromethyl Intermediate

TABLE 10

| | | Blank | $Cs_2CO_3$ | CsCl | $NaHCO_3$ | $K_2CO_3$ | 10% water |
|---|---|---|---|---|---|---|---|
| 0 h | UCM924 | 0% | | | | | |
| | SM | 95.71% | | | | | |
| 3 h | UCM924 | <0.5% | 84.41% | <0.5% | 16.62% | 59.41% | |
| | SM | 94.14% | 0% | 92.76% | 76.54% | 30.26% | |
| ON | UCM924 | <0.5% | | | 30.79% | | <0.5% |
| | SM | 92.98% | | | 60.84% | | 95.14% |

SM = starting material

ON = overnight

TABLE 11

| | | Blank | $Cs_2CO_3$ | CsCl | $NaHCO_3$ | $K_2CO_3$ | 10% water |
|---|---|---|---|---|---|---|---|
| 0 | UCM924 | | | 0% | | | 0% |
| | SM | | | 97.51% | | | 94.83% |
| 3 h | UCM924 | 0.39% | 7.98% | 0.37% | 1.42% | 26.31% | |
| | SM | 97.14% | 23.82% | 96.95% | 97.47% | 40.25% | |
| | Impurity | 0% | 38.36% | 0% | 0% | 24.98% | |
| ON | UCM924 | 1.15% | Decomposed | 0.98% | 3.22% | Decomposed | 1.75% |
| | SM | 96.32% | | 97.06% | 95.26% | | 93.16% |

Based on the above, we concluded that:

Both Chloromethyl Intermediate and Boc-Prodrug D are relatively stable in the presence of DMF and/or water at room temperature.

Both these two compounds are unstable in the presence of $Cs_2CO_3$ or $K_2CO_3$. Boc-Prodrug D mainly decomposed back to UCM924; the decomposition rate is faster with $Cs_2CO_3$ than $K_2CO_3$ probably due to the different solubility in DMF. But the Chloromethyl Intermediate decomposed to a very complex mixture.

Both these two compounds are stable in the presence of CsCl.

As $CsHCO_3$ was back ordered and is not available in short time, we used $NaHCO_3$ to replace it. Chloromethyl Intermediate was relatively stable in the presence of $NaHCO_3$, but the Boc-Prodrug D was slowly decomposed back to UCM924. This probably results into the non-homogeneous of the system and explains the instability of reaction (Yield vary from as high as >80% to as low as <50%).

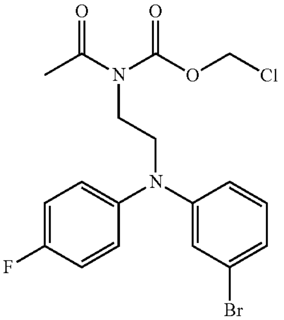

Chloromethyl-Intermediate

1

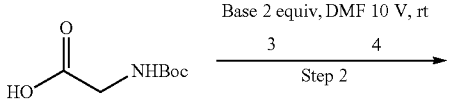

2 equiv

2

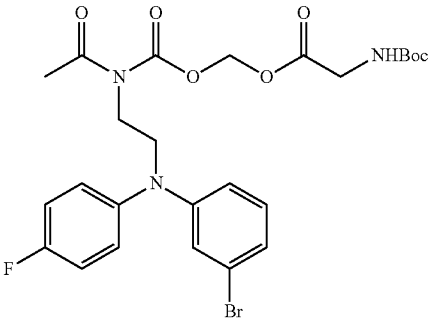

Boc-Prodrug D

To overcome this problem, we decided to use a different base. We decided to use a base without HCO3 ion and proceeded with the following experiments:

TABLE 12

| Entry | Base | Sequence of addition | Time/h | UCM 924%$_{HPLC}$ | | 1 + Product %$_{HPLC}$ | Yield %$_{iso}$ | Note | Scale mmol | SL |
|---|---|---|---|---|---|---|---|---|---|---|
| 1 | $Cs_2CO_3$ | (123) 4 | 5.5 | 3 h | 8.74 | 85.79 | 75 | Original conditions | 2.2 | 2009 |
| | | | | 5.5 h | 15.2 | 80.31 | | | | |
| 2 | $K_2CO_3$ | (123) 4 | 12 | 3 h | 5.59 | 90.55 | 75 | Double reaction time compared to $Cs_2CO_3$ | 1.0 | 2011 |
| | | | | 5 h | 7.95 | 86.90 | | | | |
| | | | | 9 h | 9.88 | 83.12 | | | | |
| | | | | 12 h | — | — | | | | |
| 3 | $NaHCO_3$ | (123) 4 | 24 | 3 h | 4.03 | 92.46 | ND | Very slow, lot of starting material left after 24 h | 1.0 | 2012 |
| | | | | 24 h | 6.49 | 88.49 | | | | |
| 4 | LiOH | (123) 4 | 72 | 3 h | 2.33 | 96.80 | 59 | Very slow, half of starting material left after 24 h, still lots of SM after 48 h | 1.0 | 2015 |
| | | | | 8 h | 3.13 | 95.58 | | | | |
| | | | | 24 h | 4.40 | 94.70 | | | | |
| | | | | 48 h | 7.40 | 90.96 | | | | |
| 5 | NaOH | (123) 4 | 8 | 2 h | 8.39 | 87.64 | ND | Very slow, lot of starting material left after 8 h | 1.0 | 2014 |
| | | | | 8 h | 8.72 | 85.11 | | | | |

TABLE 12-continued

| Entry | Base | Sequence of addition | Time/h | UCM 924%$_{HPLC}$ | | 1 + Product %$_{HPLC}$ | Yield %$_{iso}$ | Note | Scale mmol | SL |
|---|---|---|---|---|---|---|---|---|---|---|
| 6 | NaOH | (234) to (14) | 8 | 2 h | 3.72 | 93.30 | ND | Very slow, lot of starting | 1.0 | 2014 |
| | | | | 8 h | 5.01 | 91.33 | | material left after 8 h | | |
| 7 | tBuOK | (123) 4 | 8 | 3 h | 21.61 | 62.74 | ND | Starting material was still | 1.0 | 2019 |
| | | | | 8 h | 23.15 | 55.41 | | observed after 8 h | | |
| 8 | BuOK | (234) to (14) | 16 | 3 h | 6.43 | 90.05 | 77 | | 1.0 | 2023 |
| | | | | 16 h | 10.58 | 81.56 | | | | |
| 9 | KOH | (234) to (14) | 20 | 17 h | 6.92 | 90.55 | 90 | Slower than CsOH, but | 4.5 (2 g) | 2021 |
| | | | | | | | | clean reaction | | |
| 10 | CsOH | (234) to (14) | 8 | 3 h | 4.86 | 93.24 | 80 | Reaction clean and fast, | 1.0 | 2022 |
| | $H_2O$ | | | 5 h | 5.19 | 93.26 | | but expensive | | |
| 11 | KOH | (234) to (14) | 20 | 17 h | 6.85 | 90.99 | *94 | Recovered 4% starting | 50 (22.8 g) | 2024 |
| | | | | 20 h | 7.37 | 90.37 | | material; 27.4 g product | | |
| 12 | KOH | (234) to (14) | 20 | 20 h | 5.92 | 90.55 | *93 | 59.5 g product with trace EA | 107 (50 g) | 2026 |

*The Product is extremely viscous and trace amounts of solvents remained in it. They were rather difficult to remove. Thus, the Isolated Yield above is a bit of higher than the actual yield which should be around 90%.

The decomposition rate of Boc-Prodrug D was slower in the presence of $K_2CO_3$ than $Cs_2CO_3$. As shown in entry 2, we still tried one experiment with $K_2CO_3$ as the base even though $KHCO_3$ would be generated. The reaction also gave the desired product with comparable yield, but double reaction time was needed, and the reaction was not homogeneous either. Using $NaHCO_3$ as the base was also tested as shown in Entry 3, although only 6.49% of UCM924 was observed, there were still lots of starting material left and only trace amount of product was found after 24 hours.

Both Boc-Prodrug D and Chloromethyl Intermediate were relatively stable in presence of 10% water in DMF for 24 hours. M+OH-bases such as LiOH and NaOH were tested in the pro-drug synthesis, but the reaction rate was very slow (59% product was isolated after 3 days for LiOH, Entry 4).

In addition, different material adding sequences were tested using NaOH as the base. Treatment of Boc-Gly-OH with NaOH to generate the Boc-Gly-ONa intermediate in-situ and dropwise addition of this DMF solution into the Chloromethyl Intermediate slightly diminished the generation of undesired UCM924 (Entries 5 and 6). This phenomenon was clearer while using t-BuOK as the base, 77% of desired product was isolated while the dropwise addition of the in-situ generated Boc-Gly-OK into the chloromethyl intermediate.

Using KOH as the base to generate Boc-Gly-OK intermediate and then dropwise adding it into the starting material, the reaction furnished the desired product in 90% isolated yield with 2 g scale after 20 h at room temperature, only 6.92% of undesired UCM924 was observed based on HPLC analysis (Entry 9). The experiment reacted faster and was clean while using CsOH as the base, 80% of product was isolated after 8 h (Entry 10). However, considering caesium hydroxide is corrosive enough to dissolve glass quickly and expensive, we decided to use the cheaper and easier to handle KOH as the base in the prodrug synthesis.

Example 4—Scale Up of Synthesis of the Compounds of the Invention According to Reaction Scheme A of Example 2

We scaled up the first and second steps of the synthesis of the compounds of the invention according to Reaction Scheme A of Example 2.

Both these two reactions worked smoothly and gave the desired product in >90% yield. The Product is extremely viscous and trace amounts of solvents remained in it. They were rather difficult to remove. Thus, the Isolated Yield above is a bit of higher than the actual yield which should be around 90% (these trace amounts of solvents did not affect the next reaction step however).

First Step of Reaction Scheme A—33 Grams

In a Flame dried 1 L RBF under argon were charged 33.37 g UCM924 and 380 ml dry THF. The reaction mixture was cooled down with an ice bath (~5° C.) under argon. Then, 100 ml LiHMDS (1.05 eq, 1M in THF, new bottle) were added dropwise into the reaction mixture in around 11 min via a double tipped needle at ~5° C. under argon. The reaction mixture (Clear brown solution) was stirred at ~5° C. under argon for 2 h to complete the reaction.

Set up THE solution of Chloromethyl Chloroformate while waiting for the completion of the reaction between UCM924 and LiHMDS. In a Flame dried 2 L RBF under argon was charged 570 ml dry THF followed by 17.24 ml Chloromethyl Chloroformate. The clear THF solution was cooled down with an ice bath (~5° C.) under argon.

The above reaction mixture (with UCM924 &LiHMDS) was transferred portion-wise into the clear THF solution of chloromethyl chloroformate in 1 h via a double tipped needle at ~5° C. (ice bath) under argon. The resulting mixture was kept stirring for another 1.5 h under an ice bath to complete the reaction.

In-progress check (IPC, end of reaction) by HPLC=81.48% (12.58% UCM924+5.94% Side products).

The reaction was quenched with 50 ml $H_2O$ while keeping the flask in an ice bath, the THF was removed under reduced pressure (Rotary Evaporator, <35° C.) and the brown residue was diluted with 600 ml EtOAc. Followed by washing with water (300 ml) and brine (300 ml×2), dried with $Na_2SO_4$, and concentrated under reduced pressure to give a crude brown residue of the desired product.

The crude product was purified by a quick Flash Column Chromatography (~400 g $SiO_2$, 0-20% Ethyl Acetate in Hexane), 33.8 g of the desired product were isolated as a white solid in 80.2% yield and 97.51% purity.

$^1H$ NMR (600 MHz, $CDCl_3$) δ 7.16-7.10 (m, 2H), 7.09-7.01 (m, 4H), 6.96-6.92 (m, 1H), 6.80-6.73 (m, 1H), 5.78 (s, 2H), 4.02 (dd, J=8.5, 6.5 Hz, 2H), 3.86-3.69 (m, 2H), 2.51 (s, 3H).

Scale Up of the first step (95 mmol, 33.37 g)

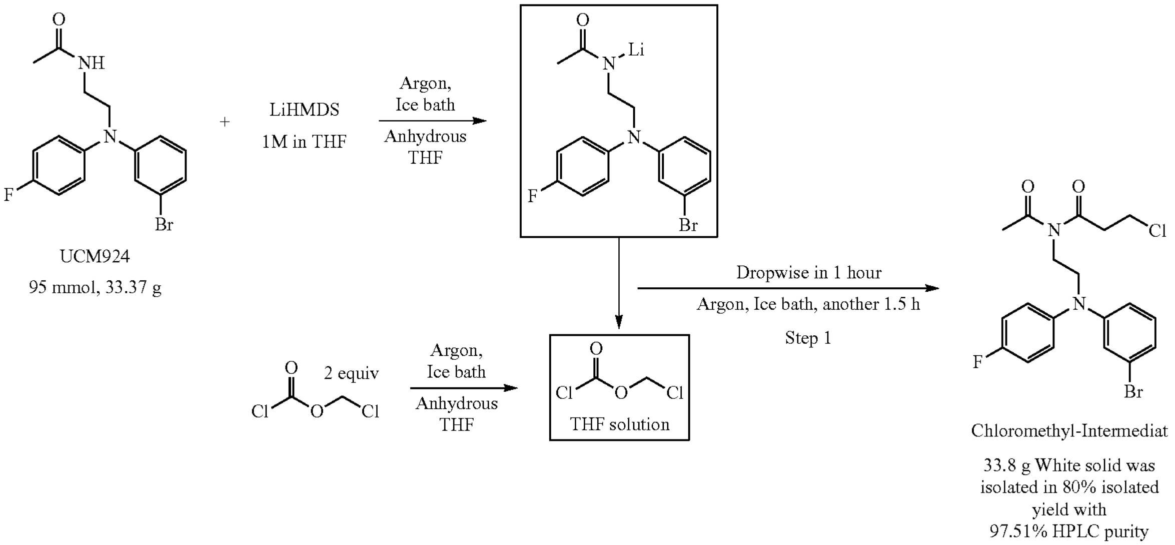

TABLE 13

| Reactant and product for the 33-gram scale up of the first step of Reaction Scheme A | | | | | | | |
|---|---|---|---|---|---|---|---|
| MATERIAL | Supplier or Lot | Mass (g) | Density (g/ml) | Volume (ml) | MW (g/mol) | Nb of Moles | Molar eq/UCM924 |
| UCM924 | NS-7-116 | 33.37 g | — | — | 351.21 | 0.095 | 1.00 eq |
| THF This solvent was dried over molecular sieves. | | | — | 380 ml | | | 11.4 Vol |
| LiHMDS (1M in THF) | Delmar | | | 100 ml | 167.33 | 0.100 | 1.05 eq |
| THF This solvent was dried over molecular sieves. | | | — | 570 ml | | | 17.1 Vol |
| Chloromethyl Chloroformate | Delmar | 24.99 g | 1.45 | 17.24 ml | 128.94 | 0.190 | 2.0 eq |
| $H_2O$ (Quench) | Deionised | | 1.00 | 50 ml | | | 1.5 Vol |
| $H_2O$ (Wash) | Deionised | | 1.00 | 300 ml | | | 9.0 Vol |
| EtOAc | Fisher | | | 600 ml | | | 18.0 Vol |
| Brine (Wash) | | | | 300 ml × 2 | | | 9.0 Vol × 2 |
| Chloromethyl Intermediate | NA | 33.8 | — | — | 443.7 | 0.0762 | 80.2% yield |

First Step of Reaction Scheme A—66 Grams

In a Flame dried 2 L RBF under argon was charged 66.0 g UCM924 and 760 ml dry THF. The reaction mixture was cooled down with an ice bath (~5° C.) under argon. Then 200 ml LiHMDS (1.06 eq, 1M in THF, new bottle) was added dropwise into the reaction mixture in around 25 min via a double tipped needle at ~5° C. under argon. The reaction mixture (Clear brown solution) was stirred at ~5° C. under argon for 2 h to complete the reaction.

Set up THE solution of Chloromethyl Chloroformate while waiting for the completion of the reaction between UCM924 and LiHMDS. In a Flame dried 3 L RBF under argon was charged 1140 ml dry THF followed by 34.48 ml Chloromethyl Chloroformate. The clear THE solution was cooled down with an ice bath (~5° C.) under argon.

The above reaction mixture (with UCM924 &LiHMDS) was transferred portion-wise into the clear THF solution of chloromethyl chloroformate in 1.5 h via a double tipped needle at ~5° C. (ice bath) under argon. The resulting mixture was kept stirring for another 2.0 h under an ice bath to complete the reaction. IPC (end of reaction) by HPLC=85.39% (8.46% UCM924+6.15% Side products).

Quench the reaction with 100 ml $H_2O$ while keeping the flask under an ice bath, the THF was removed under reduced pressure (Rotary Evaporator, <35° C.) and the brown residue was diluted with 1000 ml EtOAc and washed with water (600 ml). Followed by the aqueous phase was extracted with EtOAc (500 ml). The combined extracts were washed with brine (600 ml×2), dried with $Na_2SO_4$, and concentrated under reduced pressure to give a crude brown residue of the desired product.

The crude product was purified by a quick Flash Column Chromatography (~600 g $SiO_2$, 0-20% Ethyl Acetate in Hexane), 68.7 g desired product were isolated as a white solid in 82.4% yield and 97.1% purity.

$^1H$ NMR (600 MHz, $CDCl_3$) δ 7.14-7.09 (m, 2H), 7.09-7.00 (m, 4H), 6.96-6.92 (m, 1H), 6.78-6.75 (m, 1H), 5.78 (s, 2H), 4.02 (dd, J=8.5, 6.5 Hz, 2H), 3.85-3.76 (m, 2H), 2.51 (s, 3H).

Scale Up of the first step (187.9 mmol, 66.0 g)

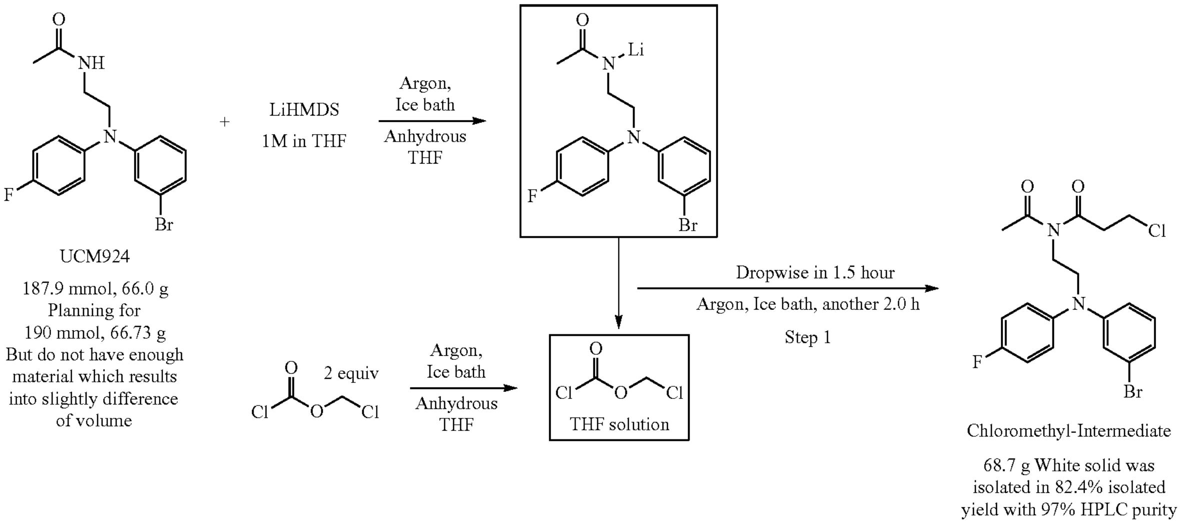

TABLE 14

Reactant and product for the 66-gram scale up of the first step of Reaction Scheme A

| MATERIAL | Supplier or Lot | Mass (g) | Density (g/ml) | Volume (ml) | MW (g/mol) | Nb of Moles | Molar eq/UCM924 |
|---|---|---|---|---|---|---|---|
| UCM924 | NS-7-116 | 66.0 g | — | — | 351.21 | 0.1879 | 1.00 eq |
| THF This solvent was dried over molecular sieves. | | | — | 760 ml | | | 11.5 Vol |
| LiHMDS (1M in THF) | Delmar | | | 200 ml | 167.33 | 0.200 | 1.06 eq |
| THF This solvent was dried over molecular sieves. | | | — | 1140 ml | | | 17.27 Vol |
| Chloromethyl Chloroformate | Delmar | 49.99 g | 1.45 | 34.48 ml | 128.94 | 0.380 | 2.02 eq |
| $H_2O$ (Quench) | Deionised | | 1.00 | 100 ml | | | 1.5 Vol |
| $H_2O$ (Wash) | Deionised | | 1.00 | 600 ml | | | 9.0 Vol |
| EtOAc | Fisher | | | 1500 ml | | | 22.7 Vol |
| Brine (Wash) | | | | 600 ml × 2 | | | 9.0 Vol × 2 |
| Chloromethyl Intermediate | NA | 68.7 g | — | — | 443.7 | 0.1548 | 82.4% yield |

Second Step of Reaction Scheme A—23 Grams

In a Flame dried 250 ml RBF under argon were charged Boc-Gly-OH 17.87 g and 110 ml dry DMF, followed by 5.61 g of KOH (ground to a whiter powder to accelerate the reaction, but still containing some small pellet pieces) at room temperature (rt). The reaction mixture was stirred at rt under argon for 3 h to complete the reaction and a clear solution was obtained.

Set up DMF solution of Chloromethyl intermediate while waiting for the completion of the reaction between Boc-Gly-OH and KOH. In a Flame dried 500 ml RBF under argon were charged 22.87 g Chloromethyl Intermediate (Batch: SL2010, 97% purity) and 110 ml of dry DMF at room temperature.

Slowly transferred the DMF solution of Boc-Gly-OK into the RBF containing Chloromethyl Intermediate in 30 mins via a double tipped needle. The resulting mixture was kept stirring at rt under argon for another 20 h to complete the reaction. (The reaction mixture became cloudy after a few hours probably due to the generated KCl not being able to completely dissolve in DMF; this is a good sign proving the reaction is working).

IPC (end of reaction) by HPLC=90.37%$_{SM+P}$ (7.37% UCM924, the HPLC was not able to separate starting material and product).

The reaction was quenched with 100 ml $H_2O$ and a white solid was precipitated from solution. Then 100 ml of ethyl acetate (EA) was added to reaction mixture, and we transferred the reaction mixture to a separation funnel. Followed by another 200 ml $H_2O$ and 500 ml EA were added to the funnel to dilute the solution. The aqueous phase was extracted with EA (300 ml). The combined extracts were washed with brine (200 ml×2), dried with $Na_2SO_4$, and concentrated under reduced pressure to give the crude desired product as viscous oil.

The crude product was purified by Flash Column Chromatography (40 g+80 g $SiO_2$ Column ×2, 0-40% EA in Hex), 27.4 g desired product was isolated as very viscous oil in 94% yield; in addition, 0.9 g of starting material (SM) were recovered in 4% yield.

$^1$H NMR (600 MHz, $CDCl_3$) δ 7.14-7.09 (m, 2H), 7.09-7.04 (m, 3H), 6.99 (t, J=2.1 Hz, 1H), 6.94 (dd, J=7.8, 1.0 Hz, 1H), 6.79 (dd, J=8.3, 1.9 Hz, 1H), 5.85 (s, 2H), 4.94 (s, 1H), 4.00 (dd, J=8.5, 6.5 Hz, 2H), 3.93 (d, J=5.7 Hz, 2H), 3.82-3.75 (m, 2H), 2.47 (s, 3H), 1.44 (s, 9H).

Scale Up of second step (50 mmol, 22.87 g)
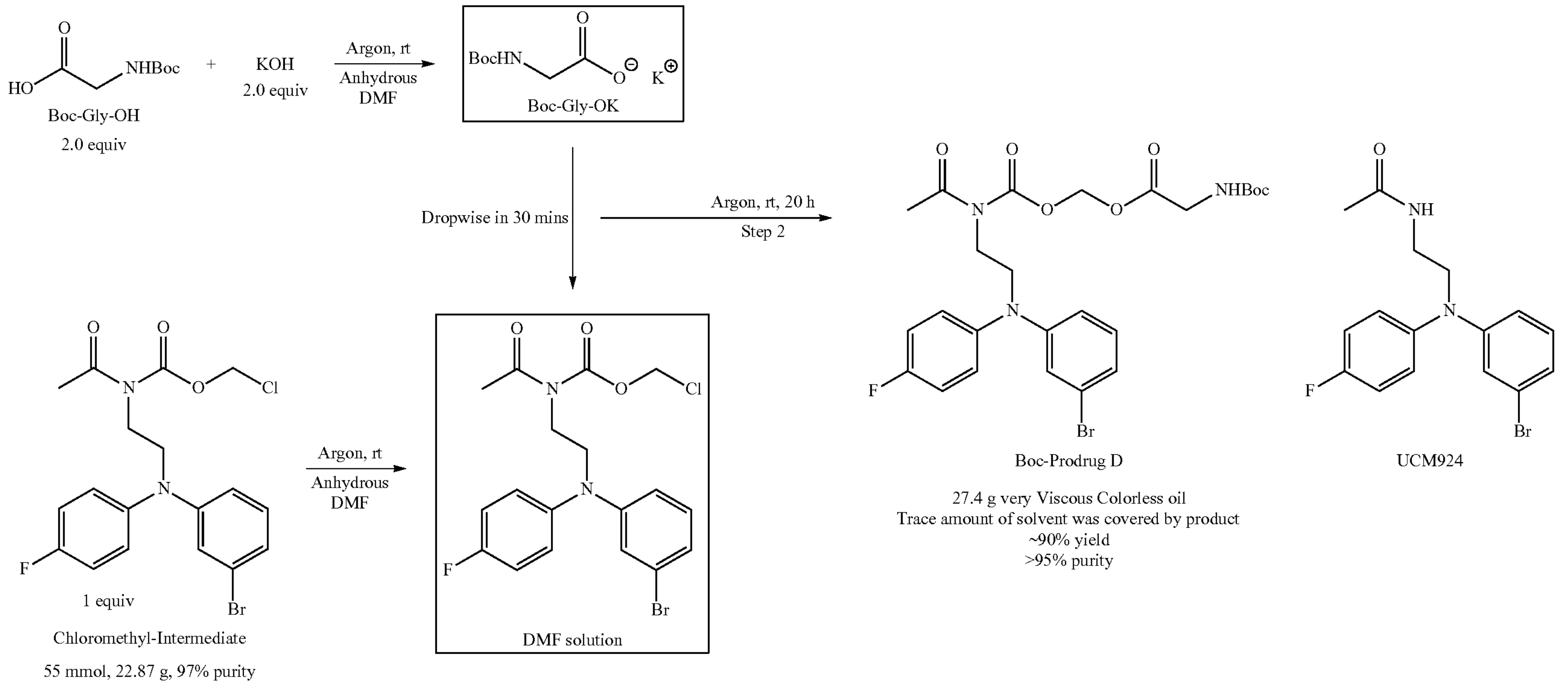

TABLE 15

Reactant and product for the 28-gram scale up of the second step of Reaction Scheme A

| MATERIAL | Supplier or Lot | Mass (g) | Density (g/ml) | Volume (ml) | MW (g/mol) | Nb of Moles | Molar eq |
|---|---|---|---|---|---|---|---|
| Chloromethyl Intermediate | SL2010 | 22.87 g | — | — | 443.69 | 0.05 | 1.00 eq |
| Boc-Gly-OH | Delmar | 17.87 g | — | — | 175.18 | 0.10 | 2.00 eq |
| KOH (99.99%) | Sigma Aldrich | 5.61 g | — | — | 56.106 | 0.10 | 2.00 eq |
| DMF dried with 4A MS | Fisher | | — | 110 ml | | | 4.8 Vol |
| DMF dried with 4A MS | Fisher | | — | 110 ml | | | 4.8 Vol |
| $H_2O$ (Quench + Wash) | Deionised | | | 300 ml | | | 13.1 Vol |
| EtOAc | Fisher | | | 900 ml | | | 39.35 Vol |
| Brine (Wash) | | | | 200 ml × 2 | | | 8.74 Vol × 2 |
| Boc-Prodrug D | | 27.4 g* | — | — | 582.42 | 0.047 | 94%* yield |

*The Product is extremely viscous and trace amounts of solvents remained in it. They were rather difficult to remove. Thus, the Isolated Yield above is a bit of higher than the actual yield which should be around 90%.

Second Step of Reaction Scheme A—50 Grams

In a Flame dried 500 ml RBF under argon was charged Boc-Gly-OH 39.08 g and 200 ml dry DMF, followed by 12.266 g of KOH (ground to a whiter powder to accelerate the reaction, but still containing small pellet pieces), at room temperature. The reaction mixture was stirred at rt under argon for 3 h to complete the reaction and a clear solution was obtained.

Set up DMF solution of Chloromethyl intermediate while waiting for the completion of the reaction between Boc-Gly-OH and KOH. In a Flame dried 1 L RBF under argon was charged 50 g Chloromethyl Intermediate (Batch: SL2018, 97% Purity) and 200 ml of dry DMF at room temperature.

Slowly transferred the DMF solution of Boc-Gly-OK into the RBF containing Chloromethyl Intermediate in 40 mins via a double tipped needle and controlled the addition rate with a pressure-equalizing dropping funnel. The resulting mixture was kept stirring at rt under argon for another 20 h to complete the reaction.

IPC (end of reaction) by HPLC=90.55%$_{SM+P}$ (5.92% UCM924, the HPLC was not able to separate SM and Product).

Cooled down the reaction mixture with an ice bath (updated procedure compared to 23 grams scale-up), quenched the reaction with 200 ml $H_2O$ and a white solid was precipitated from solution. Then 200 ml of ethyl acetate (EA) was added to reaction mixture, and we transferred the reaction mixture to a separation funnel. Followed by another 300 ml $H_2O$ and 800 ml EA were added to the funnel to dilute the solution. The aqueous phase was extracted with EA (500 ml$_{2ed}$+300 ml$_{3rd}$). The combined extracts were washed with brine (250 ml×2), dried with $Na_2SO_4$, and concentrated under reduced pressure to give the crude desired product as viscous oil.

The crude product was purified by quick Flash Column Chromatography (~700 g $SiO_2$, 4 L Hexane+2.5 L 20% EA in Hex+5.2 L 33% EA in Hex), 59.5 g desired product was isolated as a very viscous oil in 93% yield.

$^1$H NMR (600 MHz, $CDCl_3$) δ 7.14-7.10 (m, 2H), 7.09-7.03 (m, 3H), 6.99 (t, J=2.1 Hz, 1H), 6.93 (dd, J=7.8, 0.9 Hz, 1H), 6.79 (dd, J=8.3, 1.8 Hz, 1H), 5.85 (s, 2H), 4.95 (s, 1H), 4.00 (dd, J=8.4, 6.5 Hz, 2H), 3.93 (d, J=5.7 Hz, 2H), 3.80-3.75 (m, 2H), 2.47 (s, 3H), 1.44 (s, 9H).

Scale Up of the second step (109.3 mmol, 50 g)
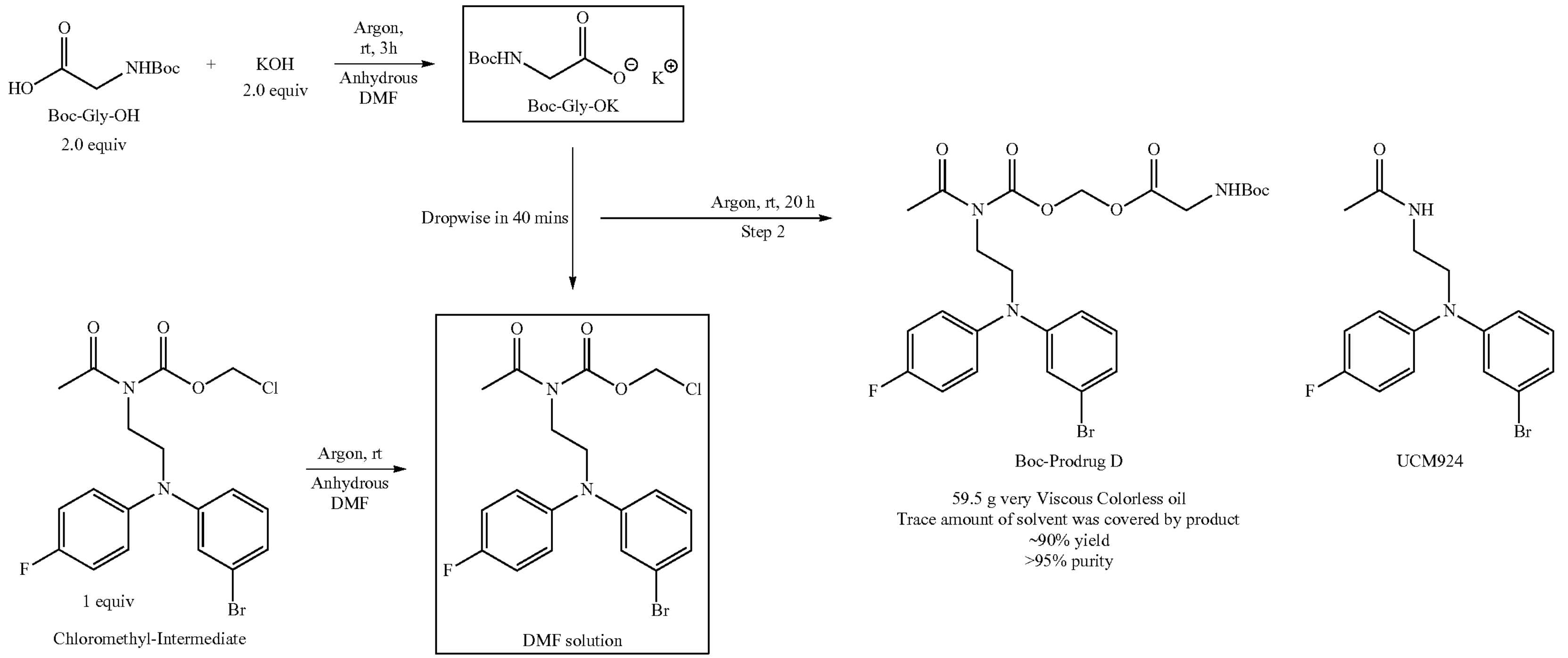
Boc-Gly-OH
2.0 equiv
KOH
2.0 equiv
Boc-Gly-OK
1 equiv
Chloromethyl-Intermediate
109.3 mmol, 50 g, 97% purity
DMF solution
Boc-Prodrug D
59.5 g very Viscous Colorless oil
Trace amount of solvent was covered by product
~90% yield
>95% purity
UCM924

TABLE 16

Reactant and product for the 50-gram scale up of the second step of Reaction Scheme A

| MATERIAL | Supplier or Lot | Mass (g) | Density (g/ml) | Volume (ml) | MW (g/mol) | Nb of Moles | Molar eq |
|---|---|---|---|---|---|---|---|
| Chloromethyl Intermediate | SL2018 | 50 g | — | — | 443.69 | 0.1093 | 1.00 eq |
| Boc-Gly-OH | Delmar | 39.08 g | — | — | 175.18 | 0.2186 | 2.00 eq |
| KOH (99.99%) | Sigma Aldrich | 12.266 g | — | — | 56.106 | 0.2186 | 2.00 eq |
| DMF dried with 4A MS | Fisher | | — | 200 ml | | | 4.0 Vol |
| DMF dried with 4A MS | Fisher | | — | 200 ml | | | 4.0 Vol |
| $H_2O$ (Quench + Wash) | Deionised | | | 500 ml | | | 10.0 Vol |
| EtOAc | Fisher | | | 1800 ml | | | 36 Vol |
| Brine (Wash) | | | | 250 ml × 2 | | | 5.0 Vol × 2 |
| Boc-Prodrug D | | 59.5 g* | — | — | 582.42 | 0.047 | 93%* yield |

*The Product is extremely viscous and trace amounts of solvents remained in it. They were rather difficult to remove. Thus, the Isolated Yield above is a bit of higher than the actual yield which should be around 90%.

Example 5—Best Mode Synthesis of UCM924 and Prodrug D

We summarize below the best method for the synthesis of UCM924 described in Example 1 and the best synthesis of Prodrug D according to Examples 3 and 4.

The best method for the synthesis of UCM924 is according to Scheme 1 and the best method for the synthesis of Prodrug D starting from UCM924 is according to Scheme 2.

These methods were scaled up as shown below. Steps 1~4 are the synthesis of UCM924, while steps 5-7 are the synthesis of Prodrug D from UCM924.

Scheme 1

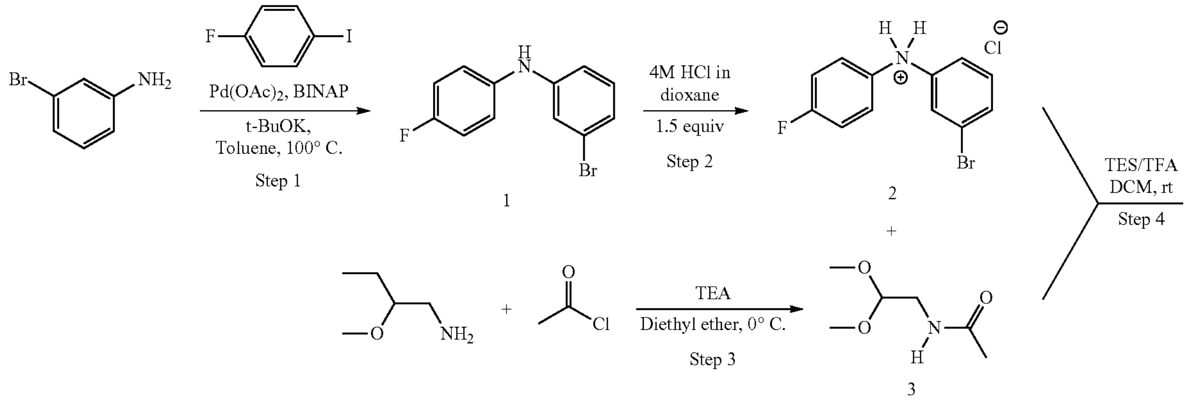

Scheme 2

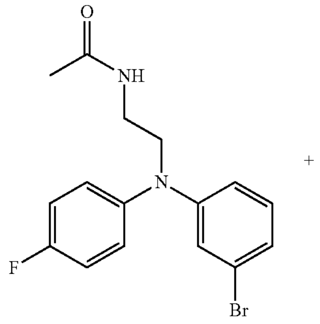

UCM924

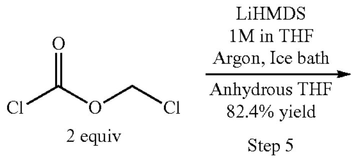

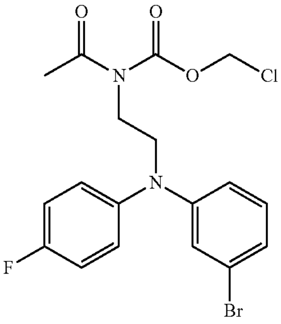

4

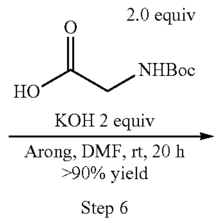

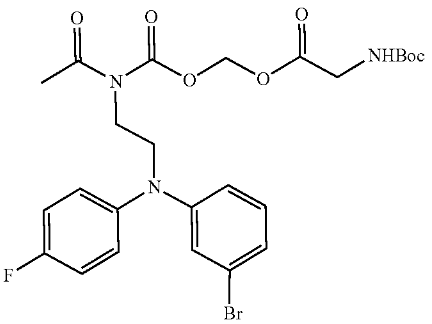

Boc-Prodrug D

5

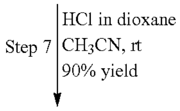

-continued

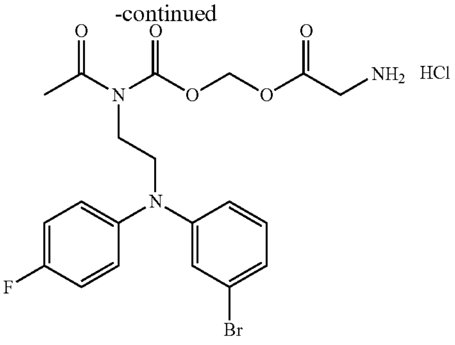

UCM924-Prodrug D

Step 1—Synthesis of 3-bromo-N-(4-fluorophenyl)aniline

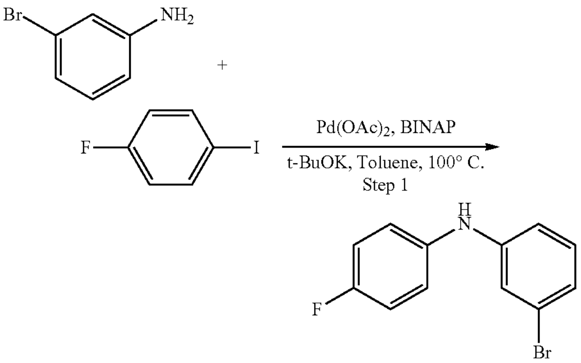

Condition for 20 g Scale:

In an Oven-dried flask and under argon atmosphere, a mixture of 3-Bromoaniline. (11.1 ml, 100 mmol, 1 equiv, 98%), 4-Fluoroiodobenzene (12.11 ml, 105 mmol, 1.05 equiv, 99%), rac-BINAP (3.11 g, 5 mmol, 0.05 equiv, 97%) and $Pd(OAc)_2$ (900 mg, 4 mmol, 0.04 equiv, 98%) was dissolved in dry and degassed toluene (200 mL) and the mixture was stirred for 30 mins at room temperature. Then KOtBu (16.83 g, 150 mmol, 1.5 equiv, 98%) was added and the mixture was heated to 100° C. for 6 h. After cooling to rt, the mixture was filtered through a short pad of Celite to remove the insoluble impurity and washed with 20% EtOAc in Hexane. The organic solvents were evaporated under vacuum, the residue was purified by Flash Column Chromatography ($SiO_2$, 0-5% EtOAc in Hexane) to give the desired product 19 g as brown oil in 71% yield.

$^1H$ NMR (600 MHz, Acetone-d6): δ 7.54 (s, 1H), 7.21 (dd, J=8.8, 4.7 Hz, 2H), 7.19-7.12 (m, 2H), 7.11-7.09 (m, 2H), 7.01 (dd, J=8.2, 1.7 Hz, 1H), 6.96 (dd, J=7.9, 1.7 Hz, 1H).

Condition for 1 Kg Scale:

A stirred solution of 3-Bromoaniline (1.0 kg, 1.0 eq, 5812.9 mmol) in toluene (15.0 L),4-Fluoroiodobenzene (1.55 kg, 1.2 eq, 6972.9 mmol), palladium acetate (52.20 g, 0.04 eq, 232.51 mmol) and BINAP (180.98 g, 0.05 eq, 290.64 mmol) was prepared. The reaction mixture was degassed with nitrogen for 30 minutes. Potassium tert-butoxide (652.26 g, 1.0 eq, 5812.9 mmol) was added at RT. Reaction mixture stirred for 8 hr at 100° C. Monitor the progress of reaction by TLC [mobile phase: 20% ethyl acetate in n-heptane]. The reaction mixture cooled at RT, filtered through hyflow bed, and washed with 20% ethyl acetate in n-heptane (4.0 L). Filtrate was concentrated under vacuum at 50° C. to get crude compound. Crude was purified by column chromatography using 20 times silica gel. Crude was purified through column chromatography with use of ethyl acetate in n-heptane (0-25%) to afford titled compound (1.35 kg) as an oily.

Purity by HPLC=97.41%

$^1$H NMR (300 MHz, DMSO): δ 8.35 (s, 1H), 7.15 (m, 6H), 6.98 (m, 1H), 6.92 (d, 1H).

Step 2—Synthesis of 3-bromo-N-(4-fluorophenyl)benzene-aminium chloride

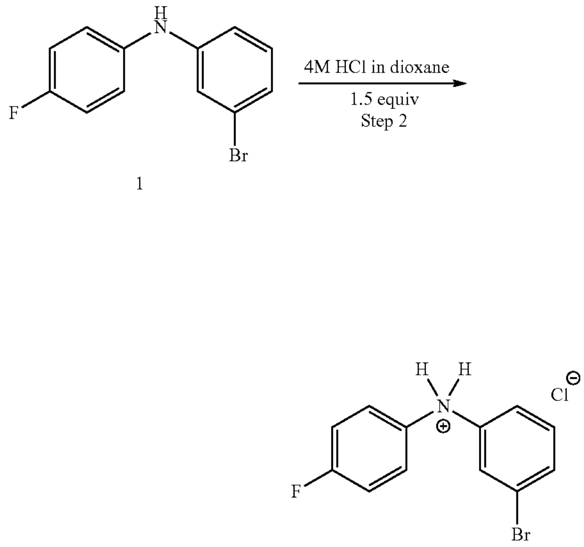

1

2

Condition for 80 g Scale

Treatment of the 3-bromo-N-(4-fluorophenyl)aniline (107 g) with 1.5 equiv of HCl (4 M in dioxane) and kept stirring at rt for 2 hours to precipitate the crude HCl salt as pale brown solid. Then dioxane was evaporated under vacuum and the residue was re-dissolved with 20% diethyl ether in Hexane and kept stirring at room temperature for another 1 to 2 hours to precipitate the desired product as fine white or pale brown solid which was filtrated to give the desired product 80.45 g with >99% purity.

$^1$H NMR (600 MHz, DMSO-d6): δ 7.16-7.08 (m, 6H), 6.97 (d, J=8.2 Hz, 1H), 6.91 (d, J=7.8 Hz, 1H).

Condition for 1 Kg Scale

Methanolic HCl (33%, 3.3 L) was added slowly in precooled Oily 3-bromo-N-(4-fluorophenyl)aniline (1.1 kg, 1.0 eq, 4133.63 mmol) at (5-10° C.). Reaction mixture was stirred for 2 hours at (5-10° C.). Solid precipitate was collected by filtration. Precipitate washed with n-heptane (0.5 L) and dried at RT (25° C.-30° C.) for 16 hours to afford titled compound (0.93 kg) as a light grey solid.

Purity=97.83%.

$^1$H NMR (300 MHz, DMSO): δ 7.14 (m, 6H), 6.97 (m, 1H), 6.91 (d, 1H).

Step 3-Synthesis of N-(2,2-dimethoxyethyl)acetamide

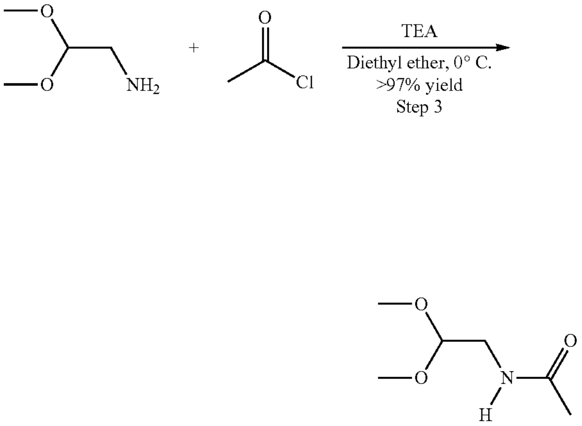

To a solution of 2,2-Dimethoxyethylamine (400 mmol, 44.93 ml) and triethylamine (420 mmol, 1.05 equiv, 58.54 ml) in diethyl ether (750 ml) were slowly dropwise acetic chloride (420 mmol, 1.05 equiv, 30 ml) at 0° C. The mixture was stirred and slowly warmed up to room temperature for 1.5 hours to complete the reaction. The mixture was filtered through a short pad of Celite to remove the precipitated white salt and washed with 300 ml of diethyl ether. The organic solvents were evaporated under vacuum to give the desired product N-(2,2-dimethoxyethyl)acetamide 57.1 g as colorless (or pink) oil in 97% yield which was used for next step without any further purification.

$^1$H NMR (600 MHz, $CDCl_3$): δ 5.79 (s, 1H), 4.38 (t, J=5.2 Hz, 1H), 3.40 (d, J=7.4 Hz, 2H), 3.40 (s, 6H), 2.00 (s, 3H).

Step 4—Synthesis of UCM924

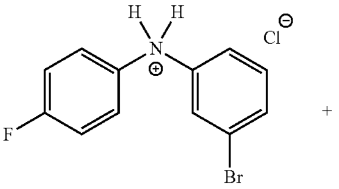

2

-continued

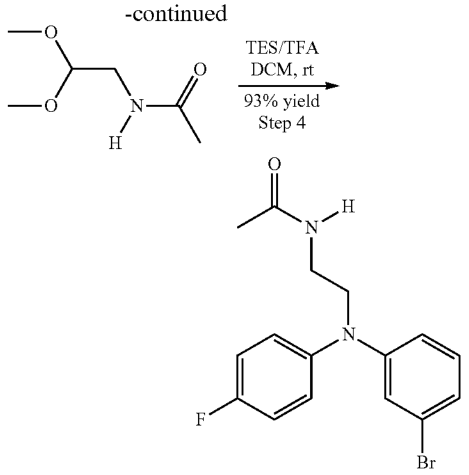

UCM 924

To a solution of 3-bromo-N-(4-fluorophenyl)aniline HCl salt (140 mmol, 42.36 g) and N-(2,2-dimethoxyethyl)acetamide (1.4 equiv, 196 mmol, 28.84 g) in DCM (250 ml) at 0° C., were slowly added trifluoroacetic acid (TFA, 4 equiv, 560 mmol, 42.95 ml) in around 10 mins, then triethylsilane (TES, 2.5 equiv, 350 mmol, 55.9 ml) was slowly dropwise in 10 mins with dropping funnel. The resulting mixture was stirred at 0° C. for 10 mins and room temperature for another 3.5 hours to complete the reaction. The reaction was cooled at 0° C. and carefully neutralized with saturated solution of $NaHCO_3$ then diluted with EtOAc and $H_2O$. The aqueous layer was extracted with EtOAc (3×) and the combined organic phases were washed with $H_2O$ and brine, dried over $Na_2SO_4$, and concentrated under reduce pressure to give the crude product as brown solid which was further recrystallized from DCM and Hexane to furnish 41.7 g of the desired UCM924 as pale brown solid in 85% yield.

$^1$H NMR (600 MHz, Acetone) δ 7.31-7.28 (m, 3H), 7.20 (t, J=8.7 Hz, 2H), 7.11 (t, J=8.1 Hz, 1H), 6.98 (s, 1H), 6.91 (d, J=7.9 Hz, 1H), 6.83 (dd, J=8.4, 2.2 Hz, 1H), 3.81 (t, J=7.0 Hz, 2H), 3.42 (dd, J=13.5, 6.5 Hz, 2H), 1.86 (s, 3H).

Step 5—Synthesis of chloromethyl acetyl(2-((3-bromophenyl)(4-fluorophenyl)amino)ethyl)carbamate In a Flame dried 2 L RBF under argon was charged 66.0 g UCM924 and 760 ml dry THF. The reaction mixture was cooled down with an ice bath (~5° C.) under argon. Then 200 ml LiHMDS (1.06 eq, 1M in THF, new bottle) was added dropwise into the reaction mixture in around 25 min via a double tipped needle at ~5° C. under argon. The reaction mixture (Clear brown solution) was stirred at ~5° C. under argon for 2 h to complete the reaction.

Set up THF solution of Chloromethyl Chloroformate while waiting for the completion of the reaction between UCM924 and LiHMDS. In a Flame dried 3 L RBF under argon was charged 1140 ml dry THF followed by 34.48 ml Chloromethyl Chloroformate. The clear THE solution was cooled down with an ice bath (~5° C.) under argon.

The above reaction mixture (with UCM924 &LiHMDS) was transferred portion-wise into the clear THF solution of chloromethyl chloroformate in 1.5 h via a double tipped needle at ~5° C. (ice bath) under argon. The resulting mixture was kept stirring for another 2.0 h under an ice bath to complete the reaction. IPC (end of reaction) by HPLC=85.39% (8.46% UCM924+6.15% Side products).

Quench the reaction with 100 ml $H_2O$ while keeping the flask under an ice bath, the THF was removed under reduced pressure (Rotary Evaporator, <35° C.) and the brown residue was diluted with 1000 ml EtOAc and washed with water (600 ml). Followed by the aqueous phase was extracted with EtOAc (500 ml). The combined extracts were washed with brine (600 ml×2), dried with $Na_2SO_4$ and concentrated under reduced pressure to give a crude brown residue of the desired product. The crude product was purified by a quick Flash Column Chromatography (~600 g $SiO_2$, 0-20% Ethyl Acetate in Hexane), 68.7 g desired product was isolated as a white solid in 82.4% yield and 97.1% purity.

$^1$H NMR (600 MHz, $CDCl_3$) δ 7.14-7.09 (m, 2H), 7.09-7.00 (m, 4H), 6.96-6.92 (m, 1H), 6.78-6.75 (m, 1H), 5.78 (s, 2H), 4.02 (dd, J=8.5, 6.5 Hz, 2H), 3.85-3.76 (m, 2H), 2.51 (s, 3H).

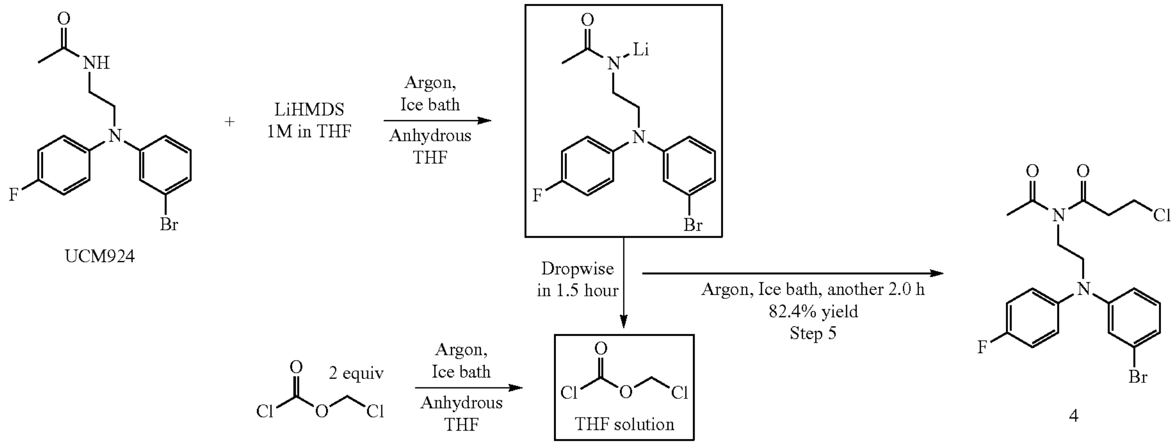

Step 6—Synthesis of Boc-UCM924—Prodrug D

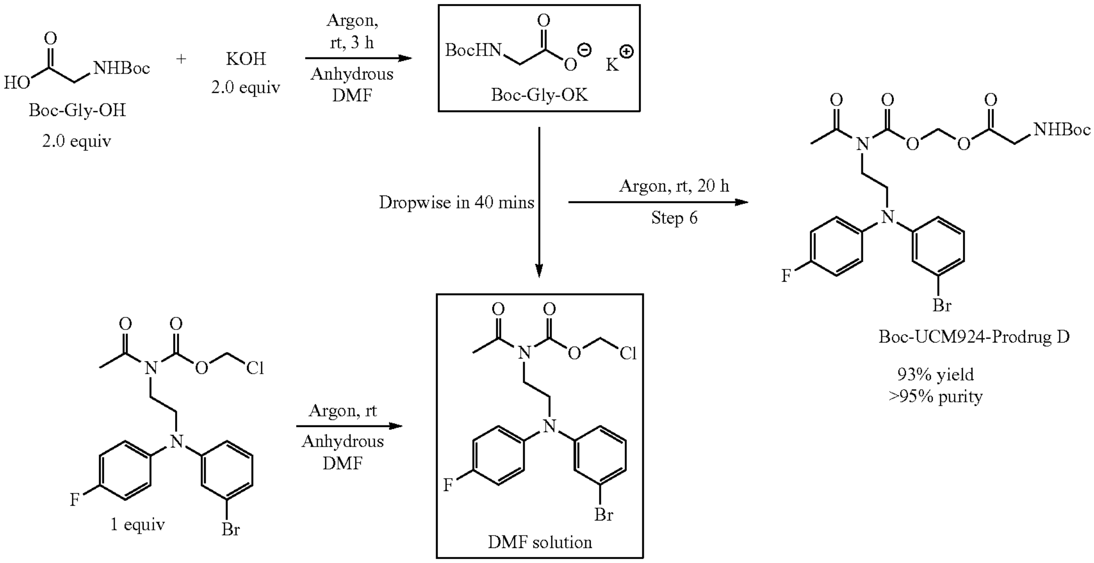

In a Flame dried 500 ml RBF under argon was charged Boc-Gly-OH 39.08 g and 200 ml dry DMF, followed by 12.266 g of KOH (ground to a white powder to accelerate the reaction, but still containing small pellet pieces) was added at room temperature. The reaction mixture was stirred at rt under argon for 3 h to complete the reaction and a clear solution was obtained.

Set up DMF solution of Chloromethyl intermediate while waiting for the completion of the reaction between Boc-Gly-OH and KOH. In a Flame dried 1 L RBF under argon was charged 50 g Chloromethyl Intermediate (Batch: SL2018, 97% Purity) and 200 ml of dry DMF at room temperature. Slowly transferred the DMF solution of Boc-Gly-OK into the RBF containing Chloromethyl Intermediate in 40 mins via a double tipped needle and control the addition rate with a Pressure-equalizing dropping funnel. The resulting mixture was kept stirring at rt under argon for another 20 h to complete the reaction.

IPC (end of reaction) by HPLC=90.55%$_{SM+P}$ (5.92% UCM924, the HPLC was not able to separate SM and Product).

Cooling down the reaction mixture with an ice bath (updated procedure compared to SL2024), quench the reaction with 200 ml $H_2O$ and white solid was precipitated from solution. Then 200 ml of Ethyl Acetate was added to reaction mixture and transfer the reaction mixture to a separation funnel. Followed by another 300 ml $H_2O$ and 800 ml EA were added to the funnel to dilute the solution. The aqueous phase was extracted with EtOAc (500 ml$_{2ed}$+300 ml$_{3rd}$). The combined extracts were washed with brine (250 ml×2), dried with $Na_2SO_4$, and concentrated under reduced pressure to give the crude desired product as viscous oil.

The crude product was purified by a quick Flash Column Chromatography (~700 g $SiO_2$, 4 L Hexane+2.5 L 20% EA in Hex+5.2 L 33% EA in Hex), 59.5 g desired product was isolated as a very viscous oil in 93% yield.

$^1$H NMR (600 MHz, $CDCl_3$) δ 7.14-7.10 (m, 2H), 7.09-7.03 (m, 3H), 6.99 (t, J=2.1 Hz, 1H), 6.93 (dd, J=7.8, 0.9 Hz, 1H), 6.79 (dd, J=8.3, 1.8 Hz, 1H), 5.85 (s, 2H), 4.95 (s, 1H), 4.00 (dd, J=8.4, 6.5 Hz, 2H), 3.93 (d, J=5.7 Hz, 2H), 3.80-3.75 (m, 2H), 2.47 (s, 3H), 1.44 (s, 9H).

Step 7—Synthesis of Prodrug D

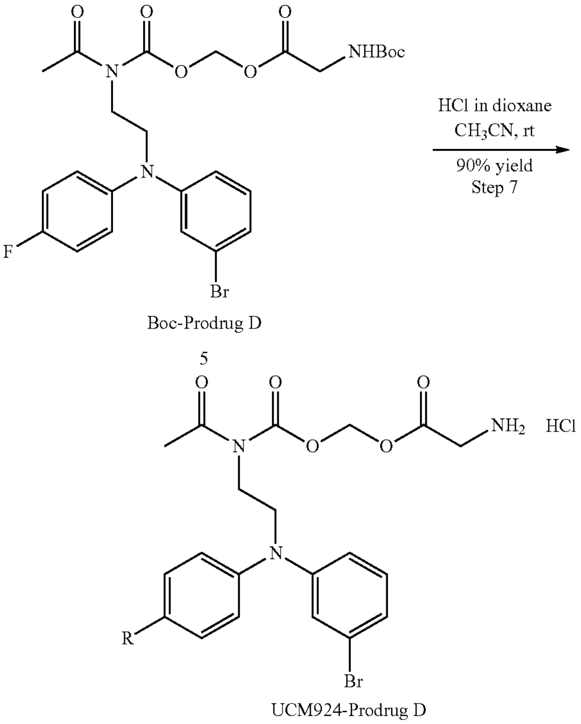

To a $CH_3CN$ (500 ml) solution of Boc-Prodrug D (19.8 g, 92.9% purity, 31.58 mmol, 1.0 equiv) was added HCl solution (4M in dioxane, 79 ml, 316 mmol, 10equiv) at room temperature. The mixture was stirred at rt for 40 min to complete the reaction. The organic solvents were evaporated under vacuum, the residue was suspended in trace amount of EtOAc, and diethyl ether was added to induce precipitation of the desired HCl salt as white solid (or very viscous colorless oil was sticky on the flask), then remove the supernatant. This procedure was repeated for three times. Treatment of the desired white solid (or very viscous colorless oil) with high vacuum to give the final product as a white foam solid 14.7 gin 89.7% yield.

$^1$H NMR (600 MHz, DMSO-d6): δ 8.46 (s, 3H), 7.28-7.22 (m, 4H), 7.16 (t, J=7.9 Hz, 1H), 6.96 (s, 1H), 6.96 (d, J=7.8 Hz, 1H), 6.80 (d, J=7.9 Hz, 1H), 5.88 (s, 2H), 3.91 (s, 2H), 3.89-3.85 (m, 2H), 3.81-3.74 (m, 2H), 2.38 (s, 3H).

MS: Calcd. For $C_{20}H_{22}BrFN_3O_5^+$ [M−Cl$^-$]: 482.07; Found: 482.43.

Condition for 150 g Scale

To a $CH_3CN$ (25Vol, 3 800 ml) solution (the solution is turbid) of Boc-Prodrug D (152 g, HPLC purity=~98.3%, 0,26098, 1.0 eq), in a round bottom flask 12 L three neck, was added slowly (around ~60 min) HCl solution (4M in dioxane, 652.45 ml, 2,6098, 10.0 eq) at RT. At the end of addition, the mixture was already a clear pinkish solution. The mixture was stirred at RT for ~30 min (max 1 h) to complete the reaction. After 30 min IPC (end of reaction by HPLC)=97.88% (starting material was non-detected), once the reaction was complete the reaction mixture became a clear purple-pinkish solution. When the reaction is finished need to proceed immediately with the work-up because the HCl solution start giving the mixture a pinkish-purple colour and with time becomes even darker! The reaction mixture was concentrated on the rotavap in a 3 L round bottom flask to give a burgundy-purple sticky and dense oil, this residue was dissolved in a minimum quantity of EtOAc (1.5Vol, 228 ml), the solution was stirred under a strong flux of $N_2$ for about 30-60 min until became very fine white suspension then diethyl ether (14Vol, ~2 128 ml) was added slowly over ~60 min to induce precipitation of the desired HCl salt as a white solid. After stirring for about 30-60 min the suspension was filtered on a Buchner and wash with 2×152 ml (2×1Vol) diethyl ether. The wet cake was dried under vacuum and nitrogen at RT for ~4 days. White fine solid, m=130.71 g, Yield=97%, HPLC purity=98.24%; Total Yield=97%; The product was stored in the freezer at −20° C. and handled under nitrogen.

Example 6—In Vivo Studies on Neuropathic Pain

Materials and Methods

Animals

Experiments were performed in male Sprague-Dawley rats (body weight: 250-300 g; Charles River Laboratories, St. Constant, QC, Canada) and adult male C57BL mice (body weight: 25-30 g; inbred). All animals were housed in small groups at a constant temperature of 22° C., with food and water provided ad libitum, and maintained under a 12 h light/dark cycle (lights on at 7:00 AM; lights off at 7:00 PM). All experimental procedures were conducted in accordance with the guidelines of the Canadian Council on Animal Care, and the protocols were approved by the Animal Care Committee at McGill University.

Drugs and Pharmacological Treatments

The different prodrug compounds as synthesized in Example 2 were tested and compared with Gabapentin (150 mg/kg, purchased from Sigma Aldrich, US). Prodrug was dissolved in saline, water, or a vehicle composed of 40% PEG400 and 60% water. Gabapentin was dissolved in a vehicle composed of 40% PEG400 and 60% water. All drugs (doses see the procedure descriptions below) were administrated per os (gavage) through a curved feeding tube (20 G for rats and 22 G for mice) at the beginning of the experiment unless otherwise specified. The dose of prodrug was chosen based on its pharmacokinetic properties, and the doses of Gabapentin were chosen from literature (Lopez-Canul, Palazzo et al. 2015).

Spared Nerve Injury of the Sciatic Nerve (SNI)

Spared nerve injury was performed according to the method of (Decosterd I and Woolf CJ, 2000), see also Lopez-Canul et al., 2015. Rats and mice were anesthetized with isoflurane. The sciatic nerve was exposed at mid-thigh level distal to the trifurcation and freed of connective tissue; the three peripheral branches (sural, common peroneal, and tibial nerves) of the sciatic nerve were exposed without stretching nerve structures. Both tibial and common peroneal nerves were ligated and transected together. Tactile allodynia was absent in healthy (pre-surgery) and sham rats, and the mechanical withdrawal threshold in rats before SNI (pre-surgery) or sham was very close to the cutoff of dynamic plantar aesthesiometer (30 g) (Ugo Basile, Varese, Italy).

Measurement of Mechanical Allodynia in Rats

On day 14 after surgery, individual rats were placed in a test chamber (clear plastic wire mesh-bottomed cage) and allowed to acclimatize for 30 to 40 minutes. Von Frey filaments (Stoelting, Wood Dale, IL) were used to measure the 50% paw withdrawal threshold using the up-and-down method reported by {Chaplan, 1994 #399}. A series of filaments, starting with one that had a buckling weight of 2 g, were applied in a consecutive sequence on the left hind paw with a pressure causing the filament to buckle. Lifting of the paw indicated a positive response and prompted the use of the next strongest filament, whereas absence of paw withdrawal after 5 seconds indicated a negative response and prompted the next filament of increasing weight. This paradigm continued for 4 more measurements after the initial change of the behavioral response or until 5 consecutive negative or 4 consecutive positive responses. Based on observations on normal, unoperated, and sham-operated rats, the cutoff value of 15 g was selected as the upper limit for testing because stiffer hairs tended to raise the entire limb rather than to buckle, substantially changing the nature of the stimulus. The resulting scores were used to calculate the 50% response threshold using the formula proposed by Dixon. Allodynia was considered to be present when paw withdrawal thresholds were <4 g, and drugs raising this threshold were considered antiallodynic {Lopez-Canul, 2015}. Accordingly, all nerve ligated rats were verified to be allodynic, responding to a stimulus of <4 g. Rats without mechanical allodynia were excluded. After the determination of the basal response, allodynia was assessed at baseline, 0.5, 1, 1.5, 2, 2.5, 3, 4, 5, 6, 7, and 8 hours post-administration for each treatment described below. Groups of 5 to 6 rats per treatment were used, with each animal being used for 1 treatment only. Spared nerve injury rats were randomly assigned to receive a single p.o. administration of prodrug (50, 100, 150, or 300 mg/kg) dissolved in saline (1.2 mL), prodrug crystal (50 or 100 mg/kg) suspended in 40% PEG400 and 60% water, or prodrug (50 mg/kg) dissolved in 40% PEG400 and 60% water. The effects were compared with those produced by VEH administration.

Experimental Design and Statistical Analyses

Data analysis was performed by using the Graphpad® Prism8 (Graphpad Software). One-way ANOVA and Two-way ANOVA were used to analyze data (with factors as indicated in Results). In two-way ANOVA, post-hocanalyses were performed using the Bonferroni comparisons. All data are expressed as mean±SEM. $P<0.05$ was considered significant.

Results

Different Compounds Increase Paw Withdrawal Threshold after SNI Surgery

Neuropathic pain was induced in rats using SNI, animals were tested at baseline prior to SNI/sham procedure and at day 15 post-surgery (time 0) using von Frey's filaments and after the per os (gavage) administration of different prodrugs at time 0.5 h, 1, 2, 3, 4, 5, 6, 7 and 8 hour.

Treatment with prodrugs A, B, C and D (50 mg/kg) significantly increased the withdrawal threshold in SNI rats (n=8-9) over time, demonstrating an anti-allodynic effect of the compounds (Two-way ANOVA: treatment: $F_{5,380}=16.62$, $p<0.0001$; time: $F_{9,380}=25.62$, $p<0.000$; interaction treatment×time: $F_{45,380}=4.03$, $p<0.0001$) (FIG. 1A). Bonferroni post-hoc comparisons revealed a significant difference in withdrawal threshold between SNI rats treated with prodrug D, after 1 hour (p=0.05), and more important after 3, 4, 5 and 6 hours ($p<0.0001$) relative to SNI rats treated with vehicle (veh).

Prodrugs A and B have also a better response than veh after one hour ($p<0.001$ and $p<0.0001$), however these prodrugs are lipophilic, while prodrug D is hydrophilic, making prodrug D more hydrosoluble and "druggable" (FIG. 1A).

Importantly, all the prodrugs have a better antiallodynic effects relative to the precursor UCM924 (FIG. 1A). In particular, Bonferroni post-hoc analysis demonstrates that prodrug D is also superior to its precursor UCM924 at hour 5 ($p<0.001$) and hour 6 ($p<0.0001$).

Figure 1B:
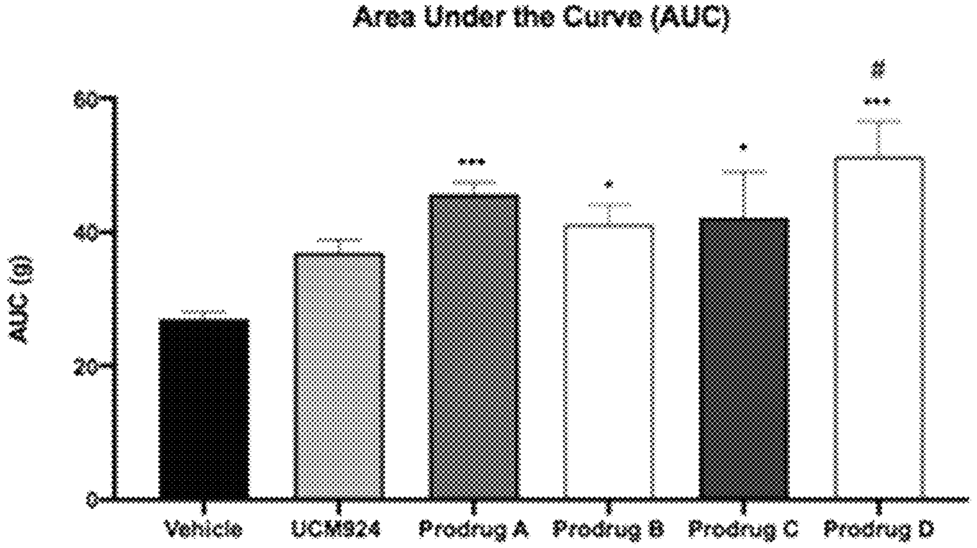

Next, the Area Under the Curve (AUC) was analyzed, and the one-way ANOVA showed a difference among treatments ($F_{5,46}=9.162$, $p<0.0001$). Bonferroni multiple comparison test showed a difference between prodrug D and vehicle ($p<0.0001$), while prodrug B and C vs. vehicle showed a $p<0.05$, and prodrug A vs. vehicle a $p<0.01$ (FIG. 1B).

Prodrug D showed a significant superior effect relative to UCM924 (p=0.015, t-test), demonstrating an improved efficacy of the prodrug compared to its parent compound.

Figure 2A:
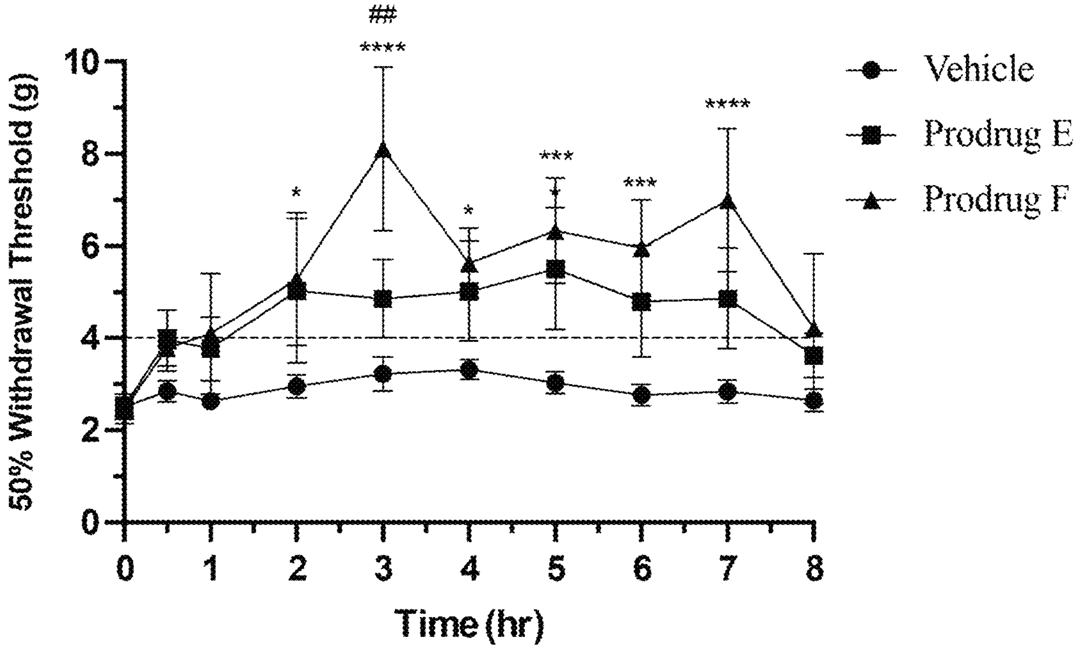
FIGS. 2A and 2B show the effect of Prodrugs E and F on mechanical allodynia in neuropathic rats.

Finally, two other amino acid prodrugs (E, F) were synthetized and tested. Two-way ANOVA showed: treatment: $F_{2,380}=43.43$, $p<0.0001$; time: $F_{2,380}=5.279$, $p<0.0001$; interaction treatment×time: $F_{18,380}=1.63$, $p<0.049$) (FIG. 2A). Bonferroni post-hoc comparisons revealed a significant difference in withdrawal threshold between SNI rats treated with prodrug F vs. vehicle, in particular after 3 hours (p=0.05), and after 5, 6 and 7 hours ($p<0.0001$) relative to SNI rats treated with veh. Prodrug E was also different from vehicle (p=0.04), but post-hoc analysis revealed a difference only at hour 2, 4 and 5 ($p<0.05$).

Figure 2B:
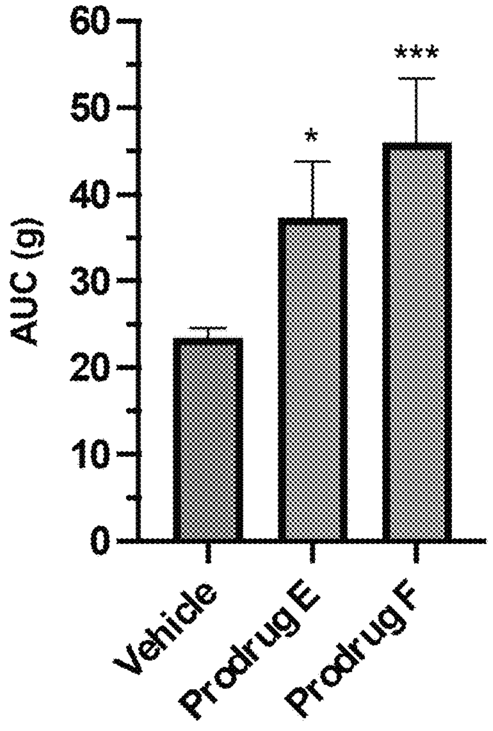

The Area Under the Curve (AUC) was next analyzed, and the one-way ANOVA showed a difference among treatments ($F_{2,38}=11.09$, $p<0.001$). Bonferroni multiple comparison test showed a difference between prodrug F and vehicle ($p<0.001$), while prodrug E vs. vehicle showed a $p<0.05$ (FIG. 2B).

Results on Prodrug D-2

Figure 3A:
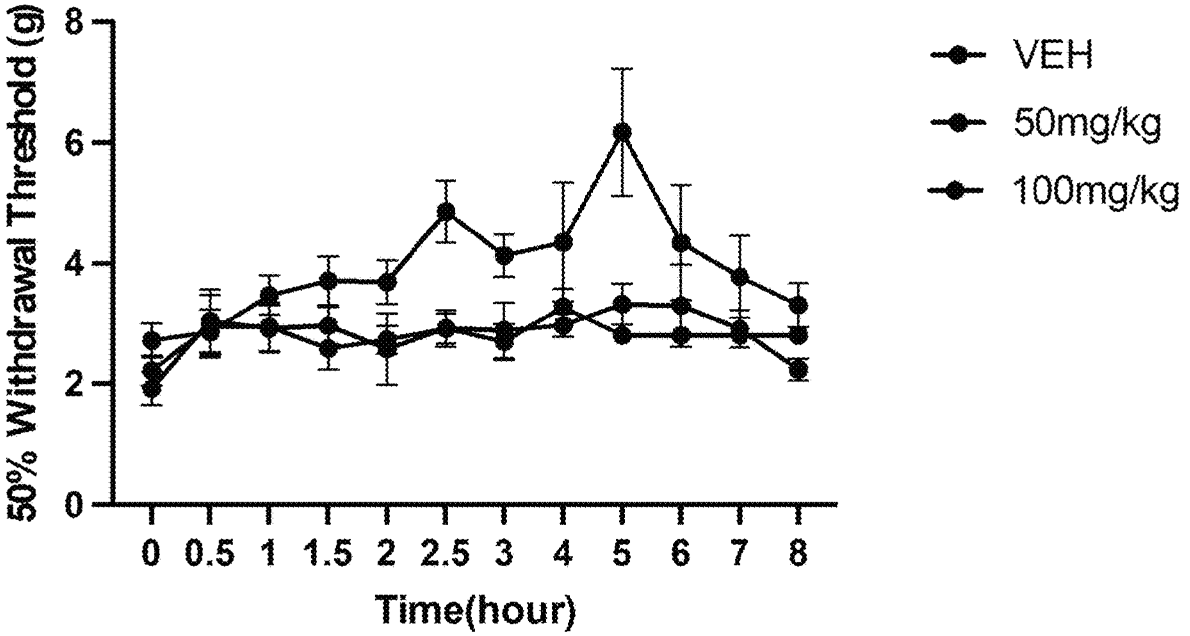
FIGS. 3A and 3B show the effect of Prodrug D-2 on mechanical allodynia in neuropathic rats.

An analog of prodrug D (prodrug D-2, which differs from prodrug D only in the acid moiety) was tested in thein vivo SNI model. Surprisingly, prodrug D-2 was not effective at the dose of 50 mg/kg, but only at 100 mg/kg, Two-way ANOVA: treatment: $F_{2,14}=13.34$, $p<0.001$; time: $F_{5,77}=2.89$, $p<0.05$; interaction treatment×time: $F_{22,154}=1.14$, p=n.s) (FIG. 3A).

Figure 3B:
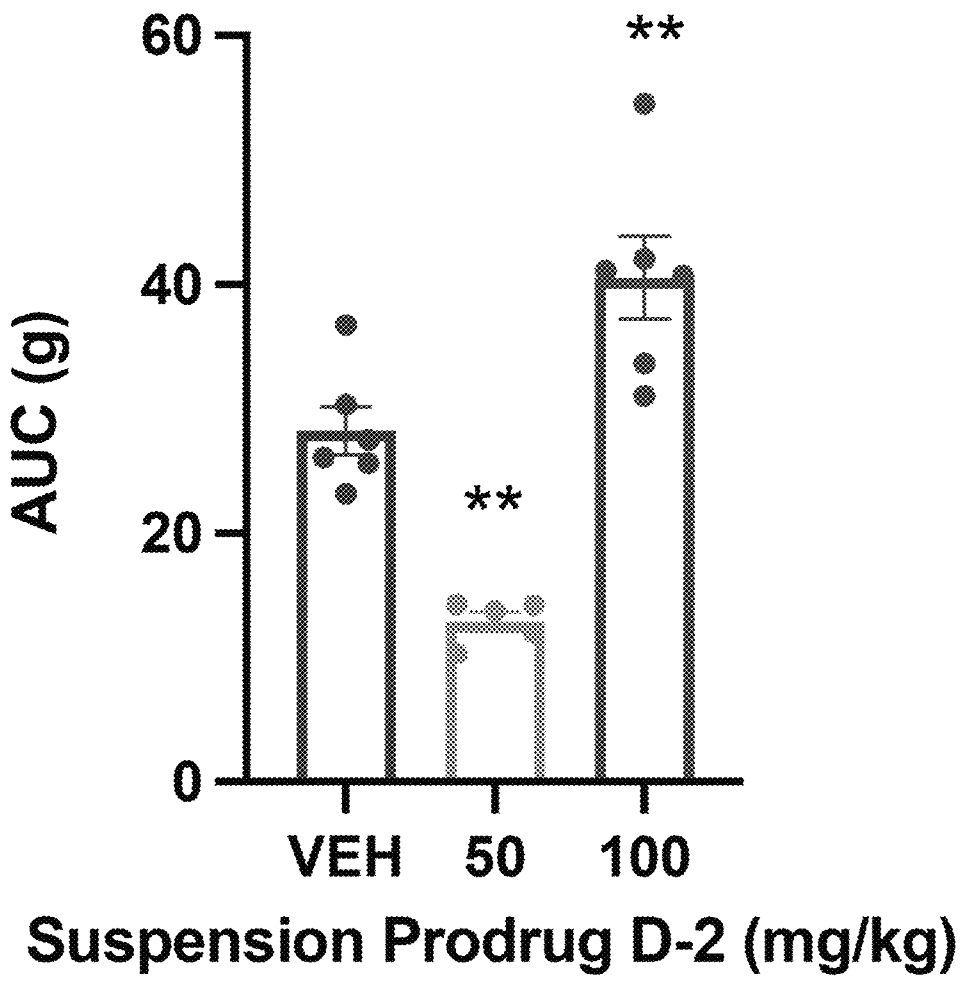

Following the AUC, at the dose of 50 mg/kg, prodrugD-2 surprisingly had a significant pro-nociceptive effect ($p<0.01$), while only at the dose of 100 mg/kg had a modest, but significant anti-nociceptive effect ($p<0.01$). (FIG. 3B).

This poor effect of Prodrug D-2 demonstrate that the efficacy of Prodrug A, B, C, D, E and F was not obvious.

Example 7—Solubility and Stability of Prodrug D

The solubility and stability of Prodrug D as synthesized in Example 2 were studied.

Prodrug D was found to have a solubility of more than 150 mg/ml in water and more than 125 mg/ml in a PEG400: water 40%: 60% mixture.

For this test, we used HPLC with different solvent systems. The details were as follow:

Column: Kromasil eternity-5-C18;
Dim: 4.6×150 mm;
1.5 ml/min;
Run time: 20 mins;
Injection volume: 10-20 μl;
254 nm;
The HPLC methods were used:

HPLC Method 1): 0.1% formic acid in HPLC water gradually to $CH_3CN$ for 15 mins then 100% $CH_3CN$ for 5 mins HPLC Method 2): 0.1% TFA in HPLC water gradually to $CH_3CN$ for 15 mins then 100% $CH_3CN$ for 5 mins Prodrug D was more stable in the conditions used in Method 2). Therefore, after initial assessment, this method was used for the remaining tests.

Prodrug D or UCM924 (comparator) were dissolved in the different solvents listed in the table below and, after the waiting period indicated, HPLC tests were carried out according to the above. The results are shown in the table below, in which the percentages represent the quantity of prodrug D or UCM924 detected in the samples. Therefore, a higher percentage means that the drug was more stable in the conditions indicated in the table.

As can be seen in the table below, prodrug D was more stable after 24 hours. Prodrug D stability at different PH was as follows: acidic>neutral>basic

| | | | HPLC Method 1 | | HPLC Method 2 | | |
|---|---|---|---|---|---|---|---|
| Entry | Conditions | | Prodrug D % | UCM924% | Prodrug D % | UCM924% | pH |
| 1 | $H_2O$ | 0 h | 90.15 | — | 93.92 | — | ~7.0 |
| 2 | $H_2O$ | overnight at rt | — | — | 18.28 | 80.09 | ~7.0 |
| 3 | 40% PEG400:60% $H_2O$ | overnight at rt | — | — | 58.17 | 40.16 | ~7.0 |

-continued

| | | | HPLC Method 1 | | HPLC Method 2 | | |
|---|---|---|---|---|---|---|---|
| Entry | Conditions | | Prodrug D % | UCM924% | Prodrug D % | UCM924% | pH |
| 4 | 1N HCl | overnight at rt | — | — | 85.21 | 14.79 | ~0 |
| 5 | Saturated $NaHCO_3$aq | 2 h at rt | — | — | 27.21 | 62.33 | ~8.5 |

rt = room temperature;
TFA = trifluoroacetic acid

Example 8—Pharmacokinetic Studies

In vivo pharmacokinetic studies of prodrug D were carried in male rats (Sprague-Dawley, weight 210-214 grams) and male dogs (Beagles, weight 8960-9820 grams).

Method

Animals were housed under standard conditions and had free access to water and standard laboratory diet. Care and husbandry of animals were in conformity with the institutional guidelines, in compliance with national and international laws and policies (EEC Council Directive 86/609, OJL 358 m, 1, December 122, 1987; NIH Guide for the care and Use of Laboratory Animals, NIH Publication No. 86-23, 1985). The compounds were dissolved in water containing 40% PEG 400 at a concentration of 15 mg/ml (clear solution) for the PO dose for Dog, or in water containing 40% PEG 400 at a concentration of 12.5 mg/ml (clear solution) for the PO dose for Rat.

Dogs were randomly assigned to treatment groups (n=3) and received a single oral administration (15 mg/kg) through oral gavage of Prodrug D and the level of the active metabolite UCM924 was then measured.

Rats were randomly assigned to treatment groups (n=3) and received a single oral administration (50 mg/kg) of Prodrug D and the level of the active metabolite UCM924 was then measured.

Serial blood samples (200 μL) were collected from caudal vein at 5, 15, 30, 60, 120, 240, 360, 480 and 1440 min after PO administration. Blood samples were collected into a prechilled commercial tube (Jiangsu Kangjian medical supplies co., LTD) containing Potassium (K2) EDTA (0.85-1.15 mg). Gently mixed and placed on ice; then . . . blood was centrifuged (3000×g, at 2-8° C. for 10 min), the plasma was collected and immediately frozen at −60° C. or below until submission to UPLC/MS/MS analysis.

For the sample preparation, An aliquot of 40 UL calibration standard, quality control, single blank and double blank samples were added to the 1.5 ml tube; Each sample (except the double blank) was quenched with 400 μL IS1 respectively (double blank sample was quenched with 400 UL MeOH with 0.1% FA), and then the mixture was vortex-mixed well (at least 15 s) with vortexer and centrifuged for 15 min at 12000 g, 4° C.; 50 UL supernatant was transfer to the 96-well plate and centrifuged for 5 min at 3220 g, 4° C., then the supernatant were directly injected for LC-MS/MS analysis.

UPLC/MS/MS analysis were performed on an Acquity UPLC, coupled with a sample organizer and interfaced with a DMPK-LCMS-11-SMBA_Triple Quad 6500 Plus. LC runs (inj. vol. 2 μL) were carried out at 50° C. on Acquity BEH C18 columns (1.7 μm, 2.1×50 mm) at a flow rate of 0.7 mL/min. Mobile phases consisted of a phase A [0.1% FA and 2 mM $HCOONH_4$ in $H_2O$/ACN (95/5)] and a phase B [0.1% FA and 2 mM $HCOONH_4$ in $H_2O$/ACN (5/95)]. The column was conditioned with 15% phase B, then brought to 95% phase B within 1.2 min and maintained at these conditions for 0.2 min. Analyses were carried out using a positive electrospray ionization [ESI(+)] interface in multiple reaction monitoring (SRM) mode.

Pharmacokinetic analysis was performed by PO & Metabolite-Noncompartmental model 200 (extravascular input) analysis and using the Phoenix WinNonlin 6.3 software.

To evaluate the in vivo behavior of the UCM924 and Prodrug-D, a preliminary pharmacokinetic (PK) study was carried out in both male dogs and rats. Prodrug-D was administrated by oral gavage (PO) at doses of 15 or 50 mg/kg, in dog and rats respectively and the UCM924 was measured in plasma. UCM924 (20 mg/kg) was also administered per os in rats and IV in dogs (2 mg/kg) and it was measured in plasma.

Data of Prodrug (per os) were compared to rats treated with UCM924 per os

Data of Prodrug (per os) were compared to dogs treated with UCM924 IV.

Results

Pharmacokinetics of Prodrug D in Rats

Prodrug D (50 mg/kg, gavage) per os in rats, compared to UCM924 per os in rats (20 mg/kg per os), produces an increased AUC and Cmax of circulating UCM924 and improves the half-life.

RATS-Comparison of UCM924 plasmatic level after UCM924 per os vs Prodrug D per os.

| | $AUC_{0-last}$ (ng · h/mL) | $C_{max}$ (ng $mL^{-1}$) | $T_{1/2}$ (h) |
|---|---|---|---|
| UCM924 20 mg/kg per os | 97.7 ± 61 | 42 ± 34 | N.D. |
| Prodrug D 50 mg/kg per os | 735 ± 307 | 245 ± 149 | 1.24 ± 0.1 |

AUC: area under the plasma concentration-time curve of the drug;
$t_{1/2}$: half-life;
Cmax: maximal concentration Pharmacokinetics of Prodrug D in Dogs.

Prodrug D (15 mg/kg, gavage) per os in dogs, compared to UCM924 (2 mg/kg, i.v.) reaches high level of AUC and Cmax of circulating UCM924 and optimal half-life.

DOGS-Comparison of UCM924 plasmatic level after UCM924 endovenously vs Prodrug D per os.

| | $AUC_{0-last}$ (ng · h/mL) | $C_{max}$ (ng $mL^{-1}$) | $T_{1/2}$ (h) |
|---|---|---|---|
| UCM924 2 mg/kg IV | 1687 ± 275 | N.D. | 1.79 ± 0.4 |

-continued

| | $AUC_{0\text{-}last}$ (ng · h/mL) | $C_{max}$ (ng $mL^{-1}$) | $T_{1/2}$ (h) |
|---|---|---|---|
| Prodrug D 15 mg/kg per os | 2181 ± 123 | 1233 ± 116 | 1.53 ± 0.4 |

Figure 4:
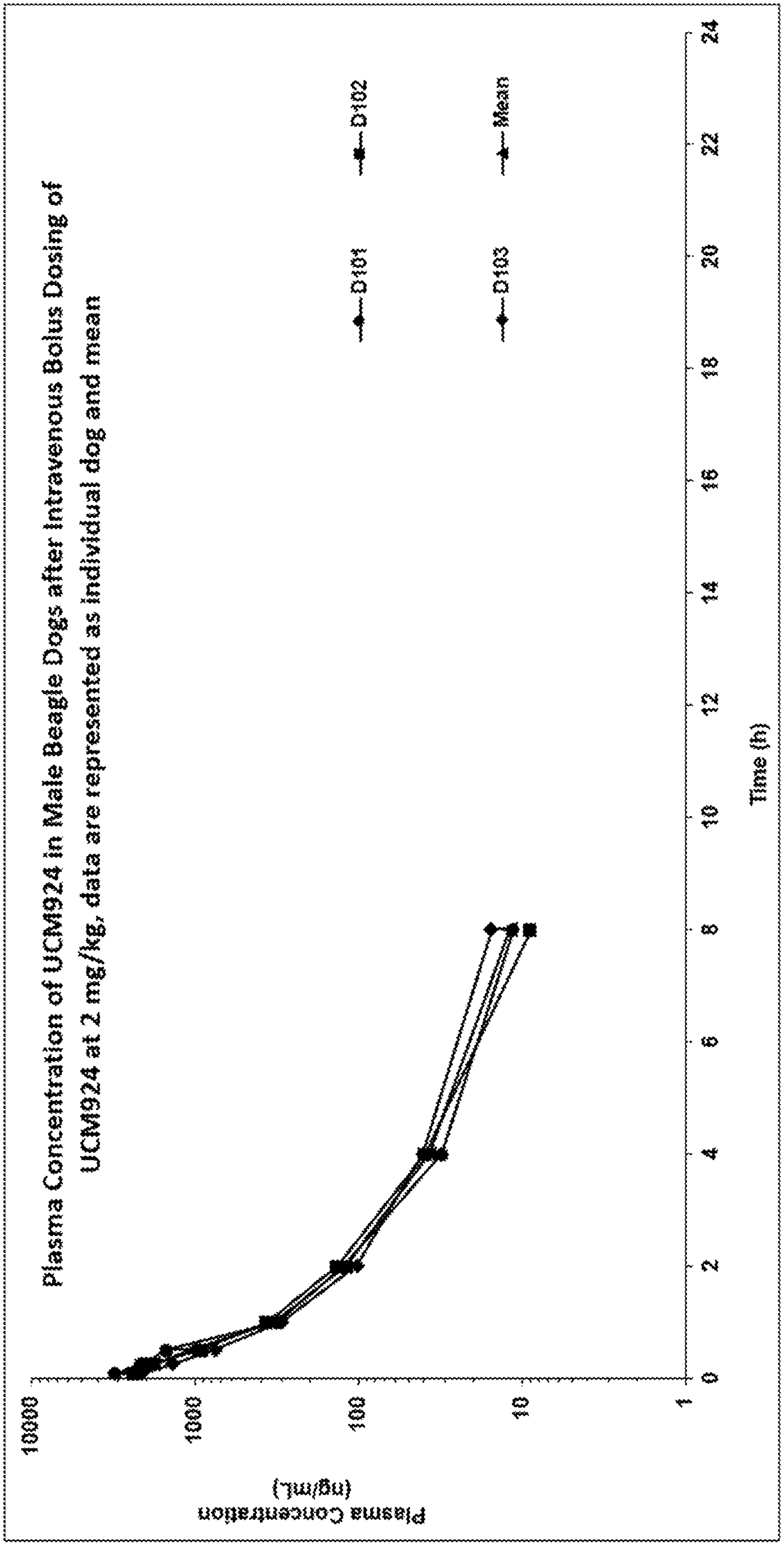
FIG. 4 shows the plasma Concentration of UCM924 in Male Beagle Dogs after Intravenous Bolus Dosing of UCM924 at 2 mg/kg, data are represented as individual dog and mean.
Figure 5:
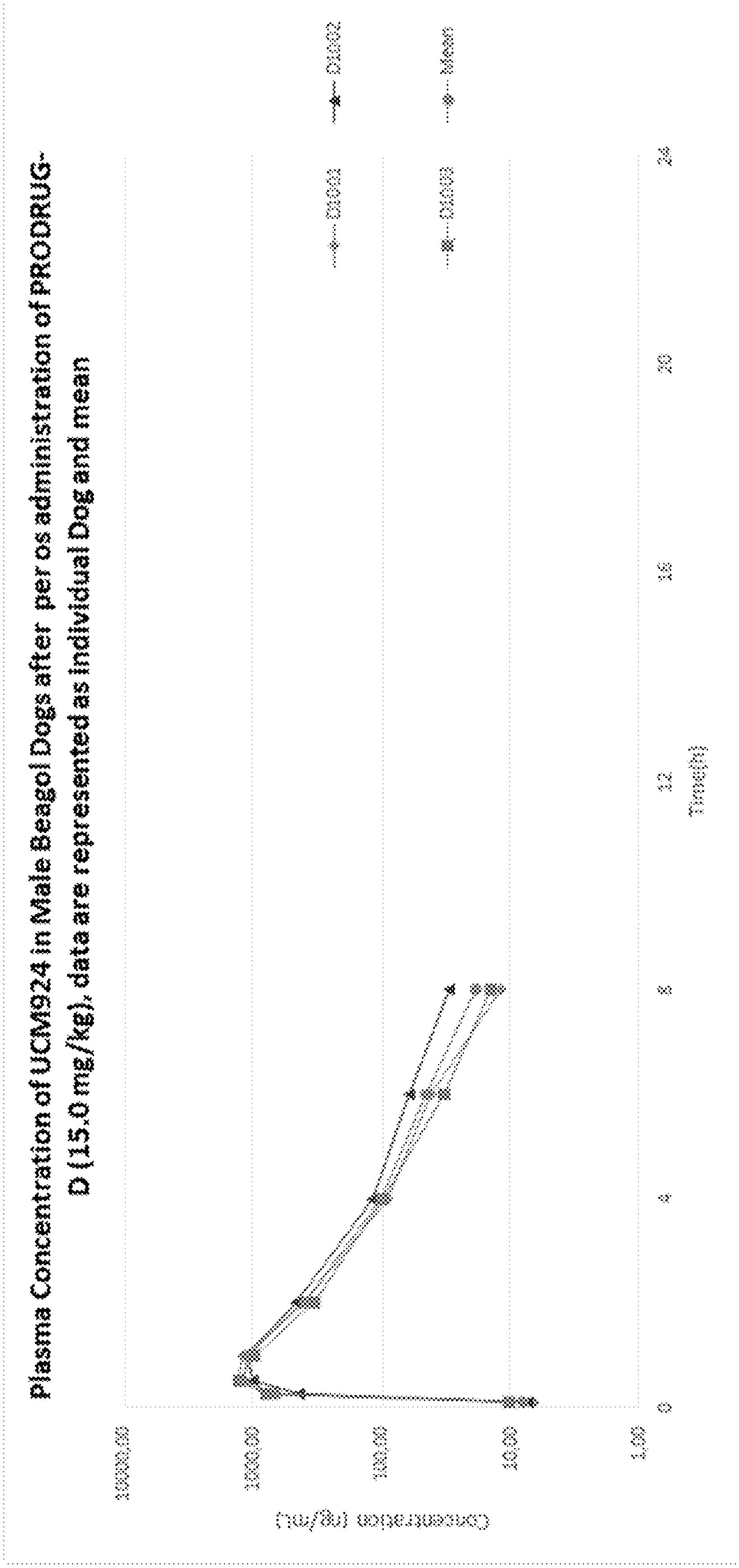
FIG. 5 shows the plasma Concentration of UCM924 in Male Beagol Dogs after per os administration of PRODRUG-D (15.0 mg/kg), data are represented as individual Dog and mean.

AUC: area under the plasma concentration-time curve of the drug;
$t_{1/2}$: half-life;
Cmax: maximal concentration As can be seen from the above table and FIGS. 4 and 5 (wherein D1001-D1003, represent each dog), prodrug D administered per os to dogs provided an optimal linear pharmacokinetic curve, compatible with a further development of the drug in humans. Moreover, the AUC after oral administration was bigger than the IV administration.

The pharmacokinetic data on rats and on dogs demonstrate that the Prodrug D has an optimal pharmacokinetics in larger mammalian, predicting an optimal pharmacokinetic in humans. Rats are indeed known to be rapid metabolizers (Suckow et al., 2019) and not optimal for the study of the pharmacokinetics of oral drugs in humans. However, in spite of these limitations, Prodrug D was able to produce analgesic, antianxiety and hypnotic effects in rats. We expect thus to have the same effects in humans by using a smaller oral dose of Prodrugs.

Example 9—Anti-Anxiety Effects of Pro-Drug D

Material and Methods

Drug Administration

Prodrug D 150 mg/kg was dissolved in tap water per oral gavage. The solution was prepared <30 seconds before administration (100 μL administration volume).

Behavioral tests performed 2.5-3 hours after drug administration. 8 mice ($C_{57}$/BL) per group were used received vehicle or Prodrug D.

Elevated Plus Maze Test (EPMT)

The EPMT was used to assess anxiety-like reactivity as induced suppression of exploratory behavior. The maze was made of white Plexiglass and consisted of two open arms (16×5 cm) opposite each other and two walled arms (16×5×12 cm) opposite each other. The plus maze was raised 50 cm above ground and had a 5×5 cm central platform forming the intersection of the four arms. The mice were each placed on the central platform facing one of the open arms. EPMT behavior was recorded for 5 min under bright white light (100 W). Behavioral endpoints that were analyzed included time spent in the open vs closed arms, frequency of open arm vs closed arm entries, time spent(s) on the central platform. Anxiolytic agents are known to increase open arm visits and time in the open arm. Anxiogenics increase closed arm visits.

The percentage of the time spent in the open arms was calculated employing the formula OA %=OA/OA+CA, where OA represents the time(s) spent in open arms and CA is the time(s) spent in the closed arms. Behavioral experiments were recorded and analyzed using an automated tracking system (Video track, View Point Life Science, Montreal, Canada) equipped with infrared lighting-sensitive CCD cameras (Bambico F R et al., 2010).

Results of the EPMT

Figure 6A:
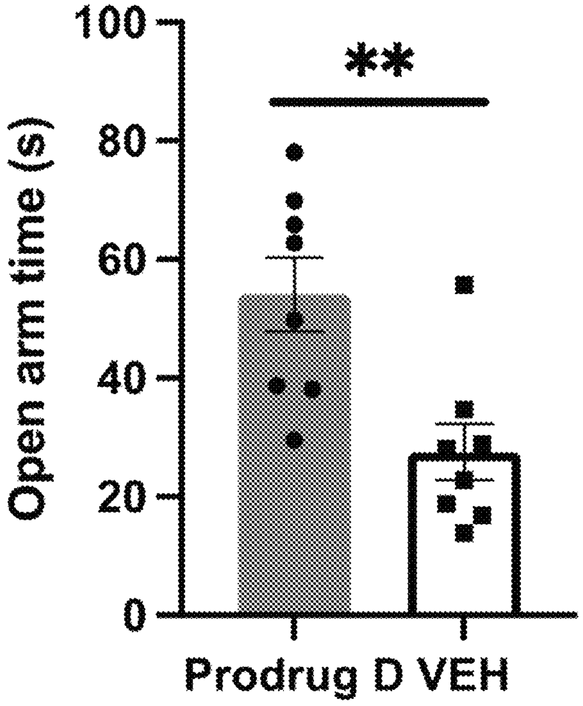
FIG. 6A-D shows the antianxiety effect of Prodrug D in the elevated plus maze test in mice.
Figure 6B:
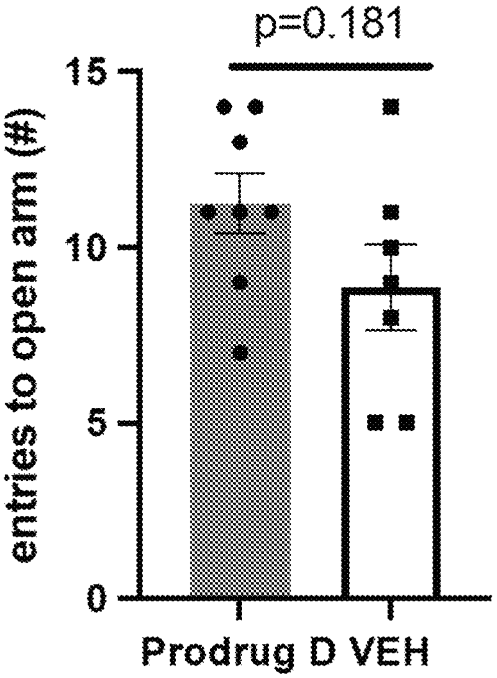
Figure 6C:
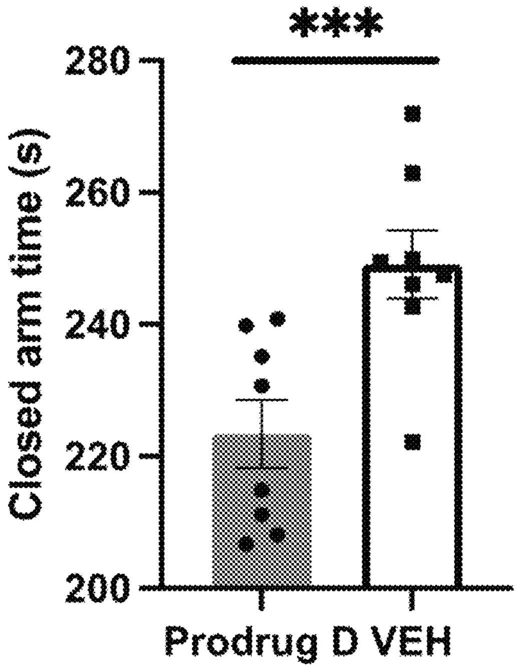
Figure 6D:
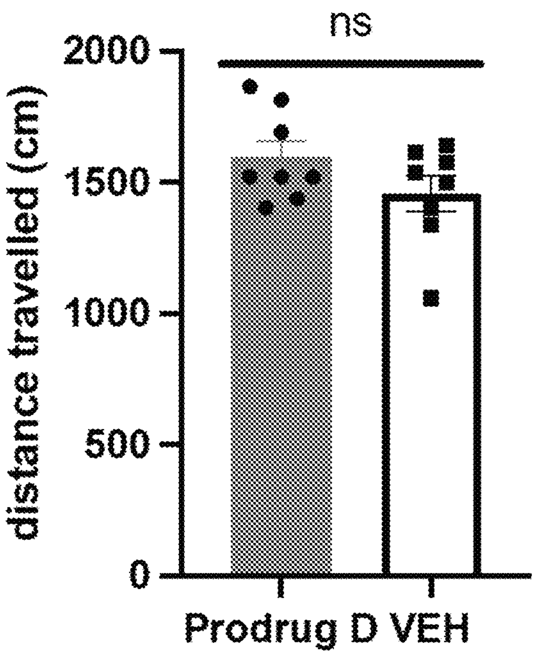

As shown in FIG. 6 and in the table below, prodrug D has antianxiety effects: since it increases time (FIG. 6A) and number of entries (FIG. 6B, trend) in the open arm and decreases time spent in the closed arm (FIG. 6C), with no effects on locomotion (FIG. 6D). Mann Whitney test

| TABLE Analyzed | open arm time | entries to open | closed arm time | total distance |
|---|---|---|---|---|
| Column B vs. Column A | VEH vs. Prodrug D | VEH vs. Prodrug D | VEH vs. Prodrug D | VEH vs. Prodrug D |
| Mann Whitney test | | | | |
| P value | 0.003 | 0.1425 | 0.0019 | 0.3282 |
| Exact or approximate P value? | Exact | Exact | Exact | Exact |
| P value summary | ** | almost significative | ** | non-significative |
| Significantly different (P < 0.05)? | Yes | No | Yes | No |
| One- or two-tailed P value? | Two-tailed | Two-tailed | Two-tailed | Two-tailed |
| Sum of ranks in column A, B | 95, 41 | 77, 43 | 40, 96 | 78, 58 |
| Mann-Whitney U | 5 | 15 | 4 | 22 |
| Difference between medians | | | | |
| Median of column A | 56.30, n = 8 | 11.00, n = 8 | 222.8, n = 8 | 1521, n = 8 |
| Median of column B | 25.45, n = 8 | 9.000, n = 7 | 248.6, n = 8 | 1519, n = 8 |
| Difference: Actual | −30.85 | −2 | 25.75 | −2.35 |
| Difference: Hodges-Lehmann | −25.9 | −2.5 | 29.45 | −116.6 |

** p < 0.01,
***p < 0.001

Example 10-Pro-Drug D-Sleep Restoration in Neuropathic Rats

Material and Methods

Animals

Wistar rats weighted 120 g at the beginning of the experiment were housed under standard conditions, at a constant temperature of 22° C., with food and water provided ad libitum and under a 12 h light/dark cycle (lights on at 7:00 AM; lights off at 7:00 PM). All experimental procedures and surgeries were approved by the Animal Ethics Committee of local institutional committee for animal use and care (McGill University, Canada), following the Canadian Institute of Health Research for animal care and scientific use.

Spared Nerve Injury (SNI) & Assessment of Mechanical Allodynia

See above

Electroencephalogram (EEG) and Electromyogram (EMG) Implantation

Only animals presenting allodynia (mean 2.5 gr) 14 days after SNI surgery, were then implanted EEG/EMG electrode, for 24 hours electrical recording and non-allodynic rat were excluded.

Sham and neuropathic rats were deeply anesthetized with isoflurane (5% for induction, 2-3% for maintenance) and placed in a stereotaxic frame. For EEG monitoring, three stainless-steel epidural electrodes were positioned through 1.5 mm burr holes at −2 mm anteroposterior (AP) and −3 mm lateral (L), 4.5 mm AP and +3 mm L, −7 mm AP and −3 mm AP according to bregma (Paxinos and Watson 2006). For the EMG signal, three flexible stainless-steel wires were implanted into the neck muscle. Then, wires and connectors were fixed to the skull using dental acrylic (Coltene/Whaledent Inc. USA). Rats were given 5 days to recovery (Ochoa-Sanchez, et al., 2011).

EEG/EMG Habituation 24-h after electrode implantation surgery, rats were placed for habituation in the recording room from 12:00 PM to 9:00 PM on a daily basis. During this time, the rats were placed in the recording chambers and connected to a flexible 6-flat cable (3M Scotchflex®), in a freely moving manner. No recordings were performed, but tolerance to the cable, and sleep behavior were observed. The day 5 of habituation, recordings were performed for 24 h, starting at 6:00 PM.

Administration of Prodrug D

Prodrug D (150 mg/kg) was dissolved in 40% PEG 400 and 60% water (about 2.5 mL average for rats by gavage) and was administered at 6 am and 6 μm.

EEG/EMG Recordings

The amplification of EEG/EMG signals were at the total gain of 10.000. EEG/EMG signals were digitalized by a CED 1401 interface system, processed on-line, and analyzed off-line by Spike 2 software, in parallel with analog-to-digital samplings of amplified (Grass, P55) polygraphic signals (EEG; sampling rate, 100 or 200 Hz). Consecutive 10-s epochs were subjected to a Fast Fourier Transform (FFT) and EEG power spectra density was computed in the frequency range of 0-64 Hz (Ochoa-Sanchez, R et al., 2011).

Analysis of EEG and EMG Data

Analysis was made offline using the spike 2 software (Cambridge). Three classical sleep stages are identified using EEG and EMG recordings. Wakefulness was determined by a sustained activity of EMG and low amplitude and high frequency of EEG. NREM (non-rapid eyes movement) sleep was characterized by high amplitude δ wave (1-4 Hz) and low muscle activity. REM (rapid eyes movement) sleep was marked with muscle atonia as observed in EMG and low amplitude 0 wave in EEG (6-11). Only period longer than 10 seconds was marked for further analysis of awake, REM and NREM sleep, in order to eliminate the transitional period such as drowsiness (Ochoa-Sanchez, R et al., 2011).

Sleep Fragmentation Index

Given the changes induced by the neuropathy on sleep parameters, we then calculate the sleep fragmentation index (SFI). SFI was calculated as the total number of awakenings in 24 h divided by the total sleep time in hours.

Statistical Analysis

Data analysis was done using GraphPad Prism statistical software version 5.04 (Systat Software, Inc.). One-way ANOVA was performed for 24 h time of REM, NREM and wakefulness as well as sleep fragmentation index. Post-hoc analyses were performed using the Bonferroni t-test comparisons. All data are expressed as mean±SEM. $P<0.05$ was considered significant.

Results

Prodrug D reverses the sleep reduction and sleep fragmentation induced by Neuropathic Pain.

Figure 7A:
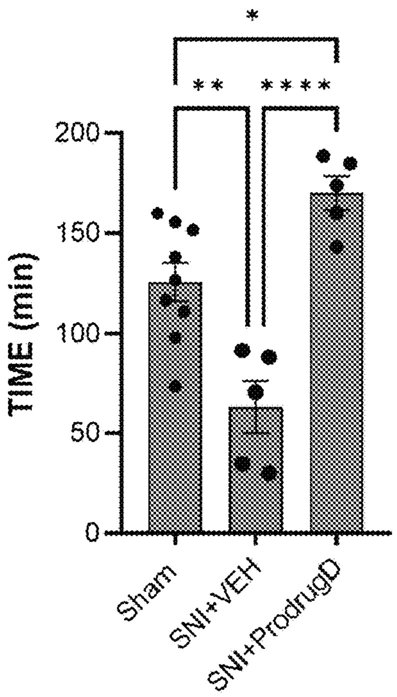
FIG. 7A-D shows the sleep restoration effect of Prodrug D in neuropathic (SNI) rats treated with vehicle (VEH) or Prodrug D.
Figure 7B:
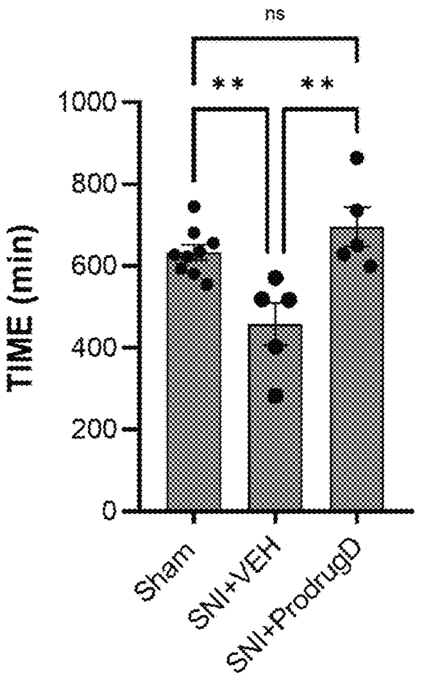
Figure 7C:
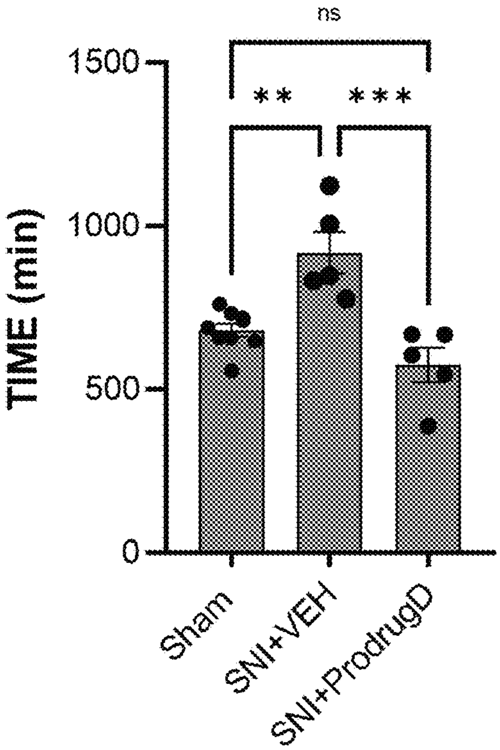
Figure 7D:
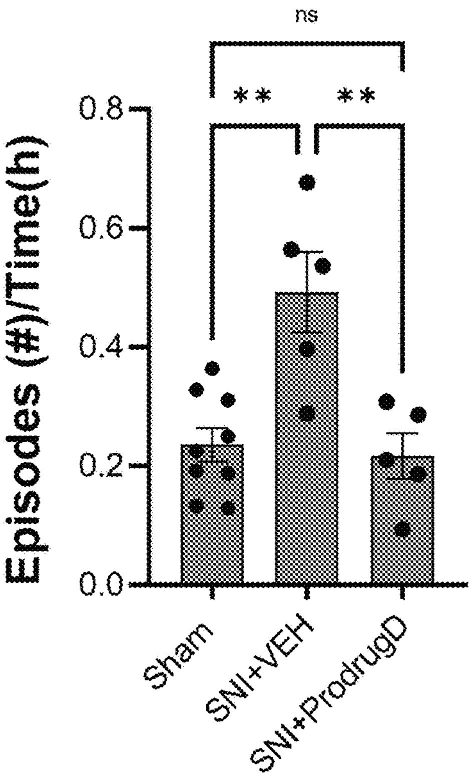

We measured the EEG/EMG parameters (wakefulness, NREM and REM sleep) for 24 hours in three groups of rats. The first group were sham rats (n=9), the second group were SNI+VEH (n=5), and the third group were SNI+ProdrugD (n=5). Results indicate that neuropathic animals (SNI) have a decrease time in REM (FIG. 7A), NREM (FIG. 7B) during 24 h as well as an increase time in wakefulness (FIG. 7C).

Prodrug D (150 mg/kg) was able to restore all the three parameters (FIG. 7). More importantly, neuropathic rats have sleep fragmentation (total number of awakenings in 24 h divided by the total sleep time in hours) and Prodrug D was able to reverse the fragmentation-see FIG. 7D—and the table below for One-Way ANOVA results.

Neuropathic (SNI) rats treated with vehicle (VEH) have disrupted sleep: shorter REM time (A), shorter NREM time (B), increase time in wakefulness (C), and increased sleep fragmentation index (SFI), and Prodrug D reverses these parameters in SNI rats, by normalizing all sleep parameters (see FIG. 7A-D and the table below).

Effect of Prodrug D on Sleep Restoration

| | Bonferroni's multiple comparison test | Mean difference | 95.00% CI of difference | Significant? | Summary | Adjusted P Value |
|---|---|---|---|---|---|---|
| REM | Sham vs SNI + VEH | 62.59 | 22.67 to 102.5 | Yes | ** | 0.0021 |
| 24 h | Sham vs SNI + Prodrug D | −44.39 | −84.30 to −4.474 | Yes | * | 0.0269 |
| | Control vs SNI + Prodrug D | −107 | −152.2 to −61.72 | Yes | **** | <0.0001 |
| NREM | Sham vs SNI + VEH | 174.1 | 41.92 to 306.2 | Yes | ** | 0.0085 |
| 24 h | Sham vs SNI + Prodrug D | −62.39 | −194.5 to 69.70 | No | Non-significative | 0.6745 |
| | Control vs SNI + Prodrug D | −236.5 | −386.2 to −86.68 | Yes | ** | 0.002 |

-continued

| | Bonferroni's multiple comparison test | Mean difference | 95.00% CI of difference | Significant? | Summary | Adjusted P Value |
|---|---|---|---|---|---|---|
| Wake 24 h | Sham vs SNI + VEH | −236.6 | −388.0 to −85.32 | Yes | ** | 0.0021 |
| | Sham vs SNI + Prodrug D | 106.8 | −44.55 to 258.1 | No | Non-significative | 0.2327 |
| | Control vs SNI + Prodrug D | 343.4 | 171.8 to 515.0 | Yes | *** | 0.0002 |
| SFI | Sham vs SNI + VEH | −0.257 | −0.4146 to −0.09935 | Yes | ** | 0.0015 |
| | Sham vs SNI + Prodrug D | 0.01886 | −0.1388 to 0.1765 | No | Non-significative | >0.9999 |
| | Control vs SNI + Prodrug D | 0.2758 | 0.09710 to 0.4546 | Yes | ** | 0.0024 |

Sham = 9,
SNI + VEH = 5,
SNI + ProdrugD = 5,
One-way ANOVA, followed by Bonferroni post-hoc test,
*$p < 0.05$,
**$p < 0.01$,
**** $p < 0.0001$ The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

Electronic Medicine Compendium (EMC), entry onValdoxan 25 mg film-coated tablets, https://www.medicines.org.uk/EMC/medicine/21830/SPC/Valdoxan/, last updated on 13 Jul. 2020.

Valdoxan 25 mg film-coated tablet, Package Leaflet: Information for the patient, Europe, Les Laboratoires-Servier, pages 1-4, last revised May 2020.

"Valdoxan: EPAR-Product Information" made up toAnnexes I to IIIB, documentfromthe European Medicines Agency (EMA) database, last updated on Sep. 18, 2017, available at https://www.ema.europa.eu/en/medicines/human/EPAR/valdoxan #product-information-section (datebase entry on Valdoxan) and https://www.ema.europa.eu/en/documents/product-information/valdoxan-epar-product-information en.pdf (specific documents including Annexes I to IIIB).

NDA 21-782, Rozerem (ramelteon) tablets, FDA documentaccessed via the Drugs@FDA database, documentlabelled "Approval" in the database, dated Jul. 17, 2005, pages 4-21 followed by packaging, available at www.accessdata.fda.gov/drugsatfda_docs/label/2005/021782lbl.pdf.

FDA Final Labeling 21782/Supp 001, Rozerem (ramelteon) tablets, FDA documentaccessed via the Drugs@FDA database, document labelled "Labelling" in the database, dated Nov. 9, 2010, available at https://www.accessdata.fda.gov/drugsatfda_docs/label/2010/021782s011lbl.pdf.

International patent publication no. WO2007/079593 A1

International patent publication no. WO2015021535A1

American Psychiatric Association. (2013). *Diagnostic andstatistical manual of mental disorders* (5th ed.). Washington, DC:

Bambico, F. R., Cassano, T., Dominguez-Lopez, S., Katz, N., Walker, C. D., Piomelli, D., & Gobbi, G. (2010). Genetic deletion of fatty acid amide hydrolase alters emotional behavior and serotonergic transmission in the dorsal raphe, prefrontal cortex, and hippocampus. *Neuropsychopharmacology,* 35(10), 2083-2100.

Righi, M.; Bedini, A.; Piersanti, G.; Romagnoli, F.; Spadoni, G.; *J. Org. Chem.* 2011, 76, 704

Bubenik, G. A. (2002). "Gastrointestinal melatonin: localization, function, and clinical relevance." *Dig Dis Sci* 47(10): 2336-2348.

Carrillo-Vico, A., J. R. Calvo, P. Abreu, P. J. Lardone, S. Garcia-Maurino, R. J. Reiter and J. M. Guerrero (2004). "Evidence of melatonin synthesis by human lymphocytes and its physiological significance: possible role as intracrine, autocrine, and/or paracrine substance." *Faseb* j18(3): 537-539.

Chaplan, S. R., Bach, F. W., Pogrel, J. W., Chung, J. M., &Yaksh, T. L. (1994). Quantitative assessment of tactile allodynia in the rat paw. *Journal of neuroscience methods,* 53(1), 55-63.

Claustrat, B., J. Brun and G: Chazot (2005). "The basic physiology and pathophysiology of melatonin." *Sleep Med Rev*9(1): 11-24.

Comai, S. and G. Gobbi (2014). "Unveiling the role of melatonin MT2 receptors in sleep, anxiety and other neuropsychiatric diseases: a novel target in psychopharmacology." *J Psychiatry Neurosci* 39(1): 6-21.

Comai, S., R. Ochoa-Sanchez, S. Dominguez-Lopez, F. R. Bambico and G. Gobbi (2015). "Melancholic-Like behaviors and circadian neurobiological abnormalities in melatonin MT1 receptor knockout mice." *Int J Neuropsychopharmacol* 18(3).

Comai, S., R. Ochoa-Sanchez and G. Gobbi (2013). "Sleep-wake characterization of double MT1/MT2 receptor knockout mice and comparison with MT1 and MT2 receptor knockout mice." *Behavioural Brain Research* 243(1): 231-238.

Comai, S., R. Ochoa-Sanchez and G. Gobbi (2013). "Sleep-wake characterization of double MT (1)/MT (2) receptor knockout mice and comparison with MT (1) and MT (2) receptor knockout mice." *Behav Brain Res* 243: 231-238.

Decosterd, I., & Woolf, C. J. (2000). Spared nerve injury: an animal model of persistent peripheral neuropathic pain. *Pain,* 87(2), 149-158.

Dhillon, S. and M. Clarke (2014). "Tasimelteon: first global approval." *Drugs* 74(4): 505-511.

Doolen, S., D. N. Krause, M. L. Dubocovich and S. P. Duckles (1998). "Melatonin mediates two distinct responses in vascular smooth muscle." *European Journal of Pharmacology* 345(1): 67-69.

Dubocovich, M. L., P. Delagrange, D. N. Krause, D. Sugden, D. P. Cardinali and J. Olcese (2010). "International Union of Basic and Clinical Pharmacology. LXXV. Nomenclature, Classification, and Pharmacology of G Protein-Coupled Melatonin Receptors." *Pharmacological Reviews* 62(3): 343-380.

Dubocovich, M. L., R. L. Hudson, I. C. Sumaya, M. I. Masana and E. Manna (2005). "Effect of MT1 melatonin receptor deletion on melatonin-mediated phase shift of circadian rhythms in the C57BL/6 mouse." *Journal of Pineal Research* 39(2): 113-120.

Gobbi, G. and S. Comai (2019). "Differential Function of Melatonin MT1 and MT2 Receptors in REM and NREM Sleep." *Front Endocrinol* 10(87).

Jockers, R., P. Delagrange, M. L. Dubocovich, R. P. Markus, N. Renault, G. Tosini, E. Cecon and D. P. Zlotos (2016). "Update on melatonin receptors: IUPHAR Review 20." *Br J Pharmacol* 173(18): 2702-2725.

Johansson, L. C., B. Stauch, J. D. McCorvy, G. W. Han, N. Patel, X. P. Huang, A. Batyuk, C. Gati, S. T. Slocum, C. Li, J. M. Grandner, S. Hao, R. H. J. Olsen, A. R. Tribo, S. Zaare, L. Zhu, N. A. Zatsepin, U. Weierstall, S. Yous, R. C. Stevens, W. Liu, B. L. Roth, V. Katritch and V. Cherezov (2019). "XFEL structures of the human $MT_2$ melatonin receptor reveal the basis of subtype selectivity." *Nature* 569(7755): 289-292.

Jornada, D. H., G. F. dos Santos Fernandes, D. E. Chiba, T. R. de Melo, J. L. dos Santos and M. C. Chung (2015). "The Prodrug Approach: A Successful Tool for Improving Drug Solubility." *Molecules* 21(1): 42.

Karasek, M. (2007). "Does melatonin play a role in aging processes?" *J Physiol Pharmacol* 58 Suppl 6:105-113.

Kuriyama, A., M. Honda and Y. Hayashino (2014). "Ramelteon for the treatment of insomnia in adults: a systematic review and meta-analysis." *Sleep Med*15(4): 385-392.

Lacoste, B., D. Angeloni, S. Dominguez-Lopez, S. Calderoni, A. Mauro, F. Fraschini, L. Descarries and G. Gobbi (2015). "Anatomical and cellular localization of melatonin $MT_1$ and $MT_2$ receptors in the adult rat brain." *J Pineal Res* 58(4): 397-417.

Lemoine, P., D. Garfinkel, M. Laudon, T. Nir and N. Zisapel (2011). "Prolonged-release melatonin for insomnia—an open-label long-term study of efficacy, safety, and withdrawal." *Ther Clin Risk Manag* 7: 301-311.

Lemoine, P. and N. Zisapel (2012). "Prolonged-release formulation of melatonin (Circadin) for the treatment of insomnia." *Expert Opin Pharmacother* 13(6): 895-905.

Liu, J. and L. N. Wang (2012). "Ramelteon in the treatment of chronic insomnia: systematic review and meta-analysis." *Int J Clin Pract* 66(9): 867-873.

Longatti, P., A. Perin, V. Rizzo, S. Comai, P. Giusti and C. V. Costa (2007). "Ventricular cerebrospinal fluid melatonin concentrations investigated with an endoscopic technique." *J Pineal Res* 42(2): 113-118.

Lopez-Canul, M., S. Comai, S. Dominguez-Lopez, V. Granados-Soto and G. Gobbi (2015). "Antinociceptive properties of selective $MT_2$ melatonin receptor partial agonists." *Eur J Pharmacol* 764: 424-432.

Lopez-Canul, M., S. H. Min, L. Posa, D. De Gregorio, A. Bedini, G. Spadoni, G. Gobbi and S. Comai (2019). "Melatonin MT1 and MT2 Receptors Exhibit Distinct Effects in the Modulation of Body Temperature across the Light/Dark Cycle." *Int J Mol Sci* 20(10).

Lopez-Canul, M., E. Palazzo, S. Dominguez-Lopez, L. Luongo, B. Lacoste, S. Comai, D. Angeloni, F. Fraschini, S. Boccella, G. Spadoni, A. Bedini, G. Tarzia, S. Maione, V. Granados-Soto and G. Gobbi (2015). "Selective melatonin MT2 receptor ligands relieve neuropathic pain through modulation of brainstem descending antinociceptive pathways." *Pain* 156(2): 305-317.

Ochoa-Sanchez, R., S. Comai, B. Lacoste, F. R. Bambico, S. Dominguez-Lopez, G. Spadoni, S. Rivara, A. Bedini, D. Angeloni, F. Fraschini, M. Mor, G. Tarzia, L. Descarries and G. Gobbi (2011). "Promotion of Non-Rapid Eye Movement Sleep and Activation of Reticular Thalamic Neurons by a Novel MT2 Melatonin Receptor Ligand." *J.Neurosci.* 31(50): 18439-18452.

Ochoa-Sanchez, R., Q. Rainer, S. Comai, G. Spadoni, A. Bedini, S. Rivara, F. Fraschini, M. Mor, G. Tarzia and G. Gobbi (2012). "Anxiolytic effects of the melatonin MT (2) receptor partial agonist UCM765: Comparison with melatonin and diazepam." *Prog Neuropsychopharmacol Biol Psychiatry* 39(2): 318-325.

Ohlsen, R. I. and L. S. Pilowsky (2005). "The place of partial agonism in psychiatry: recent developments." *J Psychopharmacol* 19(4): 408-413.

Perreau-Lenz, S., A. Kalsbeek, M. L. Garidou, J. Wortel, J. van der Vliet, C. van Heijningen, V. Simonneaux, P. Pevet and R. M. Buijs (2003). "Suprachiasmatic control of melatonin synthesis in rats: inhibitory and stimulatory mechanisms." *Eur J Neurosci* 17(2): 221-228.

Reiter, R. J. (1991). "Pineal melatonin: cell biology of its synthesis and of its physiological interactions." *Endocr Rev* 12(2): 151-180.

Reiter, R. J., D. X. Tan, R. M. Sainz, J. C. Mayo and S. Lopez-Burillo (2002). "Melatonin: reducing the toxicity and increasing the efficacy of drugs." *J Pharm Pharmacol* 54(10): 1299-1321.

Rivara, S., A. Lodola, M. Mor, A. Bedini, G. Spadoni, V. Lucini, M. Pannacci, F. Fraschini, F. Scaglione, R. Ochoa-Sanchez, G. Gobbi and G. Tarzia (2007). "N-(substituted-anilinoethyl)amides: design, synthesis, and pharmacological characterization of a new class of melatonin receptor ligands." *J.Med. Chem.* 50(26): 6618-6626.

Rivara, S., F. Vacondio, A. Fioni, C. Silva, C. Carmi, M. Mor, V. Lucini, M. Pannacci, A. Caronno, F. Scaglione, G. Gobbi, G. Spadoni, A. Bedini, P. Orlando, S. Lucarini and G. Tarzia (2009). "N-(Anilinoethyl) amides: Design Metabolically Stable, Selective and Synthesis of Melatonin Receptor Ligands." *Chemmedchem* 4(10): 1746-1755.

Spadoni, G., C. Balsamini, G. Diamantini, A. Tontini, G. Tarzia, M. Mor, S. Rivara, P. V. Plazzi, R. Nonno, V. Lucini, M. Pannacci, F. Fraschini and B. M. Stankov (2001). "2-N-acylaminoalkylindoles: design and quantitative structure-activity relationship studies leading to MT2-selective melatonin antagonists." *J Med Chem* 44(18): 2900-2912.

Srinivasan, V., S. R. Pandi-Perumal, I. Trakht, D. W. Spence, R. Hardeland, B. Poeggeler and D. P. Cardinali (2009). "Pathophysiology of depression: role of sleep and the melatonergic system." *Psychiatry Res* 165(3): 201-214.

Stauch, B., L. C. Johansson, J. D. McCorvy, N. Patel, G. W. Han, X. P. Huang, C. Gati, A. Batyuk, S. T. Slocum, A. Ishchenko, W. Brehm, T. A. White, N. Michaelian, C. Madsen, L. Zhu, T. D. Grant, J. M. Grandner, A. Shiriaeva, R. H. J. Olsen, A. R. Tribo, S. Yous, R. C.

Stevens, U. Weierstall, V. Katritch, B. L. Roth, W. Liu and V. Cherezov (2019). "Structural basis of ligand recognition at the human MT1 melatonin receptor." *Nature* 569(7755): 284-288.

Suckow M, Hankenson C, Wilson R, Foley P. (editors). The laboratory rat (2019). *Academic Press;* 3rd edition Thomsen, W. J. and D. P. Behan (2007). 2.20-G Protein-Coupled Receptors. *Comprehensive Medicinal Chemistry II*. J. B. Taylor and D. J. Triggle. Oxford, Elsevier: 771-826.

Tosini, G. and M. Menaker (1998). "The clock in the mouse retina: melatonin synthesis and photoreceptor degeneration." *Brain Res* 789(2): 221-228.

The invention claimed is:

1. A compound of formula (I):

(I)

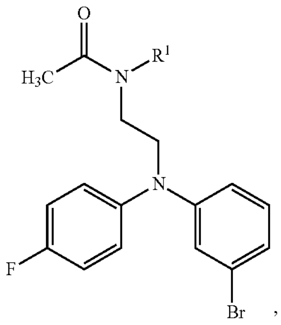

wherein:

$R^1$ is:

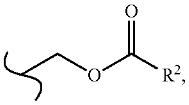, 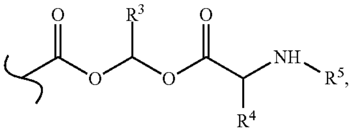, 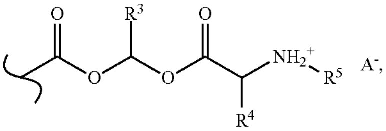 or

-continued

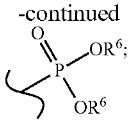

$R^2$ is an alkyl group or an —O-alkyl group;

$R^3$ is H or $CH_3$;

$R^4$ is H or a side chain of an amino acid and $R^5$ is H, or $R^4$ and $R^5$ together with the carbon atom and the nitrogen atom to which they are attached form a pyrrolidinyl group;

$OR^6$ represents OH, $O^-$ $Na^+$, or $O^-$ $K^+$; and $A^-$ is a pharmaceutically acceptable anion, or a pharmaceutically acceptable salt thereof.

2. The compound or pharmaceutically salt thereof of claim 1, wherein the alkyl group and/or the —O-alkyl group in $R^2$ contains between 1 and 18 carbon atoms.

3. The compound or pharmaceutically salt thereof of claim 1, wherein the alkyl group is a $C_{1-6}$ alkyl.

4. The compound or pharmaceutically salt thereof of claim 1, wherein the alkyl in the —O-alkyl group is a $C_{1-6}$ alkyl.

5. The compound or pharmaceutically salt thereof of claim 1, wherein $R^1$ is

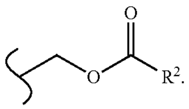

6. The compound or pharmaceutically salt thereof of claim 1, wherein $R^1$ is

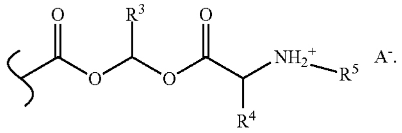

7. The compound or pharmaceutically salt thereof of claim 1, wherein $R^4$ and $R^5$ are:

| $R^4$ | $R^5$ |
|---|---|
| $—CH_3$ | —H |
| $—CH(CH_3)_2$ | —H |
| $—CH(CH_3)—CH_2—CH_3$ | —H |
| $—CH_2—CH(CH_3)_2$ | —H |
| $—(CH_2)_2—S—CH_3$ | —H |
| 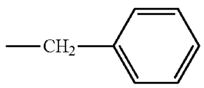 | —H |
| 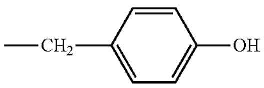 | —H |

-continued

| $R^4$ | $R^5$ |
|---|---|
| 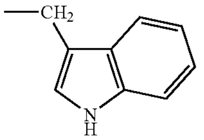 | —H |
| $-CH_2-OH$ | —H |
| $-CH(OH)-CH_3$ | —H |
| $CH_2-C(=O)-NH_2$ | —H |
| $-(CH_2)_2-C(=O)-NH_2$ | —H |
| $-CH_2-SH$ | —H |
| $-CH_2-SeH$ | —H |
| —H | —H |
| $R^4$ and $R^5$ together with the carbon atom and the nitrogen atom to which they are attached form a cyclopentyl group | |
| $-(CH_2)_3-NH-C(=NH_2^+)-NH_2$ | —H |
| 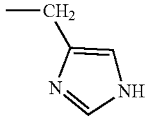 | —H |
| $-(CH_2)_4-NH_3^+$ | —H |
| $-CH_2-COO^-$ | —H |
| $-(CH_2)_2-COO^-$ | —H. |

8. The compound or pharmaceutically salt thereof of claim 1, wherein $R^3$ is H.

9. The compound or pharmaceutically salt thereof of claim 1, wherein $R^3$, $R^4$ and $R^5$ are H.

10. The compound or pharmaceutically salt thereof of claim 1, wherein $R^3$ is $CH_3$.

11. The compound or pharmaceutically salt thereof of claim 1 being:

(N-(2-((3-bromophenyl)(4-fluorophenyl)amino)ethyl)acetamido) methyl pivalate, (N-(2-((3-bromophenyl)(4-fluorophenyl)amino)ethyl)acetamido) methyl ethyl carbonate, 1-((acetyl(2-((3-bromophenyl)(4-fluorophenyl)amino)ethyl)carbamoyl)oxy) ethyl 2-aminoacetate hydrochloride, ((acetyl(2-((3-bromophenyl)(4-fluorophenyl)amino)ethyl)carbamoyl)oxy)methyl 2-aminoacetate hydrochloride, ((acetyl(2-((3-bromophenyl)(4-fluorophenyl)amino)ethyl)carbamoyl)oxy)methyl 2-aminoacetate methanesulfonate, ((acetyl(2-((3-bromophenyl)(4-fluorophenyl)amino)ethyl)carbamoyl)oxy)methyl pyrrolidine-2-carboxylate hydrochloride, (2S)-1-((acetyl(2-((3-bromophenyl)(4-fluorophenyl)amino)ethyl)carbamoyl)oxy)ethyl pyrrolidine-2-carboxylate hydrochloride, or (S)-((acetyl(2-((3-bromophenyl)(4-fluorophenyl)amino)ethyl)carbamoyl)oxy)methyl 2-amino-4-methylpentanoate hydrochloride.

12. The compound or pharmaceutically salt thereof of claim 11, being ((acetyl(2-((3-bromophenyl)(4-fluorophenyl)amino)ethyl)carbamoyl)oxy)methyl 2-aminoacetate hydrochloride.

13. A method for managing or treating a disease, disorder or condition associated with melatonin $MT_2$ receptor activity in a subject in need thereof comprising administering to the subject an effective amount of the compound or pharmaceutically acceptable salt thereof according to claim 1, wherein the disease, disorder or condition associated with melatonin $MT_2$ receptor activity is pain, an anxiety or mood disorder, a sleep, chronobiological or circadian rhythm disorder, hyperthermia, or a metabolic disorder selected from impaired glucose tolerance, insulin resistance and diabetes.

14. The method according to claim 13, wherein said disease, disorder or condition is pain.

15. The method according to claim 14, wherein the pain is chronic pain.

16. The method according to claim 14, wherein the pain is acute pain.

17. The method according to claim 14, wherein the pain is:

chronic pain,
acute tonic pain;
pain relating to surgery;
pain relating to trauma;
hyperalgesia pain;
allodynic pain;
myalgic pain;
inflammatory pain;
neuropathic pain;
headache;
visceral pain;
pelvic pain;
nociceptive pain; and/or
pain associated with a disorder or condition.

18. The method according to claim 17, wherein the nociceptive pain is visceral pain or somatic pain.

19. The method according to claim 17 wherein the neuropathic pain is peripheral neuropathic pain; central neuropathic pain; back pain; joint pain; post-herpetic neuralgia, cancer-related pain, pain related to spinal cord injury, pain caused by reflex sympathetic dystrophy, HIV-associated pain, phantom pain, post-stroke pain, pain caused by trigeminal neuralgia; and/or head pain.

20. The method according to claim 17, wherein the disorder or condition is fibromyalgia, irritable bowel syndrome, arthritis, ulcer, diabetic neuropathy, sciatica, migraine, and/or pain associated to vulvodynia.

21. The method according to claim 13, wherein the disease, disorder or condition associated with melatonin $MT_2$ receptor activity is a mood disorder or an anxiety disorder.

22. The method according to claim 21, wherein the mood disorder is depression or seasonal affective disorder (SAD).

23. The method according to claim 13, wherein the sleep, chronobiological and/or circadian rhythm disorder is insomnia, apnea insomnia associated to pain, narcolepsy, restless leg syndrome, parasomnias, REM sleep behavior disorder, non-24 hour sleep wake disorders, a sleep disorder associated to a mental disorder, or a sleep-wake disorder.

24. The method according to claim 13, wherein the metabolic disorder is diabetes.

25. A method of manufacture of a compound of formula (II):

(II)

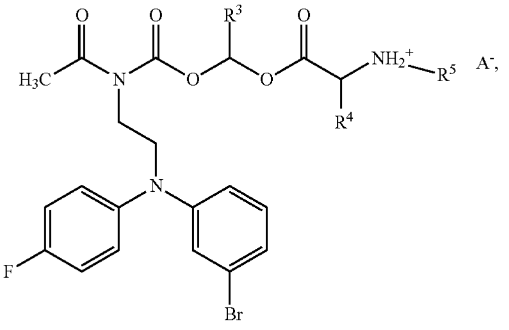

wherein $A^-$, $R^3$, $R^4$ and $R^5$ are as defined in claim 1, the method comprising the steps of:

1) providing N-{2-[(-[(3-bromophenyl)-(4-fluorophenyl)amino]ethyl}acetamide (UCM924):

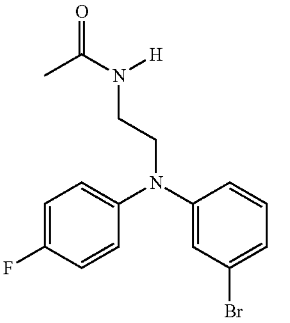

UCM 924 , 2) reacting UCM924 with a first base and a reactant of formula (IV) to produce a chloromethyl intermediate of formula (V):

(IV)

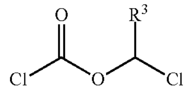

-continued (V)

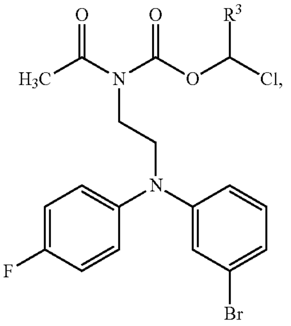

wherein $R^3$ is as defined in claim 1;

3) reacting the chloromethyl intermediate of formula (V) with a second base and a reactant of formula (VI) to produce a protected compound of formula (VII):

(VI)

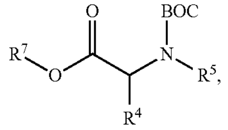

(VII)

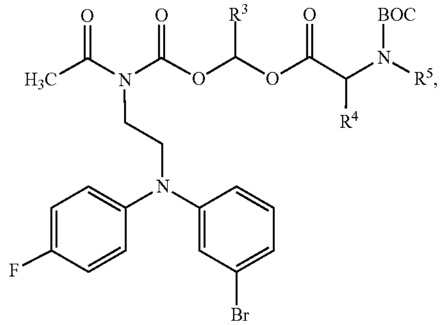

wherein $R^4$ and $R^5$ as described in claim 1, $R_7$ represents H, Li, Na, K, Cs, or Ag, and BOC represents a tert-butyloxycarbonyl protecting group; and 4) reacting the protected compound of formula (VII) with an acid of formula $H^+ E^-$, to produce a salt of formula (VIII):

(VIII)

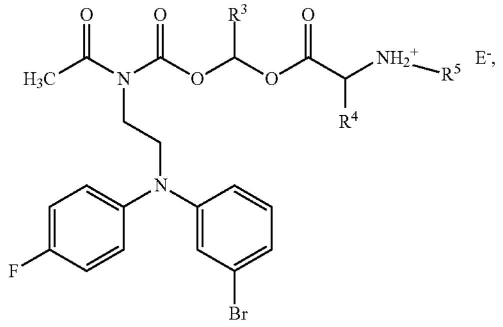

wherein $E^-$ is an anion, and 5) when $E^-$ is not a pharmaceutically acceptable anion, performing a salt metathesis to replace $E^-$ with a pharmaceutically acceptable anion (A), thus producing the compound of formula (II).

26. The method of claim 25, wherein step 2 comprises:

2' preparing a reaction mixture comprising UCM924 and the first base,

2" allowing UCM924 and the first base to react and produce an intermediate of formula (IX):

(IX)

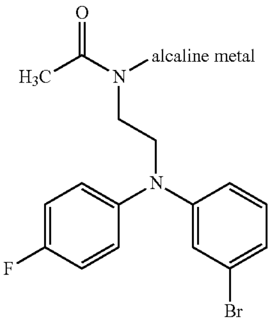

and

2'" reacting the intermediate of formula (IX) with the reactant of formula (IV) to produce a chloromethyl intermediate of formula (V).

27. The method of claim 25, wherein, when the second base is a base of a monovalent metal, step 3 comprises:

3' preparing a reaction mixture comprising the reactant of formula (VI) wherein $R_7$ is H, and the second base, 3" allowing the reactant of formula (VI) and the second base to react and produce a reactant of formula (X):

(X)

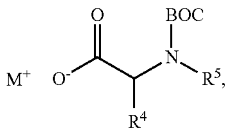

wherein $M^+$ is a monovalent metal cation, and

3'" reacting the intermediate of formula (IX) with the reactant of formula (X) to produce a protected compound of formula (VII).

28. A method of manufacture of a compound of formula (VI):

(VI)

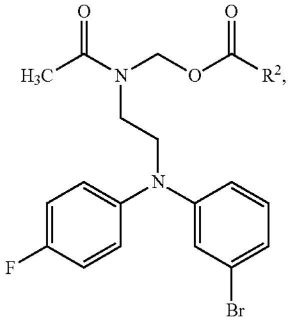

wherein $R^2$ is as described in claim 1, the method comprising the steps of:

A) providing N-{2-[(-[(3-bromophenyl)-(4-fluorophenyl) amino]ethyl}acetamide (UCM924);

UCM 924

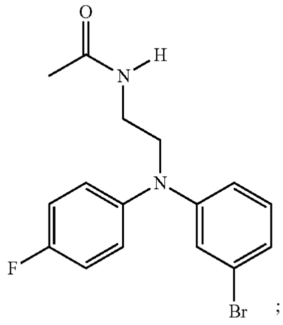

and

B) reacting UCM924 with

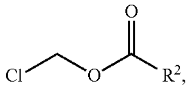

wherein $R^2$ is as described in claim 1, in the presence of NaH thus producing the compound of formula (VI).

* * * * *